US007807181B2

(12) United States Patent
Stephens et al.

(10) Patent No.: US 7,807,181 B2
(45) Date of Patent: Oct. 5, 2010

(54) NEISSERIA MUTANTS, LIPOOLIGOSACCHARIDES AND IMMUNOGENIC COMPOSITIONS

(75) Inventors: David S. Stephens, Stone Mountain, GA (US); Yih-Ling Tzeng, Atlanta, GA (US); Susu Zughaier, Atlanta, GA (US); Shanta Zimmer, Atlanta, GA (US)

(73) Assignee: Emory University, Atlanta, GA (US)

( * ) Notice: Subject to any disclaimer, the term of this patent is extended or adjusted under 35 U.S.C. 154(b) by 971 days.

(21) Appl. No.: 10/508,309

(22) PCT Filed: Mar. 20, 2003

(86) PCT No.: PCT/US03/08795

§ 371 (c)(1),
(2), (4) Date: Sep. 20, 2004

(87) PCT Pub. No.: WO03/079995

PCT Pub. Date: Oct. 2, 2003

(65) Prior Publication Data

US 2005/0106184 A1 May 19, 2005

Related U.S. Application Data

(60) Provisional application No. 60/366,060, filed on Mar. 20, 2002.

(51) Int. Cl.
*A61K 39/02* (2006.01)
*A61K 39/095* (2006.01)
*A61K 39/38* (2006.01)
*A01N 43/04* (2006.01)
*C07H 1/00* (2006.01)

(52) U.S. Cl. .............. 424/234.1; 424/184.1; 424/250.1; 424/249.1; 514/23; 536/123.1

(58) Field of Classification Search .............. 424/234.1, 424/250.1, 249.1, 93.4, 184.1; 514/23; 536/123
See application file for complete search history.

(56) References Cited

U.S. PATENT DOCUMENTS 5,705,161 A 1/1998 Van Der Ley et al. .... 424/250.1
5,952,313 A 9/1999 Carlson ....................... 514/53

FOREIGN PATENT DOCUMENTS

WO WO 00/22430 4/2000
WO WO 00/66791 11/2000

OTHER PUBLICATIONS

Limjuco et al. J. Gen. Microbiol. 104: 187-191, 1978.*
Lee et al. Infect. Immun. 63: 2508-2515, 1995.*
Lodowska et al. Post py higieny i medycyny doswiadczalnej (Online), 61: 106-121, 2007, abstract.*
Bateman, A. (1999) "The SIS domain: a phosphosugar-binding domain," *Trends Biochem*. Sci. 24:94-95.
Belunis et al. (May 1992) "Biosynthesis of endotoxins. Purification and catalytic properties of 3- deoxy-D-manno-octulosonic acid transferase from *Escherichia coli*," *J. Biol. Chem*. 267(14): 9988-9997.
Bigham et al. (Jun. 1984) "Inhibition of arabinose 5-phosphate isomerase. An approach to the inhibition of bacterial lipopolysaccharide biosynthesis," *J. Med. Chem*. 27:717-726.
Brabetz et al. (Aug. 2000) "3-Deoxy-D-manno-oct-2-ulosonic acid (kdo) transferase of *Legionella pneumophila* transfers two kdo residues to a structurally different lipid A precursor of *Escherichia coli*," *J. Bacteriol*. 182: 4654-4657.
Brandtzaeg et al.(Sep. 1992) "Compartmentalization of lipopolysaccharide production correlates with clinical presentation in meningococcal disease," *J. Infect. Dis*. 166:650-652.
Brozek et al. (Sep. 1990) "Biosynthesis of lipid A in *Escherichia coli*. Acyl carrier protein-dependent incorporation of laurate and myristate," *J. Biol. Chem*. 265:15410-15417.
Christodoulides, et al. (Jan. 2000) "Interaction of Primary Human Endometrial Cells with *Neisseria gonorrhoeae* Expressing Green Flourescent Protein," *Mol. Microbiol*. 35(1):32-43.
Cieslewicz et al. (Dec. 1993) "Cloning, Sequencing, Expression, and Complementation Analysis of the *Escherichia coli* K1 Region 1 Gene, KpsE, and Identification of an Upstream Open Reading Frame Encoding a Protein with Homology to GutQ," *J. Bacteriol*. 175(24):8018-8023.
Cieslewicz et al. (Jun. 1996) "Thermoregulation of *kpsF*, the first region 1 gene in the *kps* locus for polysialic acid biosynthesis in *Escherichia coli* K1," *J. Bacteriol*. 178:3212-20.
Cieslewicz et al. (Oct. 1997) "Reduced polysialic acid capsule expression in *Escherichia coli* K1 mutants with chromosomal defects in *kps*, " *Mol. Microbiol*. 26:237-249.
Finke et al. (Jul. 1991) "Biosynthesis of the *Escherichia coli* K5 polysaccharide, a representative of group II capsular polysaccharides: polymerization in vitro and characterization of the product," *J. Bacteriol*. 173:4088-4094.
Frecer et al. (Feb. 2000) Interpretation of biological activity data of bacterial endotoxins by simple molecular models of mechanism of action, *Eur. J. Biochem*. 267:837-852.

(Continued)

*Primary Examiner*—S. Devi
(74) *Attorney, Agent, or Firm*—Greenlee Sullivan P.C.

(57) ABSTRACT

Provided herein are mutant strains of *Neisseria meningitidis* which produce Kdo-free lipid A as well as the Kdo-free lipid A molecules and immunogenic compositions containing such Kdo-free lipid A molecules from a *Neisseria* strain containing a genetically stable mutation which inactivates a gene selected from the group consisting of genes encoding arabinose-5-phosphate isomerase, CMP-Kdo synthetase and CMP-Kdo transferase. *N. meningitidis* NMB206 is a specifically exemplified strain which harbors a stable insertion mutation in the gene (kpsF) encoding A5P isomerase; strain NMB-249 is a specifically exemplified strain with a stable insertion mutation in the gene (kdtA) encoding CMP-Kdo synthetase, and strain NMB259 is specifically exemplified strain with a stable insertion mutation in the gene (kdsB) encoding CMP-Kdo transferase. Also provided by the present invention are methods for the production of Lipid A flee of 3-keto-3-deoxyoctanoic acid using these genetically stable *N. meningitidis* mutants. Also describes is pYT250, a plasmid functional in neisseriae and in enterics such as *Escherichia coli*.

4 Claims, 18 Drawing Sheets

OTHER PUBLICATIONS

Frecer et al. (Jun. 2000) "Molecular dynamics study on lipid A from *Escherichia coli*: insights into its mechanism of biological action," *Biochim. Biophys. Acta* 1466:87-104.

Galanos et al. (Apr. 1984) "Endotoxic properties of chemically synthesized lipid A part structures. Comparison of synthetic lipid A precursor and synthetic analogues with biosynthetic lipid a precursor and free lipid A," *Eur. J. Biochem.* 140:221-227.

Gangloff et al. (Mar. 1999) "Lipopolysaccharide structure influences the macrophage response via CD14-independent and CD14-dependent pathways," *Clinical Infectious Diseases* 28:491-496.

Goldman et al. (Apr. 1988) "Lipid A precursor from *Pseudomonas aeruginosa* is completely acylated prior to addition of 3-deoxy-D-manno-octulosonate," *J. Biol. Chem.* 263:5217-5223.

Gotschlich et al. (Sep. 1981) "Lipid on capsular polysaccharides of gram-negative bacteria," *J. Biol. Chem.* 256: 8915-21.

Hawkins et al. (Feb. 2002) "A novel class of endotoxin receptor agonists with simplified structure, toll-like receptor 4-dependent immunostimulatory action, and adjuvant activity," *J Pharmacol. Exp. Ther.* 300:655-661.

Hirschfeld et al. (Mar. 2001) "Signaling by Toll-Like Receptor 2 and 4 Agonists Results in Differential Gene Expression in Murine Macrophages" *Infect. Immun.* 69:1477-1482.

Hitchcock et al. (Apr. 1983) "Morphological heterogeneity among *Salmonella* lipopolysaccharide chemotypes in silver-stained polyacrylamide gels," *J. Bacteriol.* 154:269-277.

Kahler et al. (Mar. 1996) "Inner core biosynthesis of lipooligosaccharide (LOS) in *Neisseria meningitidis* serogroup B: identification and role in LOS assembly of the alpha1,2 N-acetylglucosamine transferase (RfaK)," *J. Bacteriol.* 178:1265-1273.

Kahler et al. (Dec. 1998) "The ($\alpha 2 \rightarrow 8$)-linked polysialic acid capsule and lipooligosaccharide structure both contribute to the ability of serogroup B *Neisseria meningitidis* to resist the bactericidal activity of normal human serum," *Infect. Immun.* 66:5939-5947.

Kahler et al. (Jan. 1998) "Genetic basis for biosynthesis, structure, and function of meningococcal lipooligosaccharide (endotoxin)," *Crit. Rev. Microbiol.* 24: 281-334.

Kathariou et al. (May 1990) "Transposition of Tn916 to Different Sites in the Chromosome of *Neisseria meningitidis*: A Genetic Tool for Meningococcal Mutagenesis," *Mol. Microbiol.* 4:729-735.

Levin et al. (Aug. 1996) "Cloning, Complementation, and Characterization of an *rfaE* Homolog from *Neisseria gonorrhoeae*," *J. Bacteriol.* 178(15):4571-4575.

Loppnow et al. (May 1989) "IL-1 induction-capacity of defined lipopolysaccharide partial structures, "*J. Immunol.* 142:3229-3238.

Luderitz et al. (Jul. 1984) "Lipopolysaccharides: structural principles and biologic activities," *Rev. Infect. Dis.* 6:428-431.

MacKinnon et al. (Nov. 1993) "Demonstration of lipooligosaccharide immunotype and capsule as virulence factors for *Neisseria meningitidis* using an infant mouse intranasal infection model," *Microb. Path.* 15:359-366.

Matsuyama et al. (Oct. 2001) "Non-standard biological activities of lipopolysaccharide from *Helicobacter pylori*," *J. Med. Microbiol*, 50:865-869.

Menard et al. (Sep. 1993) "Nonpolar mutagenesis of the *ipa* genes defines IpaB, IpaC, and IpaD as effectors of *Shigella flexneri* entry into epithelial cells," *J. Bacteriol.* 175:5899-5906.

Mohan et al. (Nov. 1994) "Endotoxin biosynthesis in *Pseudomonas aeruginosa*: enzymatic incorporation of laurate before 3-deoxy-D-manno-octulosonate," *J. Bacteriol.* 176:6944-6951.

Moran et al. (Dec. 1996) "Molecular mimicry of host structures by bacterial lipopolysaccharides and its contribution to disease," *FEMS Immunol. Med. Microbiol.* 16:105-115.

Nurminen et al. (May 1985) "Chemical characterization of Chlamydia trachomatis lipopolysaccharide," *Infect. Immun.* 48:573-575.

Odegaard et al. (Aug. 1997) "Shortened hydroxyacyl chains on lipid A of *Escherichia coli* cells expressing a foreign UDP-N-acetylglucosamine O-acyltransferase," *J. Biol. Chem.* 272:19688-19696.

Ogawa et al. (Nov. 2002) "Cell activation by *Porphyromonas gingivalis* lipid A molecule through Toll-like receptor 4- and myeloid differentiation factor 88-dependent signaling pathway," *Int. Immunol.* 14:1325-1332.

Pazzani et al. (Sep. 1993) "Molecular analysis of region 1 of the *Escherichia coli* K5 antigen gene cluster: a region encoding proteins involved in cell surface expression of capsular polysaccharide," *J. Bacteriol.* 175:5978-5983.

Plotz et al. (Apr. 2000) "Characterization of a novel lipid a containing D-galacturonic acid that replaces phosphate residues. The structure of the lipid A of the lipopolysaccharide from the hyperthermophilic bacterium *Aquifex pyrophilus*," *J. Biol. Chem.* 275:11222-11228.

Porat et al. (Jun. 1995) "A lipooligosaccharide-binding site on HepG2 cells similar to the gonococcal opacity-associated surface protein Opa," *Infect. Immun.* 63:2164-2172.

Prentki et al. (Sep. 1984) "In vitro insertional mutagenesis with a selectable DNA fragment," *Gene* 29:303-313.

Raetz, C.R.H. (1996) "Bacterial lipopolysaccharides: a remarkable family of bioactive macroamphiphiles. In Neidhardt, F.C. (ed.) *Escherichia coli and Salmonella: Cellular and Molecular Biology*," American Society for Microbiology, Washington, D.C., vol. 1, pp. 1035-1063.

Rahman et al. (Feb. 1998) "The lipooligosaccharide (LOS) of *Neisseria meningitidis* serogroup B strain NMB contains L2, L3, and novel oligosaccharides, and lacks the lipid-A 4'-phosphate substituent," *Carbohydr. Res.* 307:311-324.

Rietschel et al. (Feb. 1994) "Bacterial endotoxin: molecular relationships of structure to activity and function," *FASEB J.* 8:217-225.

Rosenow et al. (Jan. 1995) "Isolation from recombinant *Escherichia coli* and characterization of CMP-Kdo synthetase, involved in the expression of the capsular K5 polysaccharide (K-CKS)," *FEMS Microbiol. Letts.* 125:159-164.

Rund et al. (Jun. 1999) "Structural analysis of the lipopolysaccharide from *Chlamydia trachomatis* serotype L2," *J. Biol. Chem.* 274:16819-16824.

Salimath et al. (Oct. 1983) "Structural studies on the non-toxic lipid A from *Rhodopseudomonas sphaeroides* ATCC 17023," *Eur. J. Biochem.* 136:195-200.

Schromm et al. (Nov. 1998) "The charge of endotoxin molecules influences their conformation and IL- 6-inducing capacity," *J. Immunol.* 161:5464-5471.

Seydel et al. (May 2000) "Intrinsic conformation of lipid A is responsible for agonistic and antagonistic activity," *Eur. J. Biochem.* 267:3032-3039.

Shafer et al. (Feb. 1984) "Serum sensitivity of *Neisseria gonorrhoeae*: the role of lipopolysaccharide," *J. Infect. Dis.* 149:179-183.

Simpson et al. (Nov. 1996) "Transcriptional organization and regulation of expression of region 1 of the *Escherichia coli* K5 capsule gene cluster," *J. Bacteriol.* 178:6466-6474.

Steeghs et al. (Apr. 1998) "Meningitis bacterium is viable without endotoxin," *Nature* 392:449-450.

Stephens et al. (Feb. 1993) "Effect of the ($\alpha 2 \rightarrow \alpha 8$)-linked polysialic acid capsule on adherence of *Neisseria meningitidis* to human mucosal cells," *J. Infect. Dis.* 167:475-479.

Stephens et al. (Nov. 1991) "Insertion of Tn916 in *Neisseria meningitidis* resulting in loss of group B capsular polysaccharide," *Infect. Immun.* 59:4097-4102.

Stephens et al. (Jul. 1994) "Tn916-Generated, Lipooligosaccharide Mutants of *Neisseria meningitides* and *Neisseria gonorrhoeae*," *Infect. Immun.* 62:2947-2952.

Suda et al. (Jan. 2001) "Chemical structure and biological activity of a lipid A component from *Helicobacter pylori* strain 206," *J. Endotoxin Res.* 7:95-104.

Swartley et al. (Jul. 1996) "Expression of sialic acid and polysialic acid in serogroup B *Neisseria meningitidis*: divergent transcription of biosynthesis and transport operons through a common promoter region," *J. Bacteriol.* 178:4052-4059.

Swartley et al. (Mar. 1998) "Characterization of the gene cassette required for biosynthesis of the ($\alpha 1 \rightarrow 6$)-linked N-acetyl-D- mannosamine-1-phosphate capsule of serogroup A *Neisseria meningitidi*,". *J Bacteriol.* 180:1533-1539.

Swartley et al. (Jan. 1997) "Capsule switching of *Neisseria meningitidis*," *Proc. Natl. Acad. Sci. USA* 94:271-276.

Tanamoto et al. (Mar. 2000) "Salmonella-type heptaacylated lipid A is inactive and acts as an antagonist of lipopolysaccharide action on human line cells," *J. Immunol.* 164:3149-3156.

Tettelin et al. (Mar. 2000) "Complete genome sequence of *Neisseria meningitidis* serogroup B strain MC58," *Science* 287:1809-1815.

Tzeng et al. (May 2002) "Endotoxin of *Neisseria meningitides* Composed Only of Intact Lipid A: Inactivation of the Meningococcal 3-Deoxy-D-Manno-Octulosonic Acid Transferase," *J. Bacteriol.* 184(9):2379-2388.

Tzeng et al. (Jul. 2002) "KpsF is the Arabinose-5-phosphate Isomerase Required for 3-Deoxy-D-manno-octulosonic Acid Biosynthesis and for Both Lipooligosaccharide Assembly and Capsular Polysaccharide Expression in *Neisseria meningitidis*," *J. Biol. Chem* 227(27):24103-24113.

Tzeng et al. (2000) "Epidemiology and pathogenesis of *Neisseria meningitidis*," *Microbes Infect.* 2: 687-700.

Tzeng et al. (Apr. 2001) "Transcriptional regulation of divergent capsule biosynthesis and transport operon promoters in serogroup B *Neisseria meningitidis,* "*Infect. Immun.* 69:2502-2511.

Van Der Ley et al.(Oct. 2001) "Modification of lipid A biosynthesis in *Neisseria meningitidis lpxL* mutants: influence on lipopolysaccharide structure, toxicity, and adjuvant activity," *Infect. Immun.* 69:5981-5990.

Vimr et al. (Nov. 1985) "Regulation of sialic acid metabolism in *Escherichia coli*: role of N-acylneuraminate pyruvate-lyase," *J. Bacteriol.* 164:854-860.

Yamada et al. (Jan. 1990) "Nucleotide sequence and expression of the *gutQ* gene within the glucitol operon of *Escherichia coli*," *DNA Seq.* 1:141-145.

Yoshizaki et al. (2001) "First Total Synthesis of the Re-Type Lipopolysaccharide," *Angew. Chem. Int. Ed.* 40:1475-1480.

Zahringer et al.(Jan. 1995) "The lipopolysaccharide of *Legionella pneumophila* serogroup 1 (strain Philadelphia 1): chemical structure and biological significance," in Bacterial Endotoxins: Lipopolysaccharides from Genes to Therapy, pp. 113-139, Wiley-Liss, Inc.

Zhou et al. (May 1996) "Plasmids with erythromycin resistance and catechol 2,3-dioxygenase- or beta-galactosidase-encoding gene cassettes for use in Neisseria spp," *Gene* 171:133-134.

Zhou et al. (May 1998) "Function of Escherichia coli MsbA, an essential ABC family transporter, in lipid A and phospholipid biosynthesis," *J. Biol. Chem.* 273:12466-12475.

\* cited by examiner

*N. meningitidis-B*

*E. coli-K1(5)*

```
NMB0352  ------------------------------MAENGKYLDWAREVLHAEAEGLREIAAELD-KNFVLAA
NMA2135  ------------------------------MAGNEKYLDWAREVLHTEAEGLREIAADLD-ENFALAA
KpsF-K1  ---MSERHLPD-DQSSTIDPYLITS------VRQTLAEEGARLQNLSKQLDSGQYQRVL
YrbH     ------------MSHVELQPGFDFQQAGKEVLAIERECLAELDQYIN-QNFTLAC
GutQ     ------------------------------MLELQEASRLPERLG-DDFVRAA
                                          *      :  ::      .

Walker A
                         ━━━━━━━━━━━━━━━
NMB0352  DALLHCKGRVVITGMGKSGHIGRKMAATMASTGTPAFFVHPAEAAHGDLGMIVDNDVVVA
NMA2135  DALLHCKGRVVITGMGKSGHIGRKMAATMASTGTPAFFVHPAEAAHGDLGMIVDNDVVVA
KpsF-K1  NLIMNCKGHVILSGMGKSGHVGRKMSATLASTGTPSFFIHPAEAPHGDLGMITPYDLLIL
YrbH     EKMFWCKGKVVVMGMGKSGHIGRKMAATFASTGTPSFFVHPGEAAHGDLGMVTPQDVVIA
GutQ     NIILHCEGKVVVSGIGKSGHIGKKIAATLASTGTPAFFVHPAEALHGDLGMIESRDVMLF
           :  * :***  :**.*****  **  ****.*:******** * ::****:   *::

NMB0352  ISNSGESDEIAAIIPALKRKDITLVCITARPDSTMARHADIHITASVSKEACPLGLAPTT
NMA2135  ISNSGESDEIAAIIPALKRKDITLVCITARPDSTMARHADIHITASVSKEACPLGLAPTT
KpsF-K1  ISASGETDEILKLVPSLKNFGNRIIAITNNGNSTLAKNADAVLELHMANETCPNNLAPTT
YrbH     ISNSGESSEITALIPVLKRLHVPLICITGRPESSMARAADVHLCVKVAKEACPLGLAPTS
GutQ     ISYSGGAKELDLIIPRLEDKSIALLAMTGKPTSPLGLAAKAVLDISVEREACPMHLAPTS
         **  *  .:: :::*.::. . :  **. . :   *:   .  .:. :::  * ::***:

NMB0352  STTAVMALGDALAVVLLRARAFTPDDFALSHPAGSLGKRLLLRVADIMHKGGGLPAVRLG
NMA2135  STTAVMALGDALAVVLLRARAFTPDDFALSHPAGSLGKRLLLRVADIMHKGGGLPAVRLG
KpsF-K1  STTLTMAIGDALAIAMIRQRKFMPNDFARYHPGGSLGRRLLTRVADVMQHD--VPAVQLD
YrbH     STTATLVMGDALAVALLKARGFTAEDFALSHPGGALGRKLLLRVNDIMHTGDEIPHVKKT
GutQ     STVNTLMGDALAMAVMQARGFNEEDFARSHPAGALGARLLNKVHHLMRRDDAIPQVALT
         **  .:  ****:  : :*  *  :**  **.*:**..:** :* .:*:        :

NMB0352  TPLKEAIVSMSEKGLGMLAVTDGQGRLKGVFTDGDLRRLF-QECDNPFTGLSIDEVMHTHP
NMA2135  TPLKEAIVSMSEKGLGMLAVTDGQGRLKGVFTDGDLRRLF-QECDNPFTGLSIDEVMHTHP
KpsF-K1  ASFKTVIQRITSGCQGMVMVEDAEGGLAGIITDGDLRRFMEKEDS-LTSATAAQMMTREP
YrbH     ASLRDALLEVTRKNLGMTVICDDNMIEGIFTDGDLRRVF-DMGVDVRQLSIADVMTPGG
GutQ     ASVMDAMLELSRTGLGLVAVCDAQQQVQGVFTDGDLRRWL-VGGGALT-TPVNEAMTVGG
         :..   :   : :  *:  .      *::**********:           .  .  .*

NMB0352  KTISAERLATEALKVMQANHVNGLLVTDADGVLIGALNMHDLLAARIV
NMA2135  KTISAERLATEALKVMQANHVNGLLVTDADGVLIGALNMHDLLAARIV
KpsF-K1  LTLPEDTMIIEAEEKMQKHRVSTLLVTNKANKVTGLVRIFD------
YrbH     IRVRPGILAVEALNLMQSRHITSVMVADGD-HLLGVLHMHDLLRAGVV
GutQ     TTLQSQSRAIDAKEILMKRKITAAPVVDENGKLTGAINLQDFYQAGII
         :    . .   *:::* .:  :   .:*  ::.  : :.:  .. :
```

FIG. 2

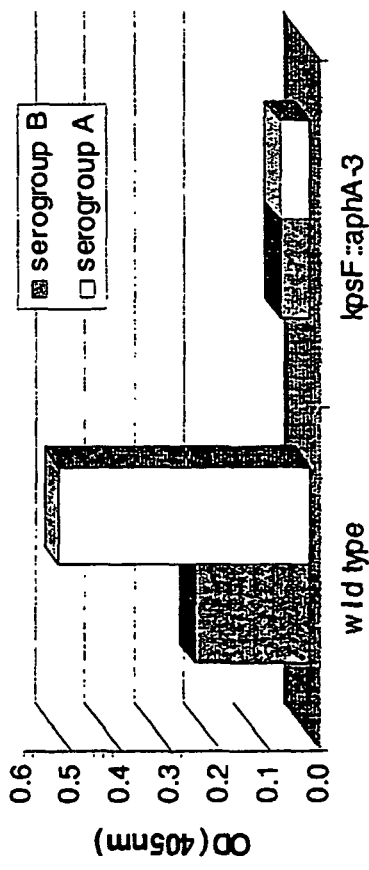
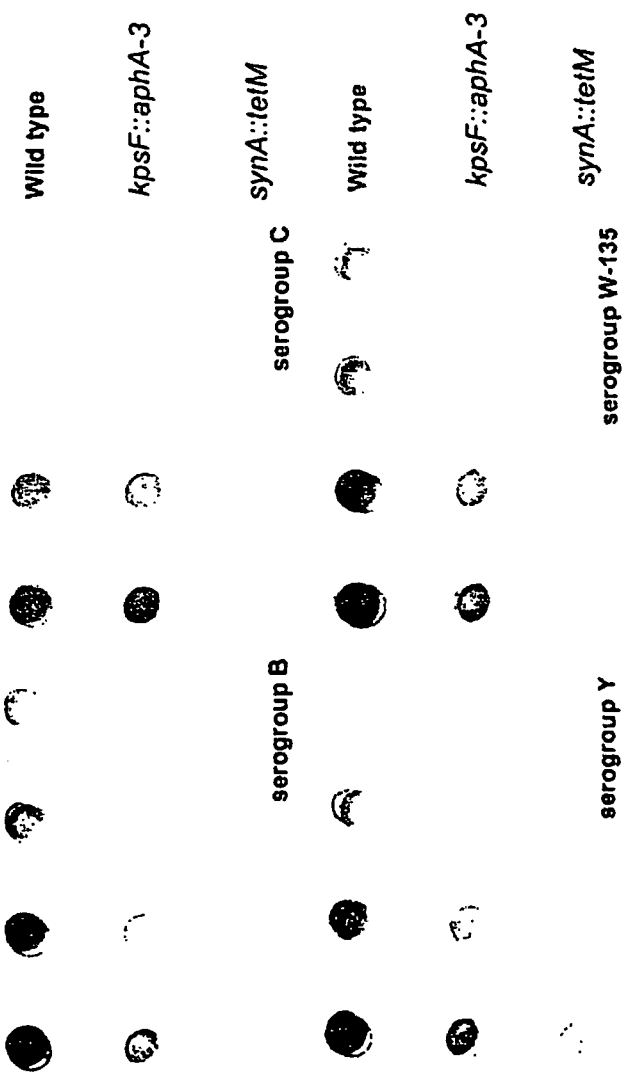
FIG. 3A
FIG. 3B

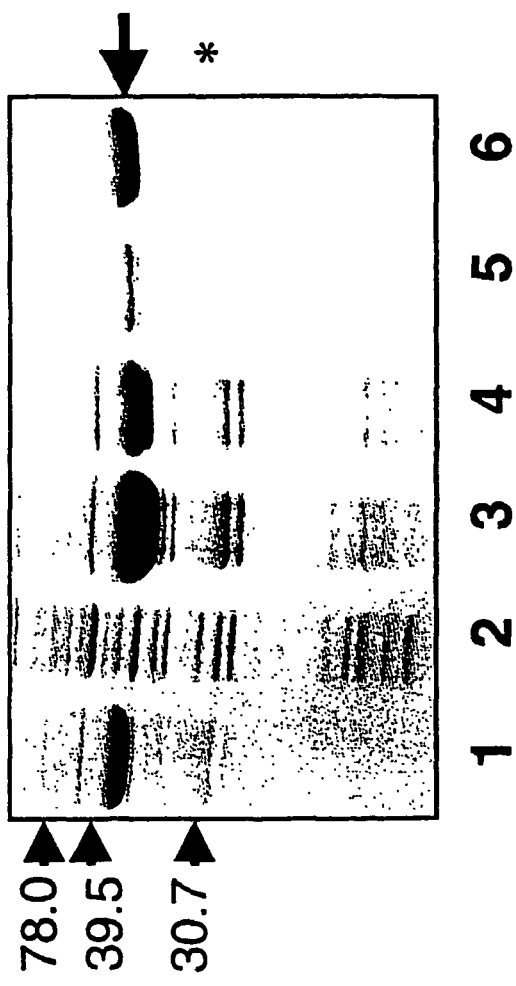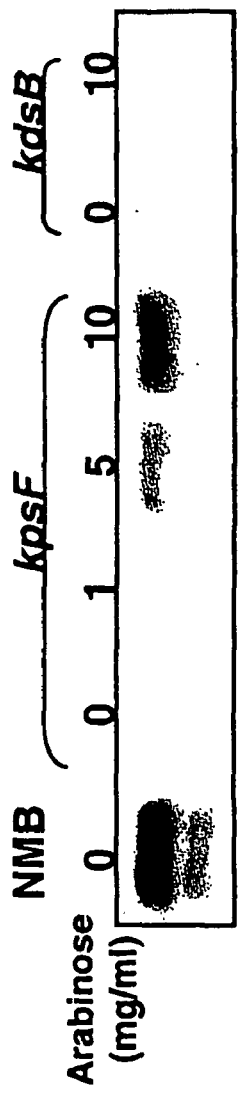
FIG. 9A
FIG. 9B

Mass
1837
1757
1714
1634

8NEISSERIA MUTANTS, LIPOOLIGOSACCHARIDES AND IMMUNOGENIC COMPOSITIONS

CROSS-REFERENCE TO RELATED APPLICATIONS

This application is a national phase application of Patent Cooperation International Application PCT/US03/08795, filed 20 Mar. 2003, which application claims benefit of U.S. Provisional Application No. 60/366,060, filed Mar. 20, 2002. It is incorporated by reference herein.

ACKNOWLEDGMENT OF FEDERAL RESEARCH SUPPORT

This invention was made, at least in part, with funding from the United States National Institute of Allergy and Infectious Diseases. (Grant No. AI-33517). Accordingly, the United States Government has certain rights in this invention.

BACKGROUND OF THE INVENTION

The field of this invention is the area of bacterial genetics, lipooligosaccharide biosynthesis, vaccines and lipid A-containing compositions, and in particular, as related to *Neisseria meningitidis*.

*Neisseria meningitidis* and *Neisseria gonorrhoeae* are important human pathogens. *N. meningitidis* causes meningitis, sepsis and bacteremia; *N. gonorrhoeae* causes gonorrhea in both sexes, pelvic inflammatory disease and/or sterility in women, and rectal and pharyngeal infections, as in homosexual men. More rarely, disseminated gonococcal infection (gonococcal bacteremia) can result, with complications such as polyarthralgias or purulent arthritis, for example. These two species are relatively closely related genetically; there is approximately 85% DNA sequence homology between the genomes of the two species. The genus also includes several other species which are nonpathogenic to man although they colonize the upper respiratory tract.

*Neisseria* produce lipooligosaccharide (LOS) which is associated with the bacterial outer membrane. The lipooligosaccharide differs from the lipopolysaccharide (LPS) of the *Enterobacteriaceae* in that they are short, often branched sugar chains rather than relatively long repeating subunits. Neisserial LOS is classified into six serotypes among the gonococci and into thirteen in the meningococci. Neisserial LOS contain glucose, galactose, 2-keto-3-deoxyoctonic acid (Kdo), glucosamine, galactosamine, sialic acid and ethanolamine in ratios and linkages which depend on the serotype. LOS molecules produced by wild-type strains generally have molecular masses in the range of about 3200 to about 7000 d, as estimated by sodium dodecyl sulfate polyacrylamide gel electrophoresis (SDS PAGE). The short, often branched oligosaccharide chains are attached via Kdo to lipid A embedded in the outer membrane. The LOS structure of a particular strain is subject to antigenic variation.

Lipid A of the neisseriae acts as a classic endotoxin and can induce changes in the permeability of the blood brain barrier after invasion of the cerebrospinal fluid during meningococcemia (Tunkel and Scheld (1993) *Clin. Res. Microbiol.* 6, 118-136). The composition of the LOS influences the invasive capacity of the meningococci (MacKinnon et al. (1993) *Microb. Path.* 15, 359-366) and in the gonococci as well as the meningococci, the composition of the LOS affects the susceptibility of the bacterial cells to normal human serum (Shafer et al. (1984) *J. Infec. Dis.* 149, 179-183; Porat et al. (1995) *Infect. Immun.* 63:2164-2172).

The morbidity and mortality of meningococcal bacteremia and meningitis have been directly correlated with the amount of circulating meningococcal endotoxin (lipopoly[oligo]saccharide or LOS) (van Deuren, 2000; Brandtzaeg, 1989; Brandtzaeg, 1992). The engagement of meningococcal LOS with the human toll-like receptor 4 (TLR4) on human macrophages and other host cells is proposed to trigger signaling events that ultimately result in cytokine gene activation and the production of proinflammatory cytokines and chemokines. Meningococcemia and meningococcal meningitis are predicted in large part to be a direct result of the over-stimulation of TLR4 activation by circulating meningococcal LOS (Brandtzaeg, 1989; Brandtzaeg, 1992; Brandtzaeg, 1995) inducing a cascade of events that lead clinically to hypotension, organ failure, necrosis, coma and death. However, the mechanism by which meningococcal LOS activates TLR4 to produce fulminant meningococcemia and meningitis is not understood.

*Neisseria meningitidis*, an exclusive human pathogen, is a cause of bacterial meningitis and sepsis, and infection can result in epidemic as well as endemic disease. Capsular polysaccharides and lipooligosaccharide (LOS) are two critical virulence factors in meningococcal pathogenesis (Tzeng and Stephens, 2000), contributing to the resistance of meningococci to serum bactericidal activity (Kahler et al., 1998). Capsular polysaccharides protect meningococci from host immune defenses, including phagocytosis, opsonization and complement-mediated killing (Jarvis, 1995; Troy, 1992). Capsule also protects meningococci from environmental stress such as desiccation and facilitates transmission due to its anti-adherence properties (Stephens and McGee, 1981; Stephens et al., 1993; Virji et al, 1993). Mimicry by LOS structure of the carbohydrate moieties of glycosphingolipids present in many human cells (Estabrook et al., 1997; Moran et al., 1996) further enables meningococci to escape bactericidal antibody recognition.

Structural differences in capsule and LOS are the determinants in the serological typing of meningococcal serogroups and immunotypes respectively. Of the thirteen different capsule serogroups so far defined, five (serogroups A, B, C, Y, and W-135) are associated with invasive meningococcal disease. Serogroup A capsule is ($\alpha 1 \rightarrow 6$) linked N-acetyl mannosamine 1-phosphate; serogroup B capsule is composed of ($\alpha 2 \rightarrow 8$) linked N-acetylneuraminic acid (NANA); serogroup C capsule is ($\alpha 2 \rightarrow 9$) linked partially O-acetylated NANA; serogroup Y capsule is an alternating sequence of D-glucose and partially O-acetylated NANA; and serogroup W-135 capsule is composed of alternating sequence of D-galactose and NANA. Meningococcal LOS consists of lipid A, a conserved inner core composed of two heptoses linked to two 3-deoxy-D-manno-2-octulosonic acid moieties (Kdo), and an outer core with variable oligosaccharide composition. The meningococcal lipid A is distinct from that of *E. coli*; it is composed of a $\beta 1'$, 6-linked disaccharide of glucosamine acetylated with $\beta$-hydroxymyristates and $\beta$-hydroxylaurates at the 2, 2' and 3, 3' positions, respectively, and symmetrical acyloxyacyl linkages of laurate residues are located at the 2, 2' positions (Rahman et al., 1998).

More than thirty genes involved in the biosynthesis of lipid A, heptose, Kdo and the outer core polysaccharides have been identified (Kahler and Stephens, 1998) The capsule biosynthetic pathway has also been studied extensively. A four-gene operon (synABCD) mediates the production of sialic acid and the formation of capsule polymers; while the divergently transcribed ctrABCD operon encodes the proteins responsible for capsule translocation (Swartley et al., 1996). No genes outside the capsule locus have been shown, as yet, to participate in capsule expression.

E. coli K1 strains also express a capsule composed of (α2→8) linked polysialic acid. The capsule locus of K1 E. coli has also been well characterized, and when compared to the meningococcal capsule locus (FIG. 1A), it contains several "extra" genes including kpsF, kpsD, kpsU, neuD and neuE. KpsU has been shown to encode a second copy of the CMP-Kdo synthetase, KdsB (Rosenow et al., 1995). KpsD is a periplasmic protein, and mutation of kpsD resulted in periplasmic polysaccharide. The functions of KpsF, NeuD and NeuE are currently unknown. Prior to the present invention, it was not known if these genes were present in meningococci.

There is a long felt need in the art for a protective vaccine effective in the prevention of human diseases caused by the pathogenic Neisseria species, N. gonorrhoeae and N. meningitidis, especially Group B meningococci. Meningococcal meningitis or meningococcemia can have about 85% mortality if untreated and about 10-20% if treated, and individuals with deficiencies in late complement cascade components C5, C6, C7 and C8 appear to be prone to multiple episodes of meningococcal meningitidis. For example, nonpathogenic strains or antigenic material therefrom, particularly those which lack intact lipooligosaccharide (LOS) structure, as antigen for preparing antibodies specific to this bacterial surface component or for attenuated vaccines useful in protection against the diseases resulting from infection with Neisseria species. There is also a need in the art for Lipid A-producing strains of bacteria, where the purification and preparation of lipid A is simplified in comparison to preparation from enteric bacteria or neisseriae with intact LOS.

SUMMARY OF THE INVENTION

An object of the present invention is to provide genetically stable, mutant strains of Neisseria which produce lipid A free of Dko and oligosaccharides characteristic of neisserial LOS. N. meningitidis strain deficient in the expression of arabinose 5-phosphate isomerase, CMP-Kdo synthetase or CMp-Kdo transferase produce lipid A which is free of Kdo. As specifically exemplified herein, these genetically stable, nonpolar mutants are made by inserting an aphA-3 kanamycin resistance marker in the kpsF, kdsB or kdtA gene, respectively, to inactivate those genes. Specifically, exemplified mutants are N. meningitidis strains NMB206, NMB259 and NMB249, respectively. Other ways to generate stable mutations include producing a deletion or multiple point mutations in a target gene and certain other selectable markers which can be inserted. PCR is a useful, readily accessible methodology for introducing mutations at predetermined sites in target genetic material. The mutation which inactivates the kpsF gene should be nonpolar; desirably mutations which inactivate kdtA and kdsB are nonpolar.

The present invention further provides Kdo-free lipid A preparations made by extracting lipid A from cells of *Neisseria* strains in-which the function of the kpsF, kdsB, or kdtA gene has been inactivated. Kdo-free lipid A is useful as a standard in quality control testing for pharmaceutical and cosmetic manufacturing, or as an immunological adjuvant in immunogenic compositions.

It is an additional object of the present invention to provide a vector functional in both enteric bacteria such as *Escherichia coli* and in neisserial species, especially *Neisseria meningitidis*. The vector specifically disclosed herein is pYT250 (see FIG. 15).

Deposited Biological Material

Applicants have deposited samples of *Neisseria meningitidis* NMB206, *Neisseria meningitidis* NMB249, *Neisseria meningitidis* NMB259 and *Escherichia coli* K-12 DH5-alpha/pYT250 with the American Type Culture Collection (ATCC), 10801 University Boulevard, Manassas, Va. 20110-2700 on Feb. 14, 2002, in accordance with the provisions of the Budapest Treaty, and these strains have been assigned the following identification numbers: PTA-4080, PTA-4081, PTA-4082, and PTA-4079, respectively. Each of these strain deposits will be maintained without restriction in the ATCC depository for a period of 30 years, or 5 years after the last request, or for the effective life of the patent, whichever is longer, and will be replaced if the deposit becomes non-viable during that period.

BRIEF DESCRIPTION OF THE DRAWINGS

FIGS. 1A-1*c* characterize the relevant portions of the *N. meningitidis* genome. FIG. 1A shows the genetic organization of the meningococcal and *E. coli* K1 capsule loci. Homologous genes are colored in gray. FIG. 1B provides a primer map of meningococcal kpsF locus. In *N. meningitidis* a 96 bp intergenic region separates the divergently transcribed tal and kpsF. Restriction sites used in generating insertional mutations are also labeled. FIG. 1C presents the genetic organization of kdtA locus in the meningococcal MC58 and Z2491 genomes. lpxC: UDP-3-O-3-hydroxymyristoyl-acetylglucosamine deacetylase (lipid A biosynthesis); gnd6 phosphogluconate dehydrogenase (pentose phosphate pathway): murA, UDP-N-acetylglucosamine 1-carboxyvinyl-transferase (peptidoglycan biosynthesis): HP, hypothetical protein. The locations of primers YT81 and YT82 (see Table 2) are also indicated.

FIG. 2 depicts protein sequence alignment of KpsF homologues prepared using the CLUSTAL W method. The SIS domain is indicated with a black line above the sequence and a thick black bar labeled the location of the Walker A box. The amino acid sequences for NMB0352, NMB2135, KpsF-K1, YrbH and GutQ are given in SEQ ID NOs:32-35.

FIGS. 3A-3B illustrate the results of whole cell ELISAs and whole cell immunodot blots of kpsF nonpolar mutants. FIG. 3A shows surface expressed capsule of strains F8239 (serogroup A) and NMB (serogroup B) and corresponding kpsF mutants were measured by ELISA. FIG. 3B shows the results obtained using serial dilutions of whole bacteria (from left to right: $1\times10^7$, $5\times10^6$, $1\times10^6$, $5\times10^5$) spotted onto a nitrocellulose membrane. the membranes were immunoblotted with corresponding capsule-specific antibodies.

FIG. 4 shows the results of silver-stained Tricine SDS-PAGE of extracted LOS from the wild type (lanes, 1, 3, 5, 7, 9) and the kpsF mutant NMB206 (lanes, 2, 4, 6, 8, 10). The molecular weight markers are labeled on the left. The crude extracts from EDTA/TEA extraction before (lanes 7 and 8) and after (lanes 9 and 10) proteinase K treatment are shown for comparison.

FIGS. 5A-5B characterize the LOS structure of the meningococcal kpsF mutant. FIG. 5A shows a MALDI-TOF mass trace of the purified LOS from the kpsF mutant, and FIG. 5B shows the MALDI-TOF trace after removal of phosphate substituents with aqueous HF. the spectra were collected in the negative (FIG. 5A) and in the positive (FIG. 5B) modes.

FIG. 6A-6D are electron micrographs of thin-sections of the wild type strain (FIG. 6A) and the kpsF mutant (FIGS. 6B, 6C and 6D). When compared to the wild type, kpsF mutant showed the unusual thickened septum and existed as diplococci, tetracocci and clusters.

FIGS. 7A-7D illustrate the results of complementation of kpsF mutation by K1 kpsF. FIG. 7A is a Western immunoblot carried out with Flag tag specific monoclonal antibody. FIG. 7B is a Western blot developed with KpsF-specific antiserum. FIG. 7C shows the results of a Silver-stained Tricine SDS-PAGE of proteinase K digested whole cell lysate. FIG. 7D shows the results of whole cell capsule ELISA. Meningococcal strains are 1) wild type parent strain, NMB; 2) strain 206 (kpsF::aphA-3); 3) strain 240 (Ptac::K1-kpsF) induced with IPTG; 4) strain 240/206 (Ptac,::K1-kpsF, kpsF::aphA-3) induced with IPTG; 5) strain 240 without IPTG; 6) strain 240/206 without IPTG; 7) strain 250 (vector control); 8) strain 250/206 (vector control with 4sF.:aphA-3). Data in FIG. 7D are normalized to the reading of the wild type strain and are the average values of at least three independent experiments are shown.

FIG. 8 illustrates a whole cell capsule ELISA of the wild type strain NMB and its mutants: NMB 206 (cpsF::aphA-3), NMB 249 (kdt,::aphA-3) and NMB 259 (cdsB8::aphA-3). The $OD_{540}$ reading of the wild type strain was normalized to 100% ($n^3 3$).

FIG. 9A illustrates a Coomassie blue stained SDS-PAGE of KpsF purification. Lane 1) induced whole cell, 2) non-induced whole cell, 3) total cleared cell lysate, 4) flow through of Ni—NTA column, 5) 20 mM imidazole wash, 6) 250 mM imidazole eluate. The arrowhead on the right indicates the position of KpsF protein, and the smaller protein band ('i') was identified as a degradation product of KpsF because it reacted with antiserum against KpsF. Molecular weight in KD is labeled on the left. FIG. 9B illustrates a silver-stained Tricine SDS-PAGE of LOS extracted from the NMB206 mutant exogenously complemented with arabinose. FIG. 9C provides $^{31}P$ spectra of the A5P isomerase reaction starting with either A5P (a-c) or Ru5P (d-f) as substrates. Spectra (a), (b), and (c) were taken at t 0, t=54 min, and t=250 mm, respectively, with only A5P (68=4.9 ppm) present at t=0 min (a). Spectra (f), (e), and (d) were taken at t=0, t=180 min, and t=600 min, respectively, with only Ru5P (685.3 ppm present at t=0 min (t). Note that spectra (c) and (d) represent equilibrium approached from either substrate and that the equilibrium ratio of A5P to Ru5P (65:35) is the same in either case.

FIG. 10 summarizes the biosynthetic pathway of CMP-Kdo.

Figure 14:
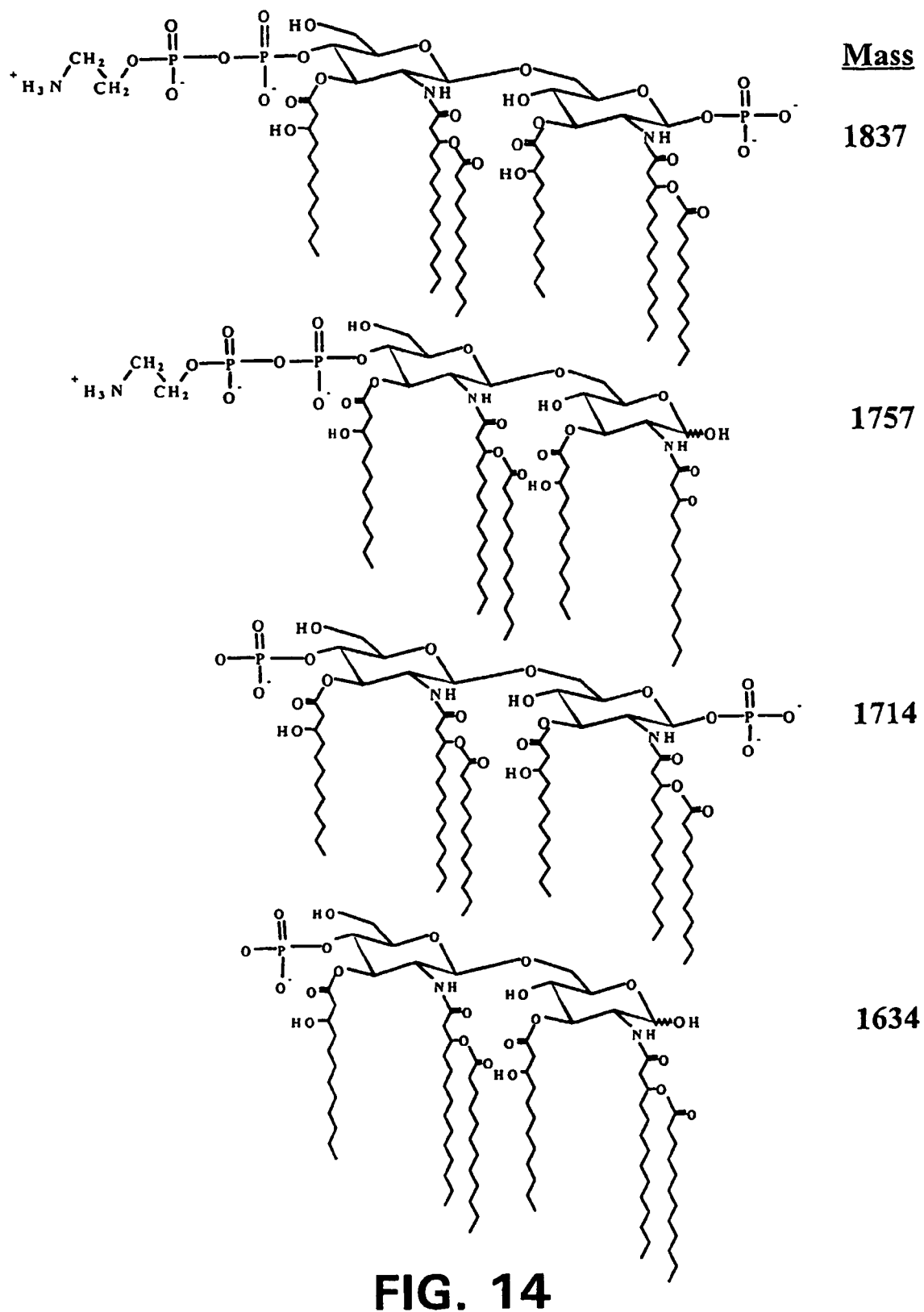

FIG. 14 summarizes the structures of the various lipid A molecules isolated from NMB249.

Figure 15:
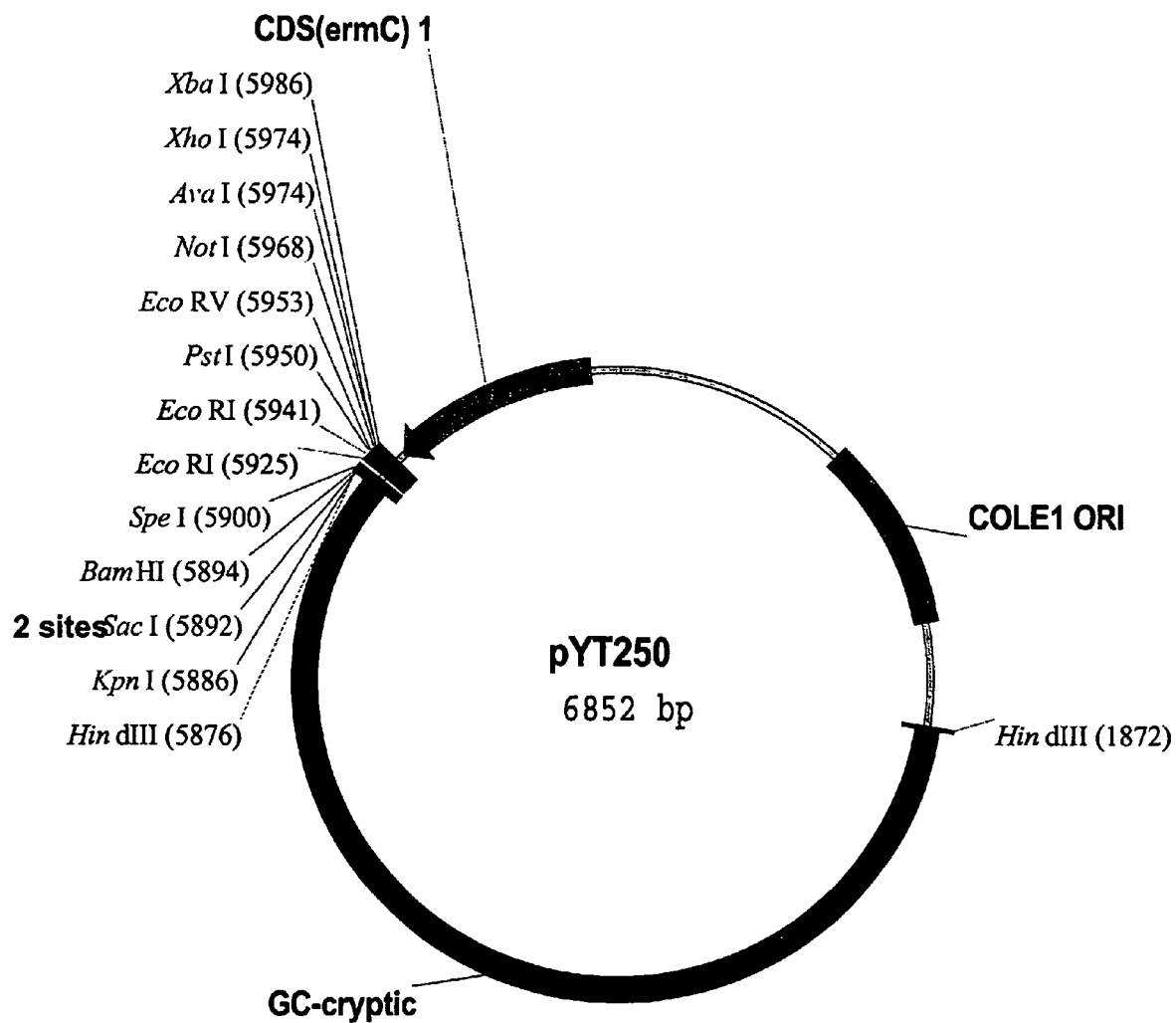

FIG. 15 is a restriction map of the *E. coli/Neisseria* shuttle vector pYT250.

DETAILED DESCRIPTION OF THE INVENTION

Abbreviations used herein for lipooligosaccharide components and for other scientific terms are standard in the art: X represents a sugar residue that has not yet been identified but may be any sugar residue including but not limited to phosphorylated sugars, amino sugars and acetylated sugars and sugar acids. The abbreviations for sugar residues as used herein are as follows: Gal, galactose; Glc, glucose; GlcNAc, N-acetylglucosamine; Kdo, 2-keto-3-deoxyoctonic acid, 3-keto-3-deoxyoctanoic acid, 3-keto-2-deoxyoctulosonic acid; Hep, heptose; NANA, N-acetylneuraminic acid, sialic acid; Erm, erythromycin; Kan, kanamycin; EM, electron microscopy; NBT-BCIP, nitroblue tetrazolium-5-bromo-4-chloro-3-indolylphosphate; GLC, gas liquid chromatography; BSA, bovine serum albumin.

Lipooligosaccharide (LOS) is the term given to the lipopolysaccharide of *Neisseria* species. Unlike the lipopolysaccharide of the *Enterobacteriaceae*, LOS comprises relatively short oligosaccharides linked to the lipid A moiety. The structure of complete (i.e., wild-type) *N. meningitidis* LOS is given in FIG. 1. In nature this LOS is produced by pathogenic strains of *N. meningitidis, N. gonorrhoeae* and certain strains of *Haemophilus influenzae*. It can be purified from cells of wild-type or desired mutant strains or as a recombinant expression product using the genetically modified strains of *N. gonorrhoeae* or *N. meningitidis*. Wild-type LOS of *N. meningitidis* NMB exhibits an apparent molecular mass of about 4.6 kDa, as determined by SDS PAGE. The structure is given in FIG. 1. It reacts with monoclonal antibody 3F11, which is specific for the lacto-N-neotetraose moiety distal to the cell surface.

A chemically synthesized LOS or lipid A molecule is considered an "isolated" LOS preparation, as is an LOS preparation purified from cells provided that the LOS has been freed of contaminating and/or toxic cellular components and products.

Lipid A free of Kdo can be obtained by culturing mutant *N. meningitidis* cells with defects in Psf, KdtA or KdsB which direct the synthesis of a lipid A lacking covalently attached sugars or sugar acids. Lipid A free of sugars and sugar acids is produced using strains of *N. meningitidis* in which a genetically stable mutation has been introduced in psf, kdsB, or kdtA. As specifically exemplified herein, the genetically stable, nonpolar insertion mutation is made using PCR amplification to generate an aphA-3 insertion in the target gene. Other techniques for making stable nonpolar mutations in these genes are readily accessible to the skilled artisan.

Within the present context, genetically stable means that a mutant does not revert to the wild-type phenotype at a significant frequency, preferably reversion occurs at a frequency of less than $10^{-6}$, preferably $10^{-8}$, and more preferably at a frequency of less than $10^{-10}$.

A null mutation in a particular gene is one in which no functional gene product is produced. Such a null mutation can be the result of an interruption in the coding sequence, one or more changes in the amino acid sequence such that any polypeptide synthesized therefrom does not have the function of the wild-type counterpart or it may be the result of an interruption or change in the transcriptional control sequences controlling the expression of the gene.

Figure 1A:
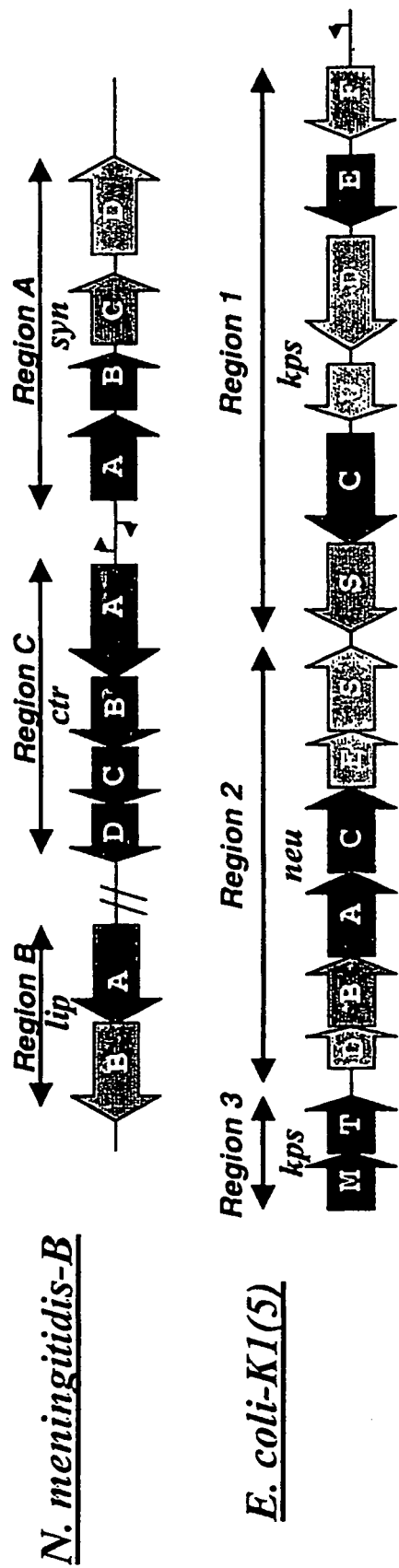
Figure 1B:
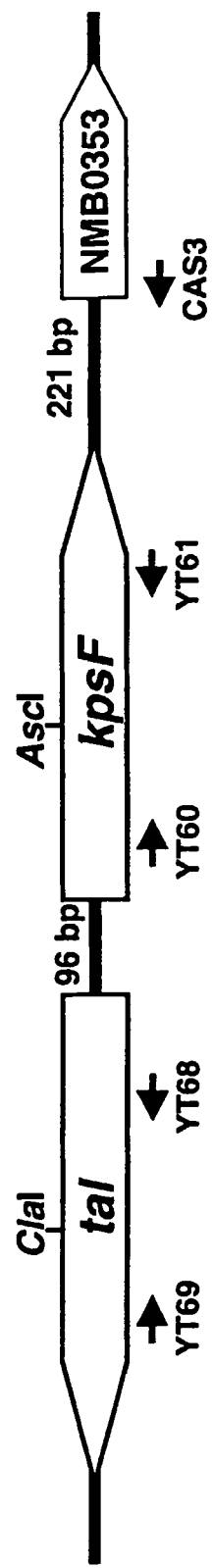

The first gene of region 1 of the *E. coli* K1 cps locus, psf, is not present in the meningococcal cps locus. A search of the complete serogroup B (MC58) and A (Z2941) genome data-bases with the K1 Psf protein sequence revealed a single highly homologous gene (about 64% amino acid identity) in each genome, NMB0352 and NMA2135, respectively. In contrast to K1 *E. coli*, the psf homologues in both neisserial genomes were not associated with the capsule locus. A divergently transcribed gene encoding a putative transaldolase (tal) was located 96 bp upstream of the psf homologue, and a 221 bp intergenic space separated psf from a downstream conserved hypothetical protein (FIG. 1). NMB0352 was predicted to encode a 34 kDa protein of 324 residues and to be a cytoplasmic soluble protein by topology prediction programs (TopPredII and Psort). The NMA2135 homologue of the serogroup A genome was in an identical organization to that of NMB0352 (FIG. 1) and they share sequence 98% identity. NMB0352 is annotated as a sugar isomerase in the MC58 genome because of the presence of a sugar isomerase (SIS) domain (Bateman, 1999) between residues 38 and 172. A Walker A box is also located within the SIS domain. Unlike *N. meningitidis*, *E. coli* contained two additional psf homologues, gutQ and yrbH. A multi alignment of these five genes is shown in FIG. 2.

Mutation of psf yields a defect in capsule expression in all five disease-associated serogroups. Because psf has been proposed to participate in K1 capsule expression (Cieslewicz and Vimr, 1997), the meningococcal psf homologue was mutated in the serogroup B meningococcal strain NMB. Plasmid constructs for creating polar or nonpolar insertional mutations in psf were used. Despite repeated attempts, only a nonpolar mutation (psf::aphA-3) was generated. The capsule phenotype in multiple transformants of this mutant, designated 206, was assayed by serogroup B capsule specific whole-cell ELISA. Only about 20% of the serogroup B capsule expressed by the parent strain was expressed by the mutant (FIG. 3A). The reduction of capsule in the 206 mutant was further confirmed by colony immunoblots (FIG. 3B). The phenotype was also generated in 100% of transformants of strain NMB using a PCR product containing the aphA-3 cassette (which confers kanamycin resistance) and psf-flanking DNA amplified from the 206 mutant using primers YT60 and YT61 (FIG. 1).

Cieslewicz and Vimr reported that psf mutation resulted in an intracellular accumulation of capsule in a K1-K12 hybrid *E. coli* strain (Cieslewicz and Vimr, 1997). We asked whether the meningococcal psf mutant accumulated intracellular capsular polysaccharide. Mutant 206 was lysed by freeze-thaw treatment or by an EDTA-HEPES method (Moe et al., 1999), and capsular polysaccharide released into the supernatant was quantified by ELISA. No additional capsule was detected in either lysis method when compared to the data from whole-cell ELISA, indicating that intracellular capsule polymer did not accumulate in this mutant.

These data indicate that serogroup B capsule expression was reduced by a nonpolar mutation in psf. To assess if the meningococcal Psf homologue was required for general capsule expression of all disease associated serogroups, cells of serogroup A (strain F8229), C (Fam18), Y (GA0929) and W-135 (GA1002) of *N. meningitidis* were transformed with linearized pYT206, and the mutation within psf in all recombinants was confirmed by PCR. Capsule expression was then assessed by whole-cell ELISA (serogroup A) or colony immunoblots (serogroups C, Y, and W-135) using capsule serogroup-specific monoclonal antibodies. Reduced capsule expression was observed in all recombinants (FIG. 3B). These results demonstrated that Psf was required for the expression of either sialic acid (serogroup B, C, Y, and W-135) or non-sialic acid (serogroup A) containing capsular polysaccharides.

Figure 4:
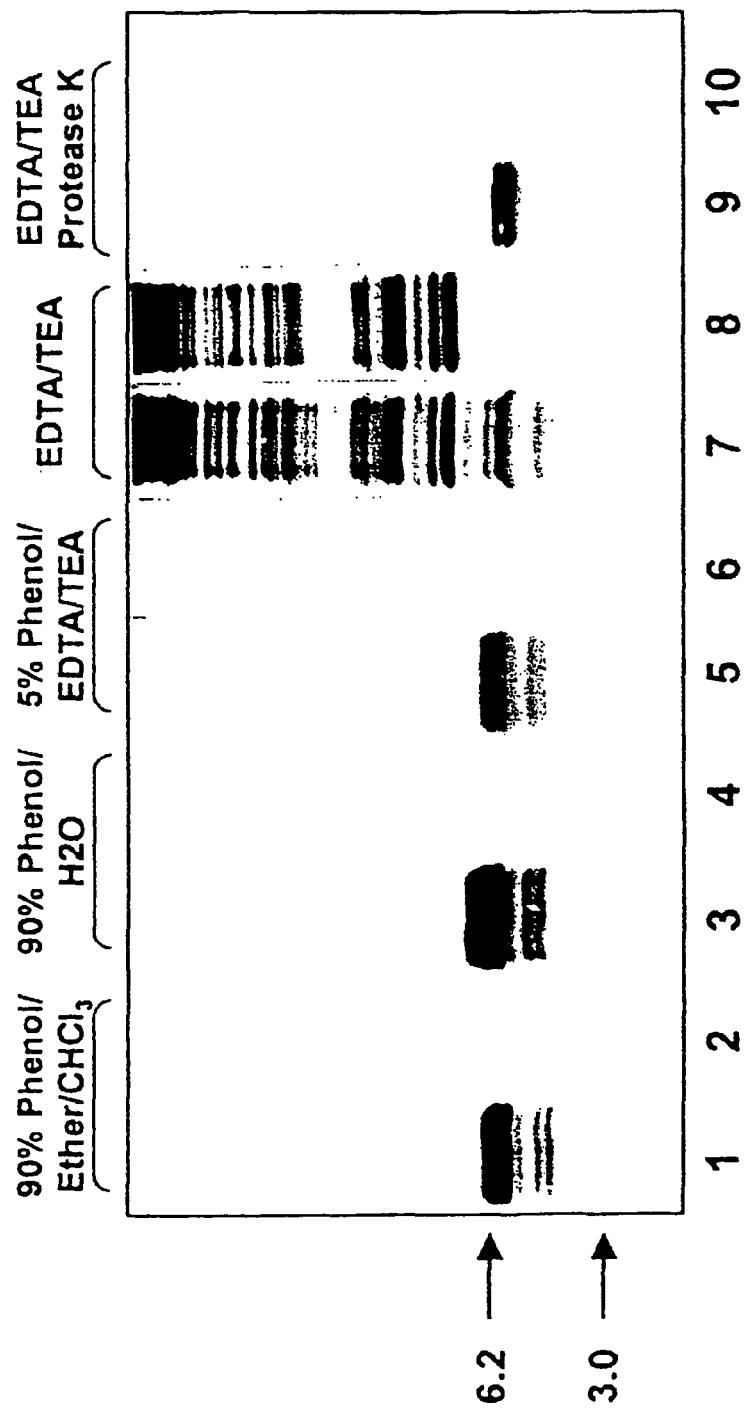

Lipooligosaccharide was markedly truncated in the NMB206 mutant and contained only lipid A. The 206 mutant formed small crinkled colonies that had a dry-rough appearance. To assess whether other outer membrane structures were altered in the mutant, whole cell lysates and outer membrane preparations were examined. No major alteration was seen in either type of protein preparation. Proteinase K treated whole cell lysates examined by Tricine-SDS-PAGE followed by silver staining revealed no LOS silver-stained bands. To determine whether LOS was present in this mutant, we used four different LOS extraction methods: phenol-chloroform-petroleum ether, hot phenol-water, EDTA-TEA-proteinase K and EDTA-TEA-5% phenol. As shown in FIG. 4, no silver-staining bands corresponding to LOS of the wild type parent strain were observed in any of these extractions. Because a truncated LOS structure containing only lipid A-Kdo$_2$ (mutant 469, Kahler et al., 1998)) can be detected by silver staining, these data indicated that either the LOS structure was further truncated or that no LOS was produced by the meningococcal psf mutant.

Fatty acid analysis of the LOS revealed the presence of approximately equal molar amounts of dodecanoic acid (C12:0, 980 nmol/mg), 3-hydroxydodecanoic acid (3-OHC12:0, 965 nmol/mg), and 3-hydroxytetradecanoic acid (3-OHC14:0 940 nmol/mg). A small amount of palmitic acid (C15:0) was also observed which was not part of the LOS, and, perhaps, was due to the presence of a low level of contamination phospholipids. The same fatty acyl residues were present in the same ration in HF-treated LOS, except that in this case a significant level of glucosamine (GlcN) was also detected (925 nmol/mg). Assuming a normal lipid A structure which would have two moles of fatty acid per mole of lipid A, i.e., approximately 2 moles each of C12:0 3-OHC12:0, and 3-OHC14-0. After treatment of lipid A with sodium methoxide C12:0 and 3-PHC12;0 were quantitatively liberated as methyl esters, showing that they had been exclusively ester linked. The mild alkaline-treated LOS was subjected to strong alkaline hydrolysis which released only 3-OHC14;0 and proved that this was the amide bound fatty acyl residue. Thus, composition analysis suggests that NMB206 produces an LOS with the expected lipid A for *N. meningitidis*. However, what proved to be very unusual was that the LOS contained no detectable glycosyl components other than the GlcN that is derived from the lipid A. In fact, none of the glycosyl residues typical of LOS from the wild type NMB or its mutants (Rahman et al., 1998) was detected including the inner core sugar residues, heptose and Kdo.

Figure 13A:
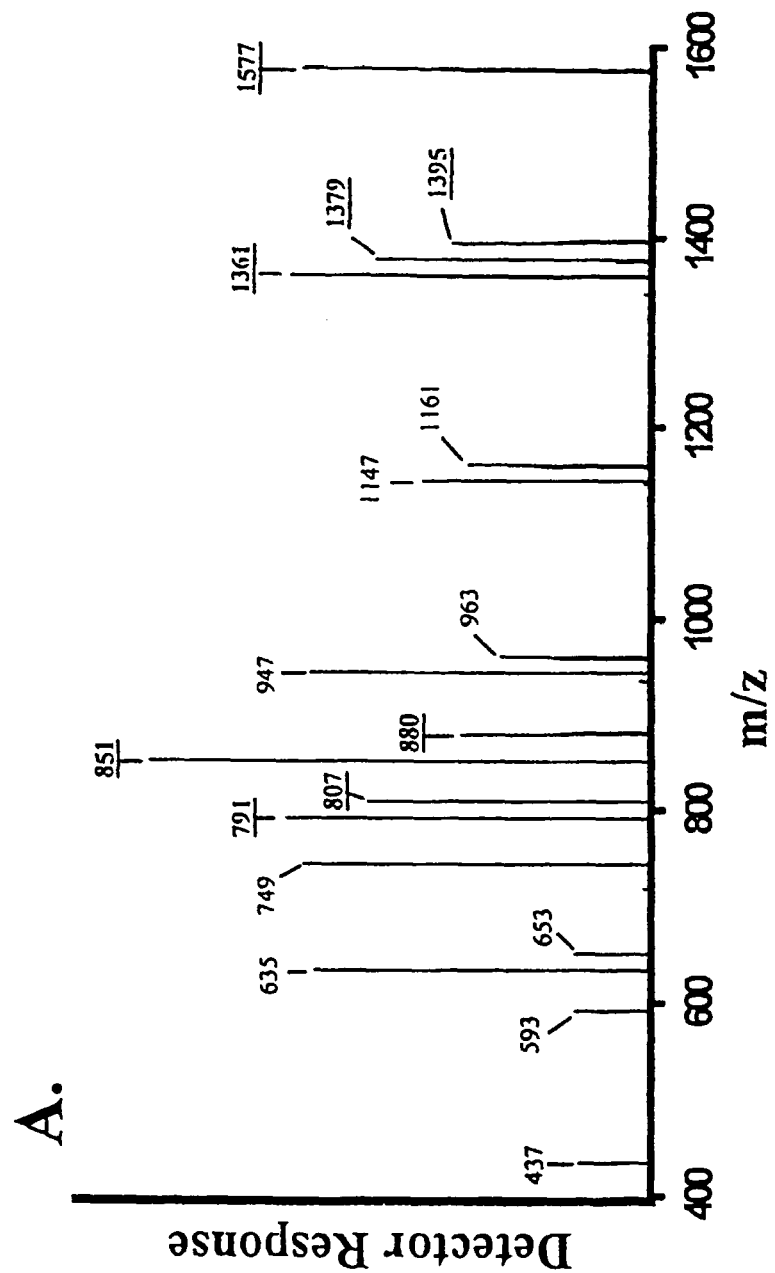
FIGS. 13A-13C show tandem MS/MS spectrum of the 1577 ion of the HF-treated LOS from NMB249 (FIG. 13A). The structure of primary fragmentation of this molecule (FIG. 13B) and the rationale accounting for the observed secondary fragments (FIG. 13C).

These results indicated that the LOS from NMB206 consisted only of lipid A since no glycosyl residues could be detected and since it contained the typical fatty acylation pattern for *N. meningitidis* lipid A. Further structural analysis by mass spectrometry confirmed this conclusion. The LOS from NMB206 was analyzed by MALDI-TOF MS. The results are shown in FIG. 13A. The [M-H]$^-$ ion of major intensity was m/z and 1633, and those of minor intensities were m/z 1756, 1451, 1435, and 864. The m/z 1756 ion is not present in the spectrum shown in FIG. 13A, but did occur in a second preparation as a minor ion together with the other ions mentioned. These different molecular ions were due to variations in phosphate, phosphoethanolamine (PEA) and fatty acyl substitution patterns. Except for m/z 864, all of the molecular species observed were consistent with the conclusion that the LOS consisted only of lipid A and did not contain any detectable Kdo or core glycosyl residues. The minor ion at 864 is consistent with a mono-phosphorylated triacylglucosamine equivalent to one-half of a lipid A molecule. Mild acid hydrolysis, which would remove glycosidically linked phosphate, does not alter the MALDI-TOF spectrum and indicates that the single phosphate group is most likely not glycosidically linked and is, therefore, located at the 4' position. Much of the heterogeneity in the NMB206LOS was removed by treatment with aqueous HF, which removes all phosphate substituents. MALDI-TOF MS analysis in the positive mode of the HF-treated LOS (FIG. 5B) revealed a major [M+Na]$^+$ ion at 1576 (the calculated value is 1577), and a minor ion at 1394. The m/z 1576 ion is consistent with a molecule of composition GlcN$_2$C12:0$_2$βOHC12:0$_2$βOHC14:0$_2$ and the ion at m/z 1394 with GlcN$_2$C12:0$_1$βOHC12:0$_2$βOHC14:0$_2$. The m/z 1576 ion is derived from the LOS species at m/z 1756 and 1633. The m/z 1394 ion is derived from the LOS m/z 1451 species. Ions derived from the minor LOS species at m/z 1435 or 864 were not detected.

The above MALDI-TOF results showed that NMB206 produces one major LOS molecule, i.e. at m/z 1633, which consists of the typical N. meningitidis lipid A with only one phosphate. This LOS is completely devoid of any of the core glycosyl residues including Kdo. The results also suggest that the one phosphate group is located at the 4' position and that there is no glycosidically linked phosphate. In order to confirm the location of the phosphate, the LOS was methylated and partially methylated alditol acetates (PMAAs) were prepared and analyzed by GC-MS. In this procedure the GlcN residues that are phosphorylated at the 4' position retain the phosphate in their PMAA derivative and are not observed during GC-MS analysis, while the reducing-end GlcN, or GlcN-1-phosphate residues of the lipid A are observed as the PMAA derivatives of 6-linked GlcN (Rahman et al., 1989). Since there was not detectable terminally linked GlcN, these results support the conclusion that the 4' position in the LOS is phosphorylated and, therefore, the single phosphate group on this LOS must be located at the 4' position.

Figure 5A:
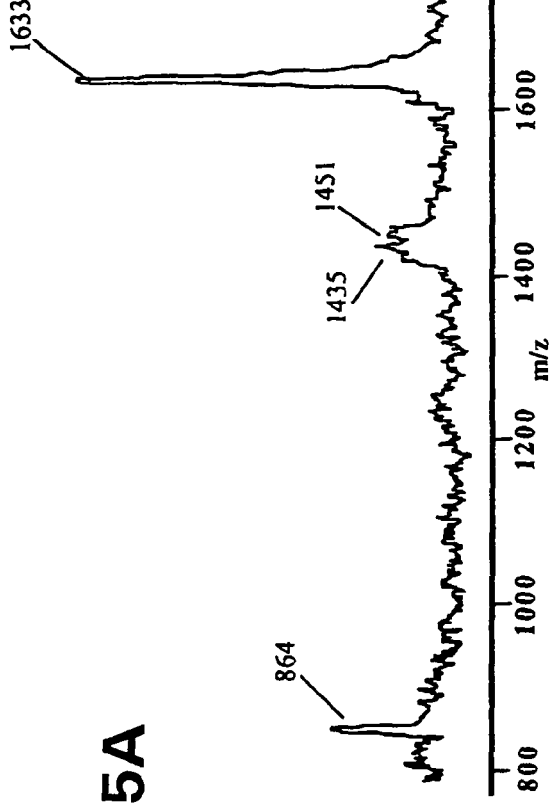
Figure 5B:
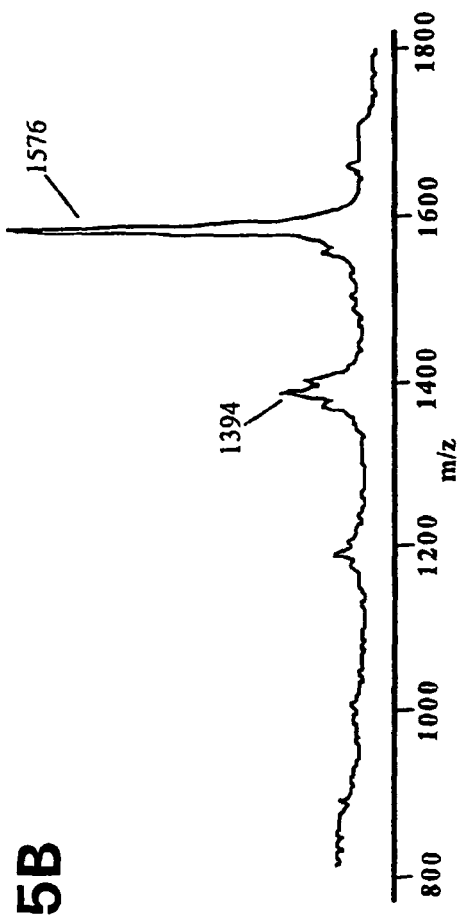

The structure of the LOS, after removal of the phosphate substituents was further analyzed by tandem MS.MS analysis, FIG. 5A-5B. The [M+Na]$^+$ ion, m/z 1576, gives primary fragments due to (a) the loss of either β-hydroxylaurate (−215, m/z 1361), β-hydroxylauryl (−199, m/z 1379), laurate (−199, m/z 1379), or lauryl (−183, m/z 1394) fatty acyl components, (b) cleavage between the glycoside bond (m/z 807 and 791), (c) cleavage of the glycoside ring of the GlcN residue at the C3-C4 and C1-O5 bonds (m/z 880), and (d) cleavage of the glycoside ring at the C4-C5 and C1-O5 bonds (m/z 851). The remaining fragments are due to the loss of β-hydroxylaurate, β-hydroxylauryl, or laurate from several of the primary fragments. This fragmentation pattern is completely consistent with the typical symmetrically fatty acylated lipid A reported for *N. meningitidis*.

From the above results, it is clear that the LOS from NMB206 consists primarily of lipid A that is not glycosylated and contains a single phosphate group at the 4' positions. There are minor species in which this phosphate is substituted by a PEA group (m/z 1756), lack one of the fatty acyl substituents (m/z 1435 and 1451), or consist of a monophosphorylated triacylglucosamine residue (m/z 864). The structure of the major LOS from NMB206 is shown in FIG. 5B.

Mutation of psf also resulted in reduced growth and incomplete septum separation in *N. meningitidis*. The growth curves of the 206 mutant in GC broth and BHI broth were compared to those of the wild type parent. The growth rate of the mutant was much reduced; its doubling time is about fourfold slower than that of the wild type parent. Both the mutant and parent strain were piliated, as determined by electron microscopy after negative staining. Electron microscopy of a thin sectioned bacterial pellet of the psf mutant showed (FIG. 6A-6D) that the structure of outer membrane, peptidoglycan, and inner membrane were intact; however, the mutant exhibited thickened septum separating the diplococci. In addition, the psf mutant was often found as diplococci, tetracocci and even larger clusters of cells that were not properly separated, reflecting a defect in cell division.

To demonstrate that psf mutation caused the phenotype observed, complementation experiments were performed to introduce a second copy of psf. Despite numerous attempts, we were not able to transform the 206 (psf::aphA-3) mutant with DNA, indicating decreased competence of the mutant. To overcome this problem, we incorporated a second copy of psf prior to the inactivation of the wild type gene (see hereinbelow). PCR and Southern blots confirmed that the aphA-3 insertion occurred at the wild type copy of psf. When capsule was examined by whole-cell ELISA and colony immunoblot, this complemented strain appeared identical to the wild type, indicating that the defect in the wild type copy of psf complemented by the presence of the second copy of psf.

The *E. coli* K1 Psf protein can complement the meningococcal psf mutation, which exhibits 64% similarity to the *E. coli* K1 Psf protein. To determine if these two proteins function in the same way, we first constructed a strain (240) carrying pYT240, an Erm$^R$ shuttle vector containing the *E. coli* K1 psf coding sequence fused in frame to a Flag epitope coding sequence and expressed under the control of the tac promoter. We then disrupted the meningococcal psf using a PCR fragment (primers YT60 and YT61) amplified from the 206 mutant that contained the aphA-3 cassette within the psf coding sequence. Erm$^R$ and Kan$^R$ transformants (240/206) were identified that contained the insertion of the aphA-3 cassette into the meningococcal psf and an intact copy of *E. coli* K1 psf on the shuttle vector. A strain (250) containing the shuttle vector without the *E. coli* psf insert (pYT250) was used to generate a negative control strain (250/206) for the complementation experiments.

Figure 7A:
Figure 7B:
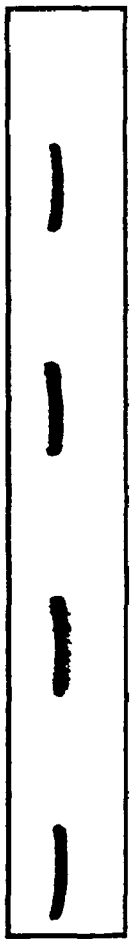
Figure 7C:
Figure 7D:

Whole cell lysates of strains, NMB206, NMB240, NMB240/206, NMB250 and NMB250/206 were analyzed by Western blots probed with an anti-Flag monoclonal antibody (FIG. 7A) and anti-Psf polyclonal antiserum (FIG. 7B). K1 Psf-flag proteins were expressed at a similar level in the 240 and 240/206 strains without induction, indicating incomplete suppression by LacI. Increased expression was observed in the presence of IPTG (FIG. 7A). The absence of reactive bands in strains containing psf::aphA-3 mutations, when probed with antiserum against meningococcal Psf, confirmed that these mutations eliminated expression of meningococcal Psf (FIG. 7B). The colony morphology and growth rate of the NMB240/206 strain were similar to the wild type parent; while the NMB250/206 strain resembled the NMB206 strain. When these strains were examined by the capsule-specific whole-cell ELISA, the NMB240/206 strain yielded wild type level of capsule expression while the NMB250/206 produced a capsule-deficient phenotype similar to that of strain NMB206 (FIG. 7D). These data demonstrated that *E. coli* K1 Psf can replace the meningococcal Psf and complement the capsule deficient phenotype of the NMB206 mutant. When LOS from these strains was examined by silver stained Tricine-SDS-PAGE, wild type LOS bands were restored in the NMB240/206 strain but not the NMB250/206 strain, indicating complementation of meningococcal psf LOS defect by *E. coli* K1 Psf (FIG. 7C).

Mutation in tal did not influence capsule expression, and lipid A and Kdo were normal. The gene for a putative transaldolase (tal) is immediately upstream of psf; it is transcribed divergently from psf with a 96 bp intergenic space. We determined that this gene, whose product is predicted to function in the pentose phosphate metabolic pathway (Wood, 1985), does not function in capsule biosynthesis in N. meningitidis. A nonpolar aphA-3 insertional mutation was created in tal, and the resulting mutant expressed wild type level of capsule as measured by whole-cell ELISA.

Figure 8:
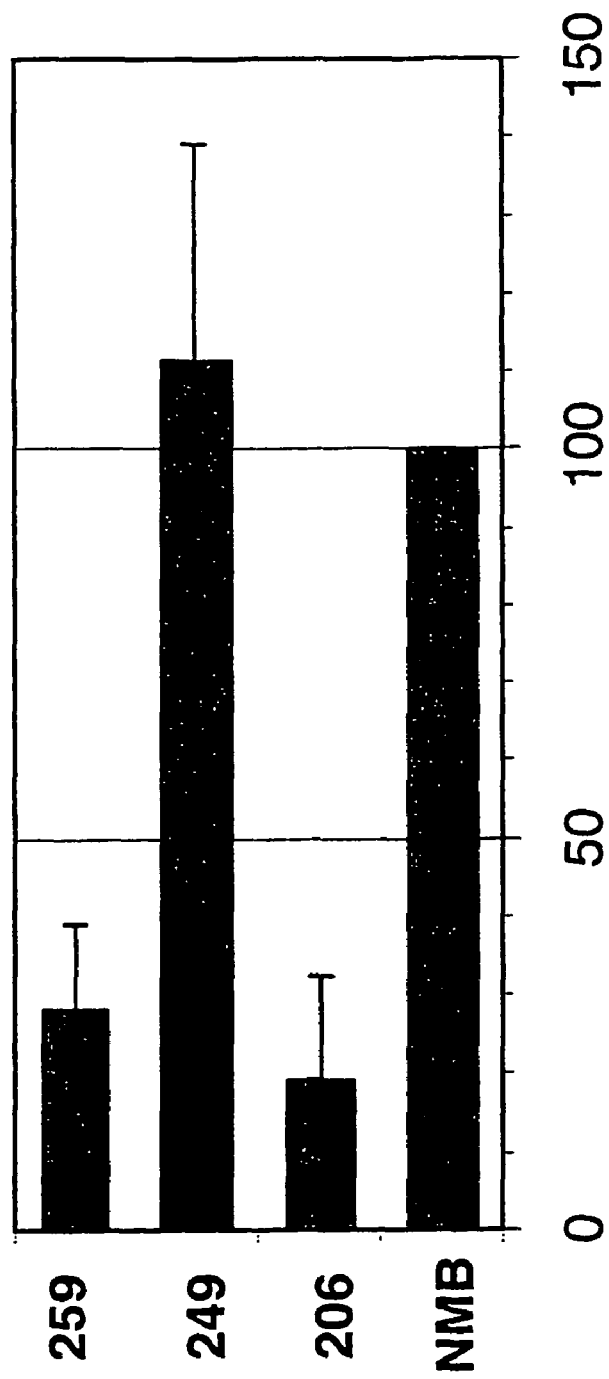

The capsule deficient phenotype of the psf mutant is not caused by the LOS truncation. LOS is the major component of the outer leaflet of the outer membrane, and capsule is anchored on the outer membrane via a diacylglycerol moiety (Gotschlich et al, 1981). Possible structural changes of the outer membrane produced by the markedly truncated LOS (intact lipid A) might affect capsule expression. Although capsule expression was not influenced in previous meningococcal mutants with LOS truncation (Kahler et al., 1998), a kdtA mutation was created in meningococcal strain NMB 249 to further address this question. KdtA is the CMP-Kdo transferase that catalyzes the transfer of Kdo to lipid A. The 249 mutant generated the same truncated LOS structure as that of the psf mutant (intact lipid A). However, this mutant, when analyzed by whole-ell ELISA, produced wild type levels of capsule (FIG. 8). Thus, the reduced capsule expression caused by the psf mutation was not due to outer membrane alterations resulting from truncated LOS.

Kdo biosynthesis is involved in meningococcal capsule expression. The absence of Kdo in LOS and the reduction of capsule expression in the psf mutant suggested a role of Kdo in capsule expression. Kdo has been identified as a component of the *E. coli* K5 capsule at the reducing end of the polymer (Finke et al., 1991). To assess the role of Kdo in meningococcal capsule synthesis, a genetically stable, nonpolar insertion mutation was created in the CMP-Kdo synthetase gene, kdsB, in order to eliminate the production of the activated Kdo sugar. The kdsB mutant, strain 259, grew slowly at 30° C., while at 37° C. spontaneous mutations compensating the growth defect appeared after overnight incubation. When the kdsB mutant was assayed by whole-ell ELISA, a significant reduction in capsule expression, similar to that of the psf mutant, was observed (FIG. 8). These data establish that Kdo plays a role in meningococcal capsule expression and further indicate that Psf is involved in Kdo production.

Figure 9C:
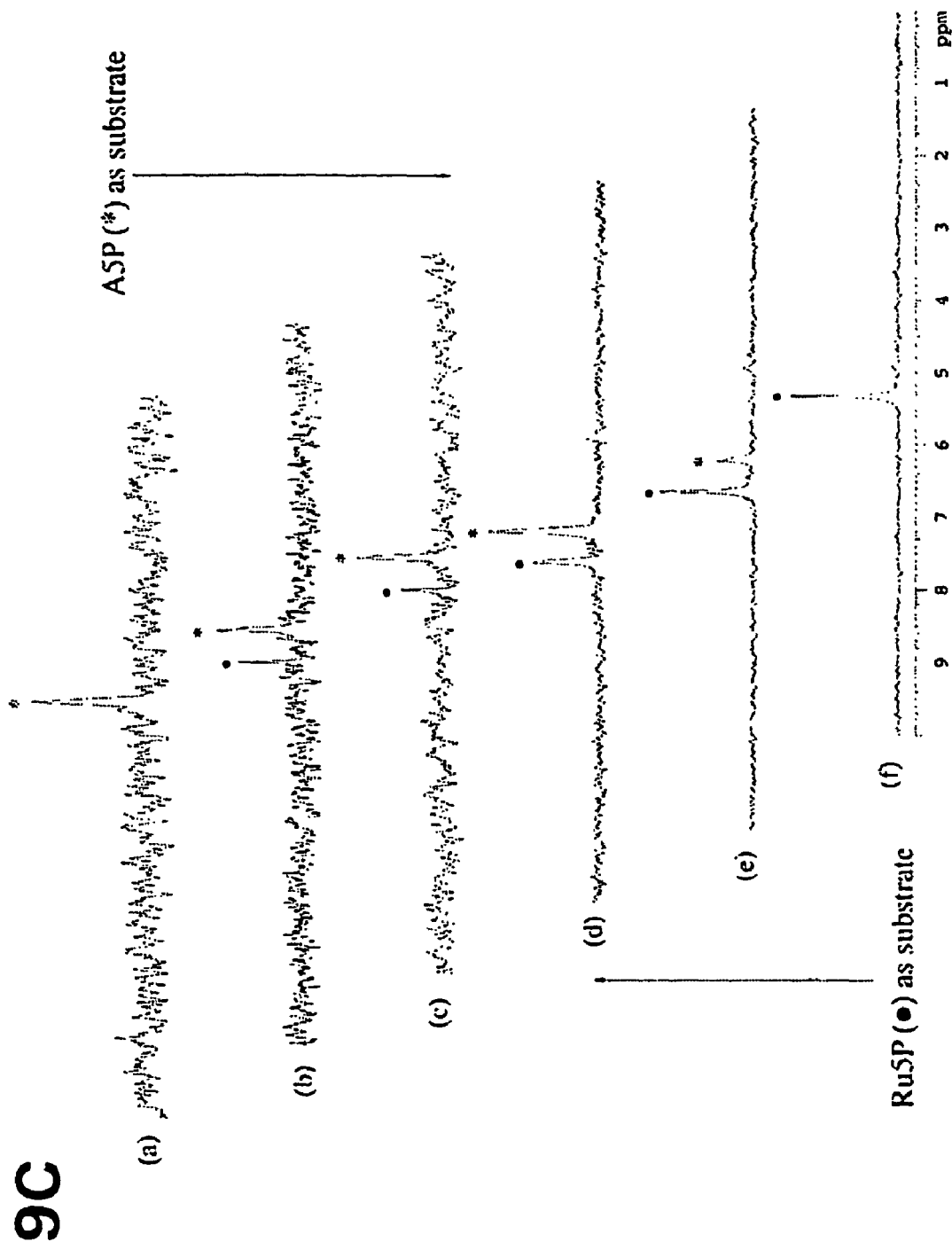

Psf is the arabinose 5-phosphate isomerase of *N. meningitidis*. The predicted protein sequence of Psf suggested a sugar isomerase activity. To determine if Psf had isomerase activity, a colorimetric assay for keto-pentoses (Bigham et al., 1984) was first conducted using the purified Psf protein, which contained a C-terminal 6xHis tag (FIG. 9A). Addition of Psf protein to the reaction mixture containing arabinose 5-phosphate resulted in an increase in color; while adding the protein to ribulose 5-phosphate caused a decrease in reading of $A_{540}$. The reaction was dependent on the concentration of Psf protein. Other monosaccharides, such as erythrose 4-phosphate, glucose 6-phosphate, ribose 5-phosphate and arabinose, did not serve as substrates for the Psf protein. The NMR chemical shifts of the phosphoryl groups of arabinose 5-P and ribulose 5-P are different, thus $^{31}$P NMR can monitor the interconversion between the two sugars. As shown in FIG. 9C, when using arabinose 5-P as the substrate, a new peak corresponding to the phosphoryl group of ribulose 5-P appeared and increased over time, and the same phenomenon was observed for the reverse reaction. These data demonstrate that Psf catalyzes the interconversion of ribulose 5-phosphate and arabinose 5-phosphate. The LOS defect in the psf mutant, but not the kdsB mutant, can be complemented by (exogenous) supplementation of arabinose in the growth medium (FIG. 9B), consistent with the identification of the Psf protein as an arabinose 5-phosphate isomerase.

A nonpolar mutation in the meningococcal psf homologue markedly reduced capsule expression in five disease-associated meningococcal serogroups. In this disclosure, we have shown that the meningococcal Psf is required for Kdo synthesis, that defects in this protein can be complemented by the *E. coli* K1 Psf homologue, that Kdo biosynthesis is involved in capsule expression and that Psf is the meningococcal arabinose 5'phosphate isomerase.

Figure 10:
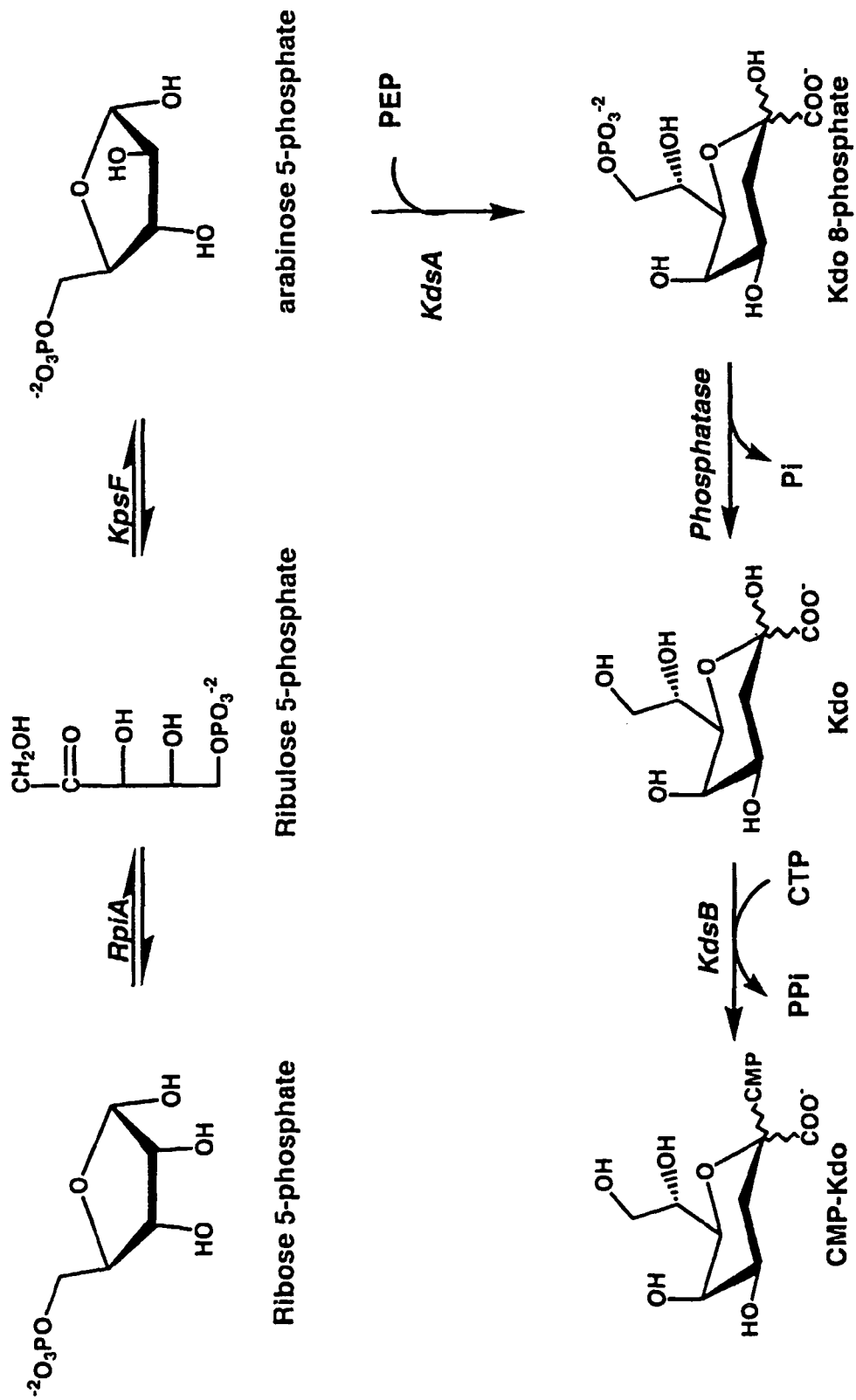
Figure 11:
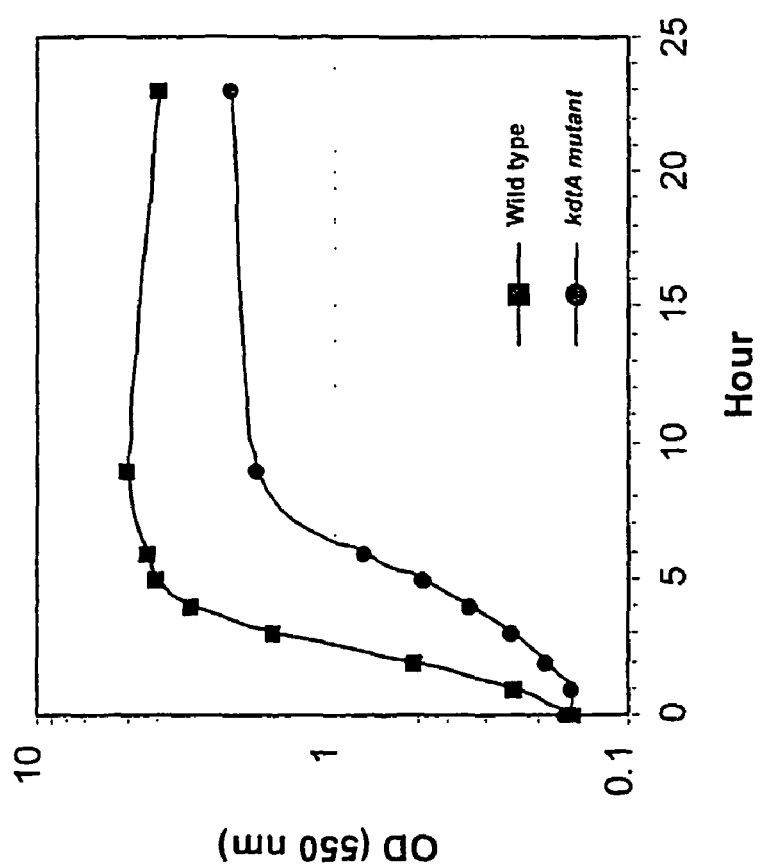
FIG. 11 illustrates growth curves of the *N. meningitidis* serogroup B wild type strain NMB and the kdtA::aphA-3 mutant NMB249. Growth in BHI broth at 37° C. was monitored by measuring the optical density at 550 nm.

The condensation of arabinose 5-phosphate and phosphoenolpyruvate catalyzed by the Kdo synthase, KdsA, is usually considered to be the first step in Kdo biosynthesis (FIG. 10). However, arabinose 5-phosphate is not readily available from glycolysis, and an isomerase is required for the interconversion of ribulose 5-phosphate and arabinose 5-phosphate (FIG. 10). Although the enzymatic activity has been demonstrated in cell extracts, the gene encoding this enzyme has not been previously identified (Bigham et al., 1984). The Psf protein contains a sugar isomerase (SIS) domain commonly found in proteins including GlmS and LpcA (Bateman, 1999), which are involved in phosphosugar isomerization. In addition, the SIS domain is also present in the transcriptional regulator, RpiR, of the ribose phosphate isomerase, RpiA, which interconverts ribose 5-phosphate and ribulose 5-phosphate, a reaction that precedes the arabinose 5-phosphate isomerase. Interestingly, in addition to psf, region 1 of the capsule locus of *E. coli* strains expressing group II capsule encodes a second copy of the CMP-Kdo synthetase (kpsU). In *E. coli*, this reflects an evolutionary gene duplication to ensure that the Kdo substrate required for capsule biosynthesis was not limited by requirements of the LPS biosynthesis pathways. In fact, in *E. coli* two other predicted proteins, GutQ and YrbH, are homologues of Psf. GutQ is located within the glucitol operon, but its function has not been determined (Yamada et al., 1990).

Although psf is conserved (98% amino acid identity) in *E. coli* strains expressing K1 and K5 capsular polysaccharides (Cieslewicz and Vimr, 1996; Simpson et al., 1996), its role in capsule expression has not been established. The expression of region 1 in *E. coli* is regulated by temperature at the transcriptional level; however, Psf is not required for thermoregulation (Cieslewicz and Vimr, 1996). A nonpolar psf mutation resulted in about 10-fold reduction of capsule translocation to the surface of K1 *E. coli* (Cieslewicz and Vimr, 1997). Psf is, however, not required for K5 capsule expression since cloning the K5 capsule gene cluster lacking psf into a K12 strain produced a capsule comparable to that of the wild type K5 strain (Pazzani et al., 1993). The meningococcal genomes, however, have no other homologues of psf. We have shown that K1 psf can complement the meningococcal psf defect in both LOS biosynthesis and capsule expression. This result shows that the *E. coli* K1 and meningococcal psf homologue performed the same functions. Without wishing to be bound by theory, the lack of a detectable phenotype in *E. coli* psf mutants is believed to be due to the presence of gutQ and/or yrbH.

Our data indicate that Kdo is involved in capsule expression. Gotschlich et al. has characterized the structures of meningococcal capsular polysaccharides from serogroups A, B, and C (Gotschlich et al., 1981). The authors reported a diacylglycerol substitution at the reducing end of capsule polymers, but no Kdo residues were detected. Kdo is the reducing sugar in the *E. coli* K5 capsule (Finke et al., 1991) Although K1 and K5-producing *E. coli* have identical organizations of region 1, Kdo has not been detected to date in K1 polymers. Finke et al. hypothesized that the biosynthesis of K5 capsule is initiated by substitution of the undecaprenol phosphate (UP) carrier with Kdo, which then acts as an acceptor for subsequent polymerization (Finke et al., 1991). On the other hand, Troy et al. proposed UP as an intermediate carrier in sialyl polymer synthesis in *E. coli* (Troy et al., 1975). The Kdo-UP carrier may be replaced in meningococci by a final phospholipid substitution step (Gotschlich et al., 1981), thus removing Kdo from the final assembled capsule polymers. Interestingly, in both meningococcal psf and kdsB mutants, capsule expression was significantly reduced but not completely eliminated. If meningococci employ a model like that proposed in K5 capsule expression where Kdo-UP acts as the acceptor for capsule polymerization, our results suggest that Kdo-UP is not the only acceptor because no activated Kdo is available in the kdsB mutant. Without wishing to be bound by theory, we believe that UP alone acts as an alternative acceptor responsible for the residual capsule synthesis seen in the Kdo-deficient mutants.

Three meningococcal mutants, psf, kdtA and kdsb, were shown in this study to synthesize intact lipid A without Kdo. These data demonstrate that the lipid A biosynthesis pathway in meningococci is different from that of enteric bacteria. In *E. coli* and *S. typhimurium*, both acyloxyacyl moieties are added after the addition of Kdo residues to lipid $IV_A$ (Raetz, 1996). Among the three Kdo mutants, only the kdsB mutant is temperature sensitive. Because KdsB is the only CMP-Kdo synthetase encoded in the meningococcal genome, CMP-Kdo is believed to participate in important metabolic pathways other than LOS and capsule expression, thus yielding a stronger pleiotropic effect on growth.

A tetrapac phenotype was first reported in *Neisseria gonorrhoeae* having a rough-colony morphology and bacterial growth in clusters of four (Fussenegger et al., 1996). The gene (tpc) responsible for this phenotype, which encodes a putative secreted lipoprotein, is also present in meningococci (NMB0693, MC58 genome). Mutation in tpc, which is believed to encode a murein hydrolase, also causes transformation deficiency. However, unlike the psf mutant, the tpc mutant grows normally. No defect in murein hydrolase activity has been observed in the psf mutant to date.

Figure 1C:
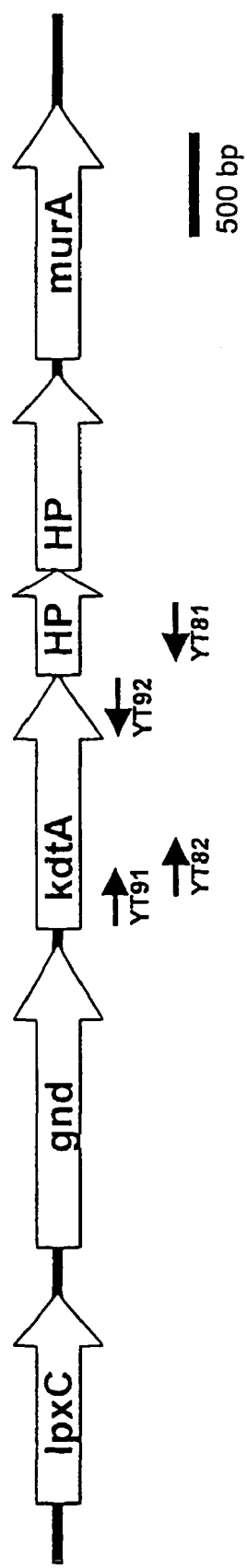

The kdtA gene (NMB0014) was identified from the serogroup B meningococcal MC58 genome (Tettelin et al., 2000). The gene is located downstream of gnd and lpxC and is followed by two hypothetical proteins and murA, all transcribed in the same orientation (FIG. 1C). This organization differs from that of *E. coli* in which kdtA is transcribed divergently from the rfa operon (Raetz et al., 1996). The MC58 sequence was used to design primers and clone kdtA from the meningococcal serogroup B strain, NMB. An internal fragment of kdtA was removed with BssHII digestion and replaced with a nonpolar kanamycin resistance aphA-3 cassette to generate plasmid pYT249. Inactivation of the chromosomal copy of kdtA in meningococcal strain NMB was accomplished via transformation with linearized pYT249. The allelic exchange yielded viable kanamycin resistant transformants. The correct incorporation of the aphA-3 cassette into kdtA in one of these transformants, strain NMB259, was confirmed by PCR, Southern blots and sequencing analysis.

The meningococcal kdtA mutant (NMB249) formed small, wrinkled colonies on either BHI or GC agar plates. The growth of mutant NMB249 was assessed in BHI broth and was slower when compared to that of the wild type strain (~25% that of the parent strain). The morphology of this mutant was also examined by transmission electron microscopy. Thin sections of the kdtA mutant revealed bacteria with thickened, incomplete septum separation often in tetrads, resembling that described for a tpc mutant of *Neisseria gonorrhoeae*, termed tetrapac (Fussenegger et al., 1996).

To examine LOS in the kdtA mutant, proteinase K treated whole cell lysates were prepared and resolved by Tricine-SDS-PAGE. Silver staining revealed wild type LOS in the parent strain but no stainable LOS in the mutant. Since the meningococcal Re endotoxin structure (Kdo2-lipid A) and larger structures can be visualized by silver staining, the results with the kdtA mutant indicated that Kdo was likely absent in the LOS of the strain NMB249. This finding was consistent with the inactivation of the Kdo transferase. To determine the precise endotoxin structure in the kdtA mutant, the kdtA endotoxin was subjected to phenol-chloroform-petroleum ether extraction for endotoxin isolation, and the LOS recovered subjected to detailed structural analysis.

Fatty acid analysis of the LOS revealed the presence of approximately equal molar amounts of dodecanoic acid (C12:0, 1050 nmol/mg), 3-hydroxydodecanoic acid (3-OHC 12:0, 1000 nmol/mg), and 3-hydroxytetradecanoic acid (3-OHC 14:0, 975 nmol/mg). A small amount of palmitic acid (C16:0) which was not part of the LOS was also observed. Perhaps it was due to a low level of contaminating phospholipid. The same fatty acyl residues were present in the same ration in HF-treated LOS, except that in this case a significant level of *N. acetylglucosamine* (GlcNAc) was also detected (945 nmol/mg). Assuming a normal lipid A structure which would have 2 moles of GlcN per mole of lipid A, it can be concluded that there are a total of 6 moles of fatty acid per mole of lipid A, i.e. approximately 2 moles each of C12:0, 3-OHC 12:0, and 3-OHC 14:0. After treatment of lipid A with sodium methoxide C12:0 and 3-OHC 12:0 were quantitatively liberated as methyl esters, showing that they had been exclusively ester linked. The mild alkaline-treated LOS was subjected to strong alkaline hydrolysis which released only 3-OHC14:0 and proved that this was the amide bound fatty acyl residue. Thus, composition analysis suggests that strain NMB249 produces an LOS with the expected lipid A for *N. meningitidis*. Surprisingly, the LOS contained no detectable glycosyl components other than the GlcN that is derived from the lipid A, and no detectable Kdo was present in this LOS preparation.

Figure 12A:
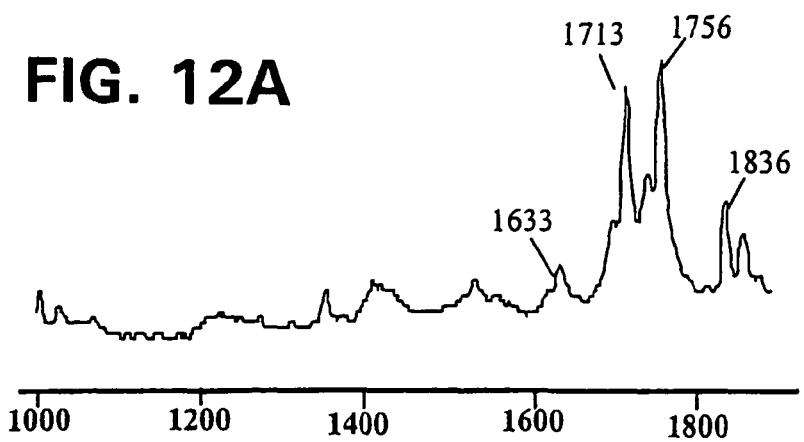
FIGS. 12A-12B show MALDI-TOF spectra of two LOS preparations from NMB 249 and from HF-treated LOS from NMB249 (FIGS. 12A and 12B, respectively). Spectra in FIGS. 12A and 12B were collected in the negative mode, and spectrum shown in FIG. 12C was collected.
Figure 12B:
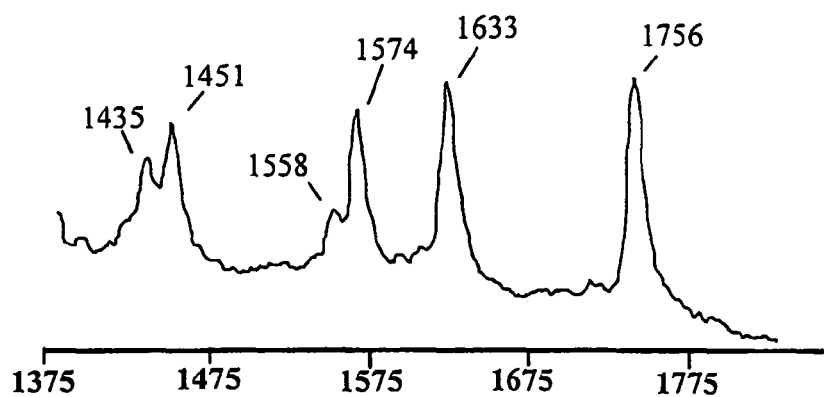
Figure 12C:
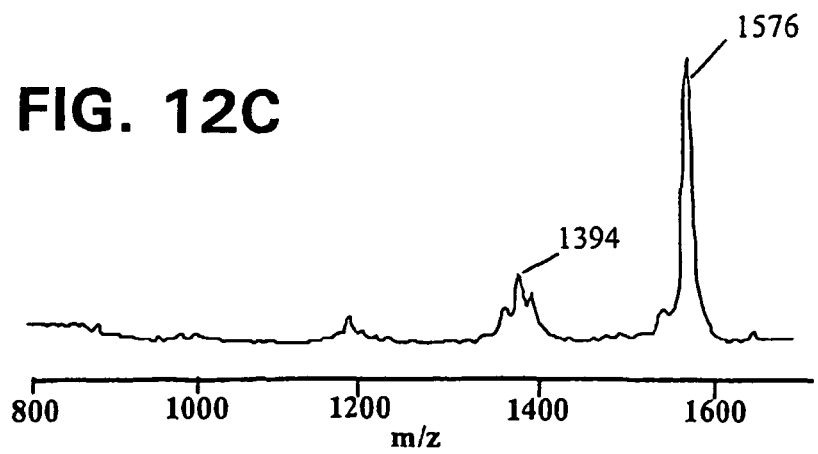

It appeared that the LOS from NMB249 consisted only of lipid A since no glycosyl residues could be detected and since it contained the typical fatty acylation pattern for *N. meningitidis* lipid A. This was confirmed by mass spectrometry. The LOS from two different NMB249 preparation was analyzed by MALDI-TOF MS. The results are shown in FIGS. 12A-12C. The [M-H]$^-$ ions varied somewhat between the two preparations for unknown reasons. These ions were m/z 1836, 1756, 1713, 1633, 1574, 1558, 1451, and 1435. If one considers both LOS preparations the major species are m/z 1756, and 1713, followed by 1633, the different molecular ions were due to variations in phosphate, phosphoethanolamine (PEA) and fatty acyl substitution patterns. Table 4 lists the proposed compositions for each ion together with their respective calculated ion masses. All of the molecular species observed were consistent with the conclusions that the LOS consisted only of lipid A, it did not contain any detectable Kdo or core glycosyl residues, and the major LOS molecular species contained the normal lipid A fatty acid components. Much of the heterogeneity was removed by treatment of the LOS with aqueous HF, which removes all phosphate substituents. MALDI-TOF MS analysis in the positive mode of the HF-treated LOS revealed a major [M+Na]$^+$ ion at 1576 (the calculated value is 1577), and a minor ion at 1394. The m/z 1576 ion is consistent with a molecule of composition GlcN$_2$C12:0$_2$βOHC12:0$_2$βOHC4:0$_2$, and the ion at m/z 1394 with GlcN$_2$C12:0$_1$βOHC12:0$_2$βOHC14:0$_2$. The m/z 1576 ion is derived from the major LOS species at m/zI 1836, 1756, 1713, and 1633. The 1394 ion is derived LOS species present in the next highest m/zI concentration, m/z 1574, and 1451. An ion derived from the minor LOS species at m/z 1558 and 1435, i.e. 1378, was not detected perhaps because it was not present in sufficient amounts.

The MALDI-TOF results showed that several molecular species lacked one phosphate, and varied in the presence of absence of one PEA substituent. In species that lacked one phosphate group, it was necessary to determine if the second phosphate group was the glycosidically linked phosphate or the 4'-phosphate. Therefore, the LOS was methylated and partially methylated alditol acetates (PMAAs) were prepared and analyzed by GC-MS. In this procedure the GlcN residues that are phosphorylated at the 4'-position retain the phosphate in their PMAA derivative and are not observed during GC-MS analysis, while the reducing-end GlcN or GlcN-1-phosphate residues of the lipid A are observed as the PMAA of 6-linked GlcN (Rahman et al. 1998). The results showed only the presence of 6-linked GlcN, which is derived from the lipid A reducing-end GlcN residue. Because there was no detectable terminally linked GlcN, these results support the conclusion that the 4'-position in all of the LOS molecules is phosphorylated and, therefore, those species that lack phosphate are missing the glycosidically linked phosphate residue. Several of the LOS species contain a single PEA substituent, in the form of either a PEA-P-4'-GlcN- or a -GlcN-1-P-PEA substituent. Mild acid hydrolysis of the LOS with 1% acetic acid at 100° C. for 1 hour would convert -GlcN-1-P-PEA to -GlcN, but would leave the PEA-P-4'-GlcN intact. MALDI-TOF MS analysis of the LOS after mild acid hydrolysis showed two ion species, m/z 1756 and 1633, due to molecules with a single P-PEA or a single-P substituent, respectively. Thus, it is likely the PEA group, when present on the LOS, exists as a PPEA group on the 4'-position.

Figures 13B, 13C:
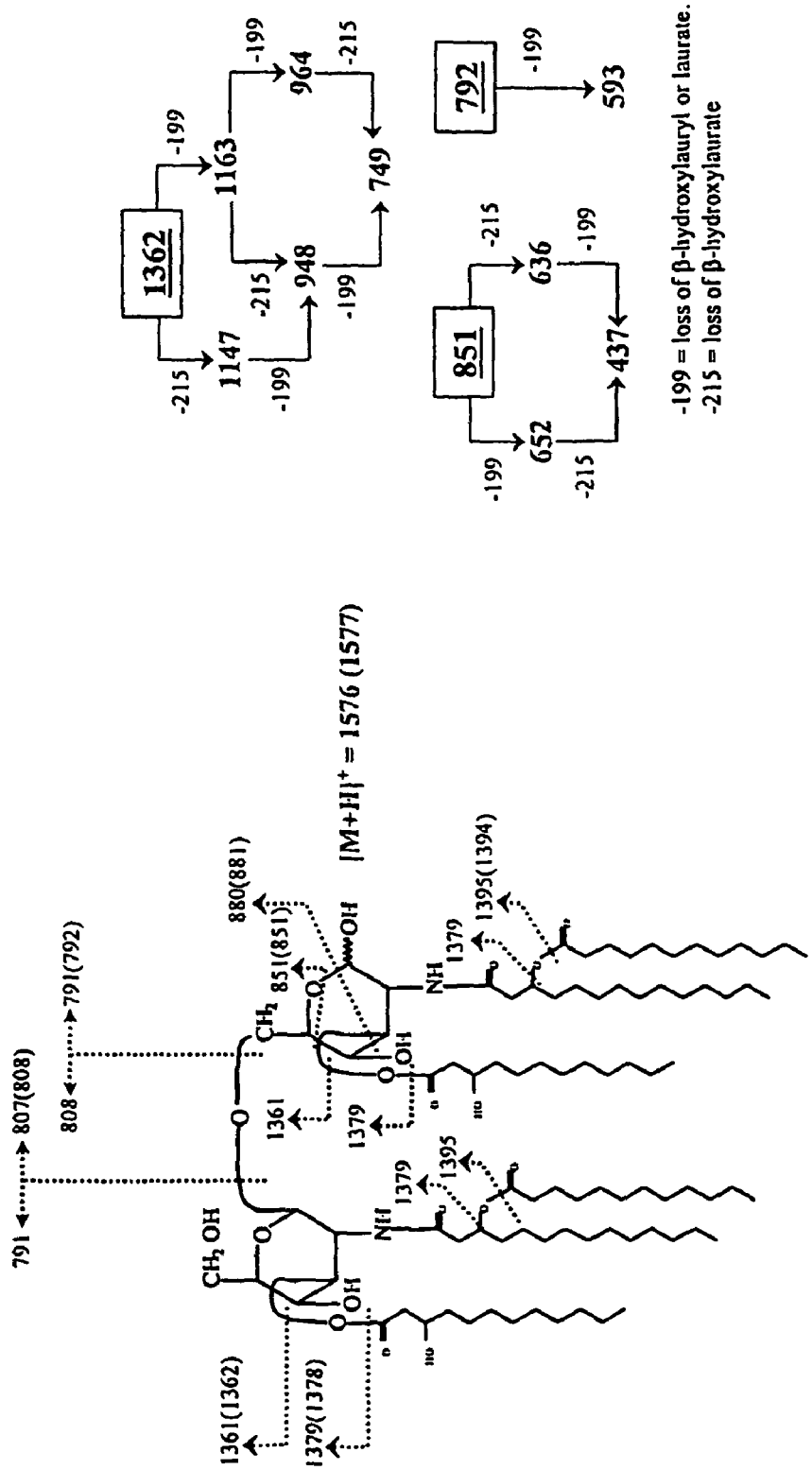

The structure of the LOS, after removal of the phosphate substituents, was further analyzed by tandem MS/MS analysis (FIG. 13A). The [M+Na]$^+$ ion, m/z 1577, gives primary fragments due to the loss of either β-hydroxylaurate (−215, m/z 1361), β-hydroxylauryl (−199, m/z 1379), laurate (−199, m/z 1379), or lauryl (−183, m/z 1394) fatty acyl components, to cleavage between the glycoside bond (m/z 807 and 791), and to cleavage of the glycoside ring of the GlcN residue at the C3-C4 and C1-O5 bonds (m/z 880), and at the C4-C5 and C1-O5 bonds (m/z 851). This fragmentation pattern is shown in FIG. 13B. The remaining fragments are due to the loss of β-hydroxylaurate, β-hydroxylauryl, or laurate from several of the primary fragments. A scheme showing how these ions might arise is given in FIG. 13C. This fragmentation pattern is completely consistent with the typical symmetrically fatty acylated lipid A reported for *N. meningitidis*.

From the above results, it is clear that the LOS from this mutant consists primarily of lipid A that is not glycosylated but contains variability in its phosphorylation. There are also minor molecular species present that lack either a lauryl or a β-hydroxylauryl substituent. The structures of the major structures from this mutant are shown in FIG. 6.

To confirm the phenotype of the NMB249 mutant was caused by inactivation of KdtA, and to test whether KdtA of *E. coli* can substitute for the meningococcal KdtA, we performed complementation experiments using the meningococcal shuttle vector, pYT250. Based on the meningococcal MC58 genome and the *E. coli* K12 genome, kdtA was amplified from *N. meningitidis* (NMB) and *E. coli* (DH5α) and cloned into pYT250 to generate pTY271 and pYT274, respectively, as described hereinbelow. The second copy of kdtA was constructed to be controlled by a tac promoter to avoid possible promoter effects. A Flag octapeptide tag (DYKDDDDK) (SEQ ID NO:1) was also incorporated into the C-terminus of the KdtA proteins encoded on the shuttle vectors so that KdtA expression in meningococci could be conveniently monitored.

Due to the difficulty in transforming strain NMB249, plasmids pYT271 and pYT274 were first introduced into the parent meningococcal strain NMB, generating Erm$^r$ transformants. These strains were subsequently transformed with linearized pYT249, and Erm$^r$/Kan$^r$ transformants were selected. Colony PCR analyses with chromosomal specific primers confirmed the insertion of aphA-3 cassette into the chromosomal copy of kdtA, and PCR with shuttle vector specific primers confirmed that the second copy of kdtA was intact. In addition, Southern blots were performed with probes specific to meningococcal kdtA or alpA-3 cassette, and the results showed correct insertion of the aphA-3 cassette. We also generated a strain carrying the meningococcal shuttle vector pYT250. Attempts to introduce kdtA::aphA-3 mutation into this background were not successful, probably due to the double selection requirement and the pleiotropic effect of kdtA mutation on growth. The ability to introduce the kdtA::aphA-3 mutation while maintaining shuttle vector can only be achieved in the presence of the second copy of kdtA, suggesting that complementation had occurred.

To confirm, proteinase K treated whole cell lysates were prepared from the parent strain NMB, mutant strain NMB249 and two independent transformants of the complemented strains, NMB249/271 and NMB249/274. Tricine SDS-PAGE analysis of the LOS sampled demonstrated that the wild type LOS phenotype was restored by the introduction of either the meningococcal or *E. coli* kdtA. The expression of flag-tagged KdtA proteins in strains NMB249/271 and NMB249/274 was demonstrated by immunoblot analysis.

LPS biosynthesis in *E. coli* and other enteric bacteria has been extensively studied, and has been used as a paradigm to infer steps in endotoxin assembly and the requirement of Kdo$_2$-lipid A for viability of other gram-negative bacteria. However, the endotoxin assembly and the minimal structure in *N. meningitidis* are distinct from *E. coli*. Previously, Steeghs et al. have shown that meningococci can be viable without any endotoxin (Steeghs et al., 1998). Further, we show in this study that meningococci can survive expressing only lipid A. In contrast to *E. coli*, the Kdo transferase KdtA is not essential in *N. meningitidis*. In addition, the kdtA meningococcal mutation resulted in the synthesis of fully acylated lipid A without Kdo glycosylation indicating that meningococcal lipid A biosynthesis differs from enteric gram-negative bacteria.

In *E. coli* and *Salmonella*, the "late" acyltransferases responsible for the linkage of acyloxyacyl chains, HtrB (LpxL or WaaM) and MsbB (LpxM or WaaN), prefer Kdo$_2$-lipid IV$_A$, and lipid IV$_A$ is the major component that accumulates in all mutants with defects in Kdo (either biosynthesis or transfer). Our data suggest that the late acyltransferases in *N. meningitidis* can act on lipid IV$_A$ substrates without a Kdo linkage. The late acyltransferases, HtrB and MsbB, may function prior to KdtA or the acyltransferases may have similar reactivity for both lipid IV$_A$ and Kdo$_2$ lipid IV$_A$. The only other example of incorporation of acyloxyacyl chains into lipid A prior to the addition of Kdo is found in *pseudomonas aeruginosa* (Goldman et al. 1991; Mohan et al., 1994). Inhibiting the function of the CMP-Kdo synthetase with a synthetic compound in *P. aeruginosa* results in inhibition of bacterial growth and accumulation of fully acylated lipid A. Lipid A from *P. aeruginosa* contains β-hydroxydecanoate (β-OHC10:0) at the 3 and 3' positions, β-hydroxylaurate (β-OHC12:0) at the 2 and 2' positions, and the acyloxyacyl chains are either laurate (C12:0) or β-hydroxylaurate, at the 2 and 2' positions. This symmetric acylation pattern is similar to that of meningococci. It is plausible that the incorporation of acyloxyacyl fatty acids takes place before Kdo glycosylation in gram-negative bacteria that synthesize lipid A with symmetric short chain fatty acids. In correlation with this observation, kdtA of *P. aeruginosa* is the most homologous gene when searching GenBank with the KdtA protein sequences of *N. meningitidis* (MC58 and Z24991).

The four major species of lipid A produced in the kdtA mutant differ in their phosphoryl substitution pattern at the 1 and 4' positions. Either a phosphate or a PEA group occupies the 4' positions of all four structures while the 1 (glycosidic) position is phosphorylated in two of the four structures (FIG. 14). Negatively charged groups at the 1 and 4' positions of the disaccharide are considered to be important for interaction with divalent cations such as $Mg^{+2}$ and $Ca^{+2}$, forming ionic bridges that link the LPS (LOS) molecules together. In some bacteria the 4' phosphate is missing or replaced by neutral sugars. Without wishing to be bound by theory, the negative charge at 4' position is proposed to be dispensable while the negative charge is necessary at the glycosidic position. Furthermore, the wild type strain NMB and five other LOS mutants derived from NMB with various outer core oligosaccharide compositions are all phosphorylated with either a phosphate or a PEA group at the glycosidic position (Kahler et al., 1998), while LOS from the wild type strain and the galE mutant are not phosphorylated at the 4' position (Rahman et al., 1998). It is intriguing that the lipid A from the meningococcal kdtA mutant is not phosphorylated at the glycosidic position.

The KdtA homologue of *E. coli* can functionally complement the meningococcal kdtA mutation. Meningococcal KdtA shares 39% amino acid sequence identity and 54% amino acid sequence similarity with the *E. coli* enzyme, and the *E. coli* KdtA enzyme has been shown to transfer Kdo residues to analogs of *E. coli* lipid A with various numbers of acyl chains (four to six) (Belunis et al., 1992). Since the meningococcal lipid A is symmetrically acylated on both glucosamines in contrast to that of *E. coli*, the location and length of fatty acids of lipid A appear not to be determinants of the substrate specificity for KdtA. Recently, KdtA from *Legionella pneumophila* has been shown to transfer Kdo residues to Lipid $IV_A$ of *E. coli* despite significant differences in their lipid A structures (Brabetz et al., 2000).

The tetrapac cell morphology of *N. meningitidis* expressing only lipid A is curious, since the meningococcal lpxA mutant which does not produce any lipid A is said to show a wild type morphology by electron microscopy (Steeghs et al., 1998). The tetrapac phenotype first described for the tpc mutation in *N. gonorrhoeae* is believed to result from a defect in murein hydrolase activity (Fusseneger et al., 1996). Although MurA, the UDP-N-acetylglucosamine 1-carboxyvinyltransferase involved in murein biosynthesis, is encoded downstream of kdta (FIG. 1C), we do not believe the tetrapac phenotype is due to a polar effect of the aphA-3 cassette. A ribosomal binding site and a ATG start codon following the kanamycin resistance gene are present in the aphA-3 cassette, and are fused in-frame to the remaining kdtA 3' coding sequence, therefore avoiding possible translational polar effects. Outer membrane structure changes triggered by the marked truncation of LOS may cause a compensatory reduction in murein hydrolase activity or other cell division enzymatic activities required for septum separation. The deficiency in natural transformation of the kdtA mutant is most likely caused by the altered membrane structure.

Several lipid A analogs, either chemically synthesized or isolated from bacteria such as *Rhodobacter sphaeroides* and *Rhodobacter capsulatus*, exhibit potent endotoxin antagonistic activities. In addition, foreign acyltransferases with altered fatty acid specificity can function in heterologous bacteria. For example, the β-hydroxymyristate chains at 3 and 3' positions of *E. coli* lipid A were replaced by β-hydroxylaurate and/or β-hydroxydecanoate when a meningococcal IpxA gene was used to complement a IpxA2 allele in *E. coli* (Odegaard et al., 1997). The finding that *N. meningitidis* can synthesize an intact lipid A without glycosylation suggests it can be a versatile expression system for assembly of diverse intact bacterial lipid A structures. The additional acid hydrolysis steps required for the removal of the inner core glycosyl linkage would be eliminated in the production of these intact lipid A structures.

Meningococci are naturally competent for transformation. This process involves DNA uptake and RecA-dependent recombination events. Pili and several other gene products have been shown to be required for transformation (Ryll et al., 1997). The psf mutant was not competent for transformation although pili were observed by electron microscopy. Psf is predicted to be a cytoplasmic protein; therefore, this pleiotropic effect in natural competence is most likely an indirect effect caused by some alternation of cell envelope not detected by EM analysis or Coomassie staining of membrane proteins. Techniques are available for the generation of stable insertion mutations in *N. meningitidis* and *N. gonorrhoeae*. Stephens and co-workers have described Tn916 mutagenesis of these neisserial species [Stephens et al. (1991) *Infect. Immun.* 59:4097-4102; Stephens et al. (1994) *Infect. Immun.* 62:2947-2952; Kathariou et al. (1990) *Mol. Microbiol.* 4:729-735]. Two types of insertion mutations occur: class I insertions appear to have an intact Tn916 element resulting from transposition of the transposon and class II insertions are characterized by deletion of part of the transposon with maintenance of the tetM element which confers tetracycline resistance. Insertions can be characterized in part with analysis of HaeIII-digested DNA in that Tn916 has no HaeIII sites, and the portion of the genome into which the transposon or tetracycline-resistance determining region has inserted by subcloning a HaeIII fragment with selection for antibiotic resistance. Flanking sequences can be used for sequence determination and/or for use in probe or primer for the isolation of the wild-type counterpart gene from the parental strain. When Tn916 is used to create the mutations in LOS-related genes, the Class II type of mutation is quite stable. Other types of stable mutations can be generated, including, but not limited to, deletion mutations, insertion mutations or multiple point mutations, and this may be accomplished by techniques including but not limited to oligonucleotide site-directed mutagenesis, polymerase chain reaction mutagenesis techniques, restriction endonuclease cutting and religation with or without insertion of heterologous DNA as appropriate for the type of mutation being created, as well known to one of ordinary skill in the art. The skilled artisan is capable of generating such alternate mutants using ordinary skill in the art; in particular, the DNA sequence information for kdtA, kdsB and kpsF are given in Tables 5-10 herein. The sequence information provided can be used to produce further mutations. It is preferred that where a transposon is used, that the resulting mutation itself is not an insertion which is further transposable. Alternatively, a selectable marker such as the aphA can be introduced by molecular biological techniques.

The skilled artisan recognizes that other corresponding neisserial strains including mutants of *N. gonorrhoeae* can produce lipid A with the distinguishing characteristics of a *N. meningitidis* kdtA, kdsB or psf mutant (Kdo-free, no oligosaccharides covalently linked to the Lipid A).

The meningococcal mutant LOS preparations were used to investigate the role of endotoxin structure on the activation of macrophages via the CD14/TLR4-MD-2 receptor complex. Endotoxins were quantified and standardized based on lipid A content. Cytokine (TNFa, IL-1b, IL-8 or IL-10) induction, nitric oxide and reactive oxygen species (ROS) release from differentiated U937 and THP-1 human macrophage-like cells or RAW264.7 murine macrophages stimulated with endotoxin (0.56 pmole/ml, approximately 1 ng/ml) was studied.

TNFa release from macrophage-like cells (differentiated from U937 and THP-1 human monocytes) was consistently 2 fold higher for meningococcal LOS than for equal molar amounts of *E. coli* LPS (0111:B4) ($P<0.0001$). TNFa release was similar when wild type meningococcal LOS (NeuNAc-Galb-GlcNAc-Galb-Glcb-Hep$_2$ (GlcNAc, Glca) PEA-KDO$_2$-lipid A; 1,4' bisphosphorylated), oligosaccharide altered meningococcal LOS {pgm (Hep$_2$ (GlcNAc) PEA-KDO$_2$-lipid A; 1,4' bisphosphorylated), rfaK (Hep$_2$ PEA-KDO$_2$-lipid A; 1,4' bisphosphorylated), and gmhX (KDO$_2$-lipid A; 1,4' bisphosphorylated)} and unsialylated meningococcal LOS, synA and 1st (Galb-GlcNAc-Galb-Glcb-Hep$_2$ (GlcNAc, Glca) PEA-KDO$_2$-lipid A; 1,4' bisphosphorylated) were used. Wild type meningococcal LOS and the LOS of these mutants also induced similar cytokine profiles for IL-8, IL-1b and IL-10 release. The kinetics of TNFa and other cytokine induction were similar in both dose-response and time-course assays.

In contrast, TNFa induction was attenuated approximately 5 fold for meningococcal lipid A of the KDO-deficient mutants kdtA (Lipid A; 1, 4' bisphosphorylated) and kpsF (Lipid A; 4'monophosphorylated) when equal molar amounts were used to stimulate macrophages ($P<0.0001$). No significant cytokine release was observed when differentiated U937 cells were exposed to a preparation from the LOS-deficient mutant (lpxA) ($P<0.0001$) extracted in a manner identical to the other LOS preparations. Meningococcal LOS-induced cytokine release was neutralized with 2 mg/ml of polymyxin B when added during the induction assay. The data indicate that cytokine release was due to meningococcal LOS and that KDO-deficient meningococcal LOS (Lipid A; 1,4' bis or 4' phosphorylated) showed significantly attenuated activity.

To confirm that the interaction of meningococcal LOS with macrophages was CD14 and TLR4-dependent, a monoclonal antibody to CD14 (when used alone or in combination with anti-TLR4-MD-2) was shown to abolish the effect of LOS cytokine induction in human THP-1 and U937 cells. Cells were pre-incubated with the antibodies before LOS challenge. The blocking of cytokine release by anti-CD14 ($P<0.000392$) and anti-TLR4 ($P<0.0042$) was dose-dependent. Thus, in both THP-1 and U937 cell lines, meningococcal LOS cytokine induction was mCD14 and TLR4 mediated.

The release of nitric oxide was similar from RAW macrophages stimulated with 0.56 pmole/ml of wild type meningococcal LOS or the truncated (mutant) meningococcal LOS preparations of the present invention. However, the KDO-deficient lipid A, kdtA (Lipid A; 1,4' bisphosphorylated) and kpsF (Lipid A; 4'monophosphorylated), showed 3 fold attenuated release of nitric oxide ($P<0.0001$). Similar differences in nitric oxide release were seen when RAW macrophages were indirectly stimulated with cell free supernatants from previously induced THP-1 cells. Nitric oxide release was dose-dependent for all meningococcal LOS structures tested. No response was seen in TLR4-deficient cells (C3H/HeJ) stimulated with purified meningococcal LOS. To further confirm the role of TLR4 and CD14, RAW macrophages were indirectly induced with supernatants from differentiated U937 cells or THP-1 cells previously blocked (prior to stimulation by LOS) with anti-CD14 or anti-TLR4-MD-2. Nitric oxide was not released. The data indicate that the attenuated activity of lipid A kdtA (Lipid A; 1,4' bisphosphorylaed) and kpsF (Lipid A; 4'monophosphorylated) is not species-specific because both lipid As have attenuated activity in human and murine cell lines.

To further assess meningococcal LOS-structure function relationships, oxidative burst of THP-1, U937 and RAW macrophages primed overnight with LOS was investigated using cellular chemiluminescence to measure the release of reactive oxygen species (ROS). No significant differences in ROS release were seen between glycosylated meningococcal LOS. However, the KDO-deficient lipid A (kdtA) and the LOS-deficient preparation (lpxA) showed significantly attenuated ROS release ($P<0.0002$). The results again indicate that oligosaccharide chain length does not affect meningococcal LOS priming of macrophages to release ROS, but that KDO-lipid A meningococcal structure was required for optimal agonist activity.

Figure 6C:
Figure 6D:
Figure 6A:
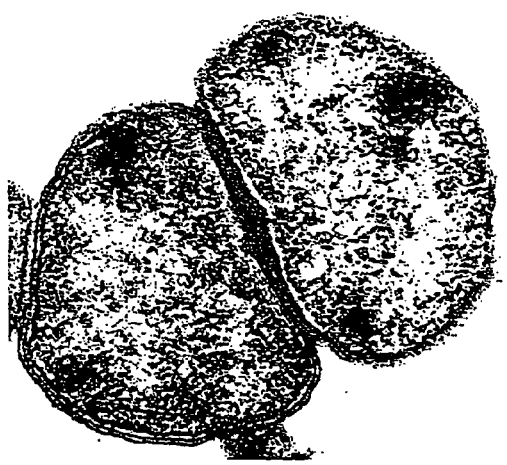
Figure 6B:

To determine that aggregation was not responsible for the differences observed between glycosylated and unglycosylated meningococcal LOS, latex beads were coated with dispersed meningococcal LOS and used to induce cellular responses. The phagocytosis of polystyrene beads immediately triggered an oxidative burst. However, wild type meningococcal LOS-coated beads significantly triggered higher amounts of ROS compared to KDO-deficient lipid A-coated beads ($P<0.001$) or beads coated with BSA alone ($P<0.0001$) (FIG. 6A). Similar results were seen when LOS-coated beads were used to stimulate RAW 264.7 macrophages for nitric oxide or THP-1 cells for TNFa release overnight. Taken together, these data confirm the role of KDO linked to lipid A in interaction with CD14/TLR4-MD-2 receptor complex and that the attenuated effect of unglycosylated lipid A was not due to aggregation.

Lipid A structures without KDO, produced by different mutations (kdtA and kpsF) in KDO biosynthesis or transfer, were poor stimulators of TNFa induction in THP-1 and U937 macrophages. Further, KDO-deficient lipid A also showed significantly attenuated activity in priming THP-1 macrophages for oxidative burst or for nitric oxide release by RAW macrophages. This indicated that KDO linked to lipid A was structurally required for optimal biological activity.

To further determine the importance of the KDO, LOS was subjected to mild acid hydrolysis to cleave KDO and the oligosaccharide from lipid A. Cytokines and nitric oxide release were significantly attenuated after LOS (NeuNAc-Galb-GlcNAc-Galb-Glcb-Hep$_2$ (GlcNAc, Glca) PEA-KDO$_2$-lipid A; 1,4' bisphosphorylated or KDO$_2$-lipid A; 1,4' bisphosphorylated) were subjected to acid hydrolysis when compared to controls ($P<0.0001$). The activity of hydrolyzed LOS was comparable to that of the KDO-deficient lipid A. LOS hydrolyzed with 1% acetic acid (pH 2.8) showed the greatest inhibition of TNFa release. Acid hydrolysis might affect lipid A phosphate head groups and contribute to attenuation. However, no significant difference in activity was seen between the KDO-deficient (Lipid A; 1,4' bisphosphorylated, Lipid A; 4'monophosphorylated) hydrolyzed and unhydrolyzed LOS ($P=0.083$). Synthetic KDO did not activate the CD14/TLR4-MD-2 receptor complex at dose ranges from 10 ng-100 mg (data not shown). These results support a role of KDO linked to meningococcal lipid A for optimal stimulation of macrophages via the CD14/TLR4-MD-2 receptor complex.

A competitive binding inhibition assay using glycosylated and unglycosylated LOS was performed to ascertain whether the attenuated activity of the KDO-deficient LOS (lipid A) was due to decreased binding to the CD14/TLR4-MD-2 receptor complex. $KDO_2$-lipid A ability to induce nitric oxide or TNFa was competitively inhibited by increasing concentrations of the unglycosylated lipid A. The addition of glycosylated ($KDO_2$-lipid A) and unglycosylated lipid A simultaneously to THP-1 macrophages resulted in a significant decrease in TNFa (P<0.001) release compared to $KDO_2$-lipid A alone. When RAW macrophages were stimulated with $KDO_2$-lipid A and unglycosylated lipid A together, intermediate levels of nitrite (15 mM) were detected in supernatants compared to $KDO_2$-lipid A alone (25 mM) or unglycosylated lipid A alone (6 mM). The incubation of glycosylated lipid A ($KDO_2$-lipid A) and unglycosylated lipid A (KDO-deficient lipid A) overnight, prior to cell induction resulted in a 50% decrease in nitric oxide release or TNFa release (2.7 ng/ml of TNFa with glycosylated meningococcal LOS compared to 1.3 ng/ml of TNFa with a mixture of glycosylated and unglycosylated LOS). These competitive inhibition assays suggested that glycosylated and unglycosylated lipid A bind equally well or share similar binding sites on the CD14/TLR4-MD-2 receptor complex.

Meningococcal LOS structures with penta-acylated lipid A [NMB-lpxL1, NeuNVAc-Galb-GlcNAc-Galb-Glcb-$Hep_2$ (GlcNAc, Glca) PEA-KDO-2-lipid A (pentaacylated); 1,4'bisphosphorylated; and gmhX-lpxL1, $KDO_2$-lipid A (pentaacylated); 1,4' bisphosphorylated] was used to induce cytokine, nitric oxide and ROS release from macrophages. Penta-acylated LOS induced ~70% TNFa activity (P<0.0003) when compared to the corresponding hexa-acylated LOS. By comparison £10% of the activity was retained with KDO-deficient hexa-acylated lipid A. Similar results were seen for nitric oxide or ROS release when cells were stimulated with penta or hexa-acylated LOS. The induction of TNFa was dramatically decreased (P<0.0001) to levels similar to those of the KDO-deficient lipid A when penta-acylated LOS was subjected to mild acid hydrolysis. Thus, loss of a fatty acyl chain from lipid A resulted in a modest reduction in biological activity. However, the loss of KDO from penta-acylated structure resulted in a dramatic attenuation in biologic activity.

Meningococcal LOS is a major inflammatory mediator. The interaction of meningococcal LOS with the CD14/TLR4-MD-2 receptor complex is predicted to result in macrophage activation and subsequent release of cytokines, chemokines, nitric oxide and reactive oxygen species. The goal of this study was to define the relationship of meningococcal LOS structure with the biological activity initiated through the CD14/TLR4-MD-2 receptor.

The importance of CD14 and TLR4-MD-2 in macrophage activation by meningococcal LOS was demonstrated. When CD14 was efficiently blocked with specific monoclonal antibody, TNFa production was abolished. When TLR4-MD-2 was blocked and CD14 available, a significant reduction in cytokine release was also observed. Highly purified LOS did not stimulate TLR2 in our experimental models, supporting the model that CD14/TLR4-MD-2 is the sole meningococcal LOS receptor complex. Meningococcal LOS like enteric LPS (da Silva, 2001) is likely transferred from the LBP-sCD14 complex to membrane bound CD14/TLR4-MD-2 and meningococcal LOS is in close proximity to each of the proteins in the complex.

Variability in meningococcal LOS oligosaccharide structure and length had no effect on CD14/TLR4-MD-2 receptor complex activation. However, KDO-linked to lipid A was required for maximal activation. Results consistent with this model were seen with cytokine induction, nitric oxide or ROS release and in time-course or dose-response studies. The importance of KDO-lipid A was confirmed when meningococcal LOS was subjected to mild acid hydrolysis to cleave KDO from lipid A. The loss of KDO attenuated meningococcal LOS activity dramatically.

The importance of KDO-lipid A for meningococcal endotoxin biological activity is also seen with enteric LPS. Schromm et al. (1998) reported that the number, nature, and location of negatively charged molecules including KDO strongly modulates the molecular conformation of *E. coli* lipid A and is linked to IL-6 inducing capacity. Recently, synthetic lipid A with two KDO molecules was found to have enhanced agonist activity compared to one KDO molecule or none (Yoshizaki, 2001; Kusumoto, IES meeting, personal communication, 2002). In our study, acid hydrolysis to remove KDO from lipid A resulted in dramatic attenuation in meningococcal LOS biological activity. This effect was seen with mild acid hydrolysis which does not alter lipid A structure or cleave lipid A phosphate head groups (Zhou, 1998). Meningococcal KDO-lipid A was recognized by the CD14/TLR4-MD-2 receptors of both human and murine cells. Thus, the KDO structural requirement for meningococcal LOS was not a determinant of the species-specific difference noted with other LPS structures (Tanamoto, 2000; Lien, 2000).

While KDO-linked lipid A was essential for maximal CD14/TLR-4-MD-2 activation by meningococcal LOS, the negatively charged lipid A phosphate head groups appear to play a minor role. Monophosphorylated meningococcal KDO-deficient lipid A was minimally less active than the bisphosphorylated meningococcal lipid A. Meningococcal LOS hydrolysis with very harsh acid conditions attenuated biological activity more than mild acid hydrolysis. The low pH dependent hydrolysis could be due to loss of phosphate head groups. Phosphate and PPEA affects endotoxic activity (Rietschel, 1994; Loppnow, 1989) and the ability of meningococcal LOS to clot *limulus amebocyte* lysate appears related to the amount of bisphosphorylated lipid A expressed by meningococcal isolates (Roth, 1992). Hexa-acylated *E. coli* lipid A with 2 phosphate groups is predicted to be more reactive than less negatively charged lipid A (Frecer, 2000a; Frecer, 2000b).

Meningococcal fatty acyl chain number was also a contributor to macrophage activation via the CD14/TLR4-MD-2 receptor. Meningococcal LOS with penta-acylated lipid A but otherwise intact oligosaccharide structure showed an approximately 30% reduction in TNFα inducing activity compared to the corresponding hexa-acylated lipid A. The attenuation in agonist activity of LOS with penta-acyl lipid A was seen in both human and murine macrophages. Van der Lay (2001) showed that a penta-acylated meningococcal mutant (lpxL1) had reduced toxicity as measured in a TNFa induction assay. Several studies have shown that the number and nature of fatty acyl chains in lipid A are important determinants of biological activity (Tanamoto, 2000; Nurminen, 1985; Rund, 1999; Gangloff, 1999; Salimath, 1983; Plotz, 2000; Zahringer, 1995; Suda, 2001; Matsuyama, 2001). For example, synthetic tetra-acylated lipid A (lipid IVa) is an antagonist of LPS activation of human macrophages (Luderitz, 1984; Galanos, 1984) and penta-acylated LPS extracted from *P. gingivalis* containing extended and branched fatty acyl chains has attenuated activity (Ogawa, 2002; Hirschfield, 2001). It is noted that the LOS from the KdtA-deficient mutant *N. meningitidis* is a weak agonist, some thousand fold weaker than wild-type LOS in eliciting TNFα from macrophages.

Seydel (2000) has proposed that the biological activity of endotoxin is determined by the three dimensional structure of lipid A. Lipid A with a "conical/concave shape", (the cross-section of the hydrophobic region being larger than that of the hydrophilic region), exhibited strong IL-6-inducing activity. A "cylindrical molecular shape" of lipid A correlated with antagonistic activity. Hawkins et al (2002) using synthetic simplified structures of lipid A, showed that the chirality of the molecule plays an important role in activity. Synthetic lipid A (isomers) with R,R,R,R-acyl chain configuration was strongly agonistic, whereas similar compounds with R,S,S, R-acyl chain configuration were much weaker in biological activity. Changes in fatty acyl chains like saturation or removal of β-keto group as well as the length of the link between the acyl chains directly influenced biologic activity.

A polynucleotide or fragment thereof is substantially homologous (or substantially similar) to another polynucleotide if, when optimally aligned (with appropriate nucleotide insertions or deletions) with another polynucleotide, there is nucleotide sequence identity for approximately 80% of the nucleotide bases, usually approximately 90%, more preferably about 95% to 100% of the nucleotide bases.

Alternatively, substantial homology (or similarity) exists when a polynucleotide or fragment thereof will hybridize to another polynucleotide under selective hybridization conditions. Selectivity of hybridization exists under hybridization conditions which allow one to distinguish the target polynucleotide of interest from other polynucleotides. Typically, selective hybridization will occur when there is approximately 75% similarity over a stretch of about 14 nucleotides, preferably approximately 80% similarity, more preferably approximately 85% similarity, and most preferably approximately 90% similarity. See Kanehisa (1984) *Nucl. Acids Res.* 12:203-213. The length of homology comparison, as described, may be over longer stretches, and in certain embodiments will often be over a stretch of about 17 to 20 nucleotides, preferably 21 to 25 nucleotides, more preferably 26 to 35 nucleotides, and more preferably about 36 or more nucleotides.

The hybridization of polynucleotides is affected by such conditions as salt concentration, temperature, or organic solvents, in addition to the base composition, length of the complementary strands, and the number of nucleotide base mismatches between the hybridizing polynucleotides, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1 M, typically less than 500 mM, and preferably less than 200 mM. However, the combination of parameters is much more important than the measure of any single parameter (Wetmur and Davidson (1968) *J. Mol. Biol.* 31:349-370).

An isolated or substantially pure polynucleotide is a polynucleotide which is substantially separated from other polynucleotide sequences which naturally accompany a native sequence. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide of a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter affects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate non-exemplified LOS biosynthetic protein coding sequences. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a protein of interest or a fragment thereof can be incorporated into recombinant polynucleotide constructs, typically DNA constructs, capable of introduction into and replication in a prokaryotic or eukaryotic cell. Usually the construct will be suitable for replication in a unicellular host, such as yeast or bacteria, but a multicellular eukaryotic host may also be appropriate, with or without integration within the genome of the host cells. Commonly used prokaryotic hosts include strains of *Escherichia coli*, although other prokaryotes, such as *Bacillus subtilis* or *Pseudomonas* may also be used. Mammalian or other eukaryotic host cells include yeast, filamentous fungi, plant, insect, amphibian and avian species. Such factors as ease of manipulation, ability to appropriately glycosylate expressed proteins, degree and control of protein expression, ease of purification of expressed proteins away from cellular contaminants or other factors may determine the choice of the host cell.

The polynucleotides may also be produced by chemical synthesis, e.g., by the phosphoramidite method described by Beaucage and Caruthers (1981) *Tetra. Letts.* 22:1859-1862 or the triester method according to Matteuci et al. (1981) *J. Am. Chem. Soc.* 103:3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence. Polymerase chain reaction technologies are well known to the art. See, for example, Innis et al. (1990) *PCR Protocols*, Academic Press; U.S. Pat. Nos. 4,683,195; 4,683,202; 4,800,159; Saiki et al. (1985) *Science* 230:1350-1354.

DNA constructs prepared for introduction into a prokaryotic or eukaryotic host typically comprise a replication system (i.e. vector) recognized by the host, including the intended DNA fragment encoding the desired polypeptide, and preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1993) *Current Protocols in Molecular Biology*, Greene Publishing and Wiley Interscience, New York; and Metzger et al. (1988) *Nature,* 334: 31-36. Many useful vectors for expression in bacteria, yeast, mammalian, insect, plant or other cells are well known in the art and may be obtained such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, among others; (b) complement auxotrophic deficiencies; or (c) supply critical nutrients not available from complex media. The choice of the proper selectable marker will depend on the host cell; appropriate markers for different hosts are known in the art.

The recombinant vectors containing the LOS biosynthetic gene (or mutant gene) sequence of interest can be introduced into the host cell by any of a number of appropriate means, including electroporation; transformation or transfection employing calcium chloride, rubidium chloride, calcium phosphate, DEAE-dextran, or other substances; microprojectile bombardment; lipofection; and transfection or infection (where the vector is an infectious agent, such as a viral or retroviral genome). The choice of such means will often depend on the host cell. Large quantities of the polynucleotides and polypeptides of the present invention may be prepared by transforming suitable prokaryotic or eukaryotic host cells with LOS-related polynucleotides of the present invention in compatible vectors or other expression vehicles and culturing such transformed host cells under conditions suitable to attain expression of the desired Lipid A or LOS structure. The derivative Lipid A may then be recovered from the host cell and purified.

When it is desired to eliminate leader sequences and precursor sequences at the 5' side of the coding sequence, a combination of restriction endonuclease cutting and site-directed mutagenesis via PCR using an oligonucleotide containing a desired restriction site for cloning (one not present in coding sequence), a ribosome binding site, a translation initiation codon (ATG) and the codons for the first amino acids of the mature protein. The oligonucleotide for site-directed mutagenesis at the 3' end of the coding sequence includes nucleotides encoding the carboxyterminal amino acids of the protein, a translation termination codon (TAA, TGA or TAG), and a second suitable restriction endonuclease recognition site not present in the remainder of the DNA sequence to be inserted into the expression vector. The site-directed mutagenesis strategy is similar to that of Boone et al. (1990) *Proc. Natl. Acad. Sci. USA* 87, 2800-2804, as modified for use with PCR.

In another embodiment, polyclonal and/or monoclonal antibodies capable of specifically binding to a particular LOS or Lipid A molecule (or fragments thereof) are provided. The term antibody is used to refer both to a homogenous molecular entity and a mixture such as a serum product made up of a plurality of different molecular entities. Monoclonal or polyclonal antibodies, preferably monoclonal, specifically reacting with Lipid A or a LOS of a particular phenotype of interest may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice,* 2d ed., Academic Press, New York; and Ausubel et al. (1993) supra. Also, recombinant immunoglobulins may be produced by methods known in the art, including but not limited to, the methods described in U.S. Pat. No. 4,816,567, incorporated by reference herein. Monoclonal antibodies with affinities of $10^8 M^{-1}$, preferably $10^9$ to $10^{10}$ or more are preferred.

Antibodies generated against Lipid A or a LOS phenotype of interest are useful, for example, as probes for screening DNA expression libraries or for detecting the presence of particular mutant neisserial strains in a test sample. Hydrophilic regions of LOS biosynthetic enzymes can be identified by the skilled artisan, and peptide antigens can be synthesized and conjugated to a suitable carrier protein (e.g., bovine serum albumin or keyhole limpet hemocyanin) for use in vaccines or in raising antibody specific for LOS biosynthetic proteins. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. United States Patents describing the use of such labels include but are not limited to U.S. Pat. Nos. 3,817,837; 3,850,752; 3,939,350; 3,996,345; 4,277,437; 4,275,149; and 4,366,241.

Antibodies specific for Lipid A or particular LOS variants and capable of inhibiting adherence of Lipid A-expressing or LOS (wild-type)-expressing neisserial cells to host tissue are be useful in preventing diseases resulting from neisserial infections. Such antibodies can be obtained by the methods described above.

Compositions and immunogenic preparations including vaccine compositions comprising substantially purified Kdo-free Lipid A or a mutant LOS and a suitable carrier therefor are provided. Alternatively, hydrophilic regions of the LOS biosynthetic proteins can be identified by the skilled artisan, and peptide antigens can be synthesized and conjugated to a suitable carrier protein (e.g., bovine serum albumin or keyhole limpet hemocyanin) for use in vaccines or in raising antibody specific for LOS-expressing neisserial strains. Immunogenic compositions are those which result in specific antibody production when injected into a human or an animal.

Such immunogenic compositions are useful, for example, in immunizing a humans, against infection by neisserial pathogenic strains. The immunogenic preparations comprise an immunogenic amount of, as specifically exemplified, at least one Lipid A molecule or lipooligosaccharide preparation derived from a N. meningitidis strain in which there is a disruption in at least one of the psf, kdsB and kdtA genes, preferably a nonpolar mutation and a suitable carrier. The kdsB, kdtA or psf mutation can be introduced into strains of serotypes B, C, W-135 or Y. Alternatively, the immunogenic composition can comprise cells of at least one of the specifically exemplified N. meningitidis NMB206, NMB249 or NMB259 or other N. meningitidis mutant and a suitable carrier. It is understood by one of ordinary skill in the art that other, functionally equivalent, strains of *N. meningitidis*, for example, NMB, can be produced by the introduction of the cloned DNA containing the insertion mutations responsible for the phenotypes of the 206, 249 and 259 mutants. It is also within the scope of the present invention and readily within the grasp of the ordinary skilled artisan to generate other types of genetically stable mutations in the psf and/or kdsB and/or kdtA genes of *N. meningitidis* and/or *N. gonorrhoeae*. Such immunogenic compositions (or vaccines) are useful, for example, in immunizing an animal, especially humans, against neisserial disease resulting from infection by pathogenic neisserial species, particularly *Neisseria gonorrhoeae* and *Neisseria meningitidis*. Such compositions can also serve as immunological adjuvants when combined with an antigen of interest and a suitable pharmaceutical carrier.

Because of the interactions of the mutant LOS preparations described herein with cytokine producing cells, e.g., macrophages and macrophage-like cells, these preparations are useful in modulating the immune response, for example, to skew an immune response to an immunogenic composition containing the preparation and at least one antigen of interest, toward a humoral (antibody) response. The mutant *N. meningitidis* cells themselves can be incorporated into an immunogenic composition, for example, a vaccine containing *Haemophilus influenzae*, among others. Virtually any antigenic preparation where an antibody response is sought can be used.

Another application of the mutant LOS preparations of the present invention is as competitive inhibitors of endotoxin, for example, in a patient suffering from endotoxin shock or a systemic (or other serious) Gram negative bacterial infection. A mutant LOS of the present invention is incorporated into a sterile formulation together with a pharmaceutically acceptable carrier or excipient and administered to the patient at a dosage sufficient to provide a level in the bloodstream from about 1 to about 1000 μg/ml.

Such immunogenic compositions can also elicit the production of antibodies which cross react with LOS of *Haemophilus influenzae* strains expressing Lipid A epitopes in common with those of the starting *N. meningitidis* strain(s). The immunogenic preparations comprise an immunogenic amount of a non wild-type lipooligosaccharide from strain of *N. meningitidis* or *N. gonorrhoeae*, or an immunogenic fragment thereof, or of cells of one or more neisserial strains which lack an intact lipooligosaccharide or other antigen to which an immune response is desired. Such immunogenic compositions advantageously further comprise lipooligosaccharide(s) or neisserial cells of one or more other serological types, including but not limited to any known to the art. It is understand that where whole cells are formulated into the immunogenic composition, the cells are preferably inactivated, especially if the cells are of a virulent strain. Such immunogenic compositions may comprise one or more additional LOS preparations, or another protein or other immunogenic cellular component. By "immunogenic amount" is meant an amount capable of eliciting the production of antibodies directed against neisserial LOS biosynthetic proteins and against an antigen of interest in an animal or human to which the vaccine or immunogenic composition has been administered.

Immunogenic carriers may be used to enhance the immunogenicity of the Lipid A, LOS or *N. meningitidis* of attenuated virulence. Such carriers include, but are not limited to, proteins and polysaccharides, liposomes, and bacterial cells and membranes. Protein carriers may be joined to the Lipid A or LOS molecules to form fusion proteins by recombinant or synthetic means or by chemical coupling. Useful carriers and means of coupling such carriers to polypeptide antigens are known in the art. The art knows how to administer immunogenic compositions so as to generate protective immunity on the mucosal surfaces of the upper respiratory system, especially the mucosal epithelium of the nasopharynx, where immunity specific for *N. meningitidis* and for the remainder of the respiratory system, particularly for *H. influenzae*, and for the epithelial surfaces of the genito-urinary tract, particularly for *N. gonorrhoeae*, is most helpful.

Because of the interactions of the mutant LOS preparations of the present invention with cytokine producing cells, especially macrophages and macrophage-like cells, these preparations are useful in modulating the immune response to at least one antigen in an immunogenic composition (containing LOS) toward a humoral (antibody) response. The mutant *N. meningitidis* cells themselves can be incorporated into an immunogenic composition or the mutant LOS preparation can be formulated with antigen preparations, for example, from *Haemophilus influenzae* B, among others. Virtually any antigenic preparation where a predominantly antibody response is sought can be used in formulations with these LOS preparations.

Another application for the mutant LOS preparations of the present invention is as competitive inhibitors of endotoxin, for example, in a patient suffering from endotoxin shock or sepsis (or other serious infection) caused by a Gram negative bacterium. The mutant LOS of the present invention is incorporated in a sterile formulation with a pharmaceutically acceptable carrier or excipient and administered in a dose sufficient to modulate the deleterious physiological response to the endotoxin resulting from the infection. The mutant LOS can be administered, for example, intravenously, to achieve a concentration of the mutant LOS in the bloodstream at a concentration of from about 1 to about 1000 μg/ml.

The immunogenic compositions of the present invention may be formulated by any of the means known in the art. Such vaccines are typically prepared as injectables, either as liquid solutions or suspensions. Solid forms suitable for solution in, or suspension in, liquid prior to injection may also be prepared. The preparation may also, for example, be emulsified, or the protein encapsulated in liposomes.

The active immunogenic ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to:

aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A referred to as MTP-PE); and RIBI, which contains three components extracted from bacteria, monophosphoryl lipid A, trehalose dimycolate and cell wall skeleton (MPL+TDM+CWS) in a 2% squalene/TWEEN 80 (trademark of ICI Americas Inc.) emulsion. The effectiveness of an adjuvant may be determined by measuring the amount of antibodies directed against the immunogen resulting from administration of the immunogen in vaccines which are also comprised of the various adjuvants. Such additional formulations and modes of administration as are known in the art may also be used.

Mutant Lipid A or LOS and/or cells producing mutant LOS and/or Kdo-free Lipid A fragments thereof may be formulated into immunogenic compositions as neutral or salt forms. Preferably, when cells are used they are of attenuated or avirulent strains, or the cells are killed before use. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylamino-ethanol, histidine, and procaine.

The immunogenic Lipid A or LOS preparations (or peptide antigens related thereto) compositions are administered in a manner compatible with the dosage formulation, and in such amount as will be prophylactically and/or therapeutically effective. The quantity to be administered, which is generally in the range of about 100 to 1,000 µg of protein, LOS or Lipid A per dose, more generally in the range of about 1 to 500 µg of protein per dose, depends on the subject to be treated, the capacity of the individual's immune system to synthesize antibodies, and the degree of protection desired. Precise amounts of the active ingredient required to be administered may depend on the judgment of the physician and may be peculiar to each individual, but such a determination is within the skill of such a practitioner.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., at 1 to 4 months for a second dose, and if needed, a subsequent dose(s) after several months.

All references cited herein are hereby incorporated by reference in their entireties to the extent that there is no inconsistency with the present disclosure.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1-4, Plenum Press, New York. Abbreviations and nomenclature, where employed, are deemed standard in the field and commonly used in professional journals such as those cited herein.

The foregoing discussion and the following examples are provided for illustrative purposes, and they are not intended to limit the scope of the invention as claimed herein. Modifications and variations which may occur to one of ordinary skill in the art are within the intended scope of this invention.

EXAMPLES

Example 1

Materials and Bacterial Strains

Bacterial strains and plasmids used in this study are described in Table 1. Monoclonal antibodies for meningococcal serogroup B (2-2-B), C (4-2-C), Y (5-2-Y) and W-135 (7-1-W) capsular polysaccharides were kindly provided by Dr. Wendell Zollinger (Water Reed Army Institute of Research, Washington D.C.). Monoclonal antibody M2 against Flag epitope and antibiotics were obtained from Sigma Chemical Co., St. Louis, Mo. Restriction enzymes were purchased from New England Biolabs, Beverly, Mass. Polyclonal antiserum to the Psf protein was raised in rabbits (Covance Research Products, Inc.).

The *E. coli Neisseria* shuttle vector was constructed as follows: the approximately 4 kb fragment of gonococcal cryptic plasmid was released from pEG2 (Christodoulides et al., 2000) by HindIII digestion, purified by agarose gel electrophoresis, and cloned into the unique HindIII site of a plasmid derivative of pCR2.1 in which the ampicillin resistance gene has been deleted by BsaI and ScaI digestion. The resulting plasmid, pYT237, was then cut with HbaI and NcoI to remove kanamycin resistance gene. The vector fragment was purified, treated with Klenow polymerase, and then ligated with an EcoRI fragment (blunted with Klenow polymerase) of an erythromycin resistance gene, ermC, obtained from pAermC'G (Zhou et al., 1996) to yield pYT250.

Example 2

Growth Conditions

Meningococcal strains were grown with 3.5% $CO_2$ at 37° C. unless specified otherwise. GC base agar (Difco Laboratories, Detroit, Mich.), supplemented with 0.4% glucose and 0.68 mM $Fe(NO_3)_3$, or GC broth (per liter: 15 g protease peptone, 4 g $K_2HPO_4$, 1 g $KH_2PO_4$, and 5 g NaCl) with same supplements and 5.1 mM $NaHCO_3$ was used. BHI medium (37 g/l brain heart infusion) with 1.25% fetal bovine serum (Gibco BRL) was used when kanamycin selection was required. Antibiotics concentrations (in µg/ml) used for *E. coli* strains were ampicillin, 100, kanamycin, 50, spectinomycin, 100, and erythromycin, 300; and for *N. meningitidis* were kanamycin, 80, spectinomycin, 60, erythromycin, 3, and tetracycline, 5. *E. coli* strain DH5α cultured on Luria Bertani (LB) medium was used for cloning and propagation of plasmids.

Meningococci were transformed by the procedure of Janik et al. (Janik et al., 1976), *E. coli* strains were transformed by electroporation with a GenePulser (BioRad, Hercules, Calif.) according to the manufacturer's protocol.

Example 4

DNA Preparation

Plasmids were purified using Qiaprep spin miniprep kit (Qiagen) and PCR products with Qiaquick purification kit (Qiagen, Valencia, Calif.). Chromosomal DNA was isolated by the method of Nath (Nath, 1990). Restriction fragments resolved by 1% agarose gel were purified using a Qiaquick gel extraction kit (Qiagen, Valencia, Calif.).

Example 5

Construction of Meningococcal Nonpolar Mutants psf: An internal 793-bp fragment of psf (NMB0352) was produced by PCR amplification using primers YT60 (CGA CTG GGC ACG CGA AGT GTT GC) (SEQ ID NO:2) and YT61 (GCA TGA CTT CGT CTA TCG AAA GAC CGG) (SEQ ID NO:3), and cloned into pCR2.1 to yield pYT203. A SmaI-digested aphA-3 cassette (Menard et al., 1993) or Ω(Spec) cassette (Prentki and Krisch, 1984) was subsequently inserted into the unique AscI site (blunted with Klenow) to generate pYT206 and pYT205 respectively. ScaI-linearized plasmids were used to transform meningococcal strain NMB. No polar Ω(Spec) mutation was created in psf, presumably because of the presence of downstream essential genes. The correct homologous recombination of the aphA-3 cassette into NMB0352 was confirmed by PCR.

kdsB: The NMB0675 (kdsB) sequence from the MC58 genome (Tettelin et al., 2000) was used to design primer YT84 (5'-GACAGGTTGGGAAAAGGCATCAGA-3') (SEQ ID NO:4), located upstream of kdsB, and 3' primer YT85 (5'-GTTCCGGCACGTATCGCATCAC-3') (SEQ ID NO:5). A 746 bp PCR product was amplified from chromosomal DNA of strain NMB using Vent DNA polymerase (New England Biolabs), phosphorylated with T4 kinase, then cloned into HincII-SmaI digested pUC18 to yield pYT256. The aphA-3 cassette released by SacI-HindIII digestion was subsequently inserted into the unique EcoRV site within kdsB to generate pYT259. Colony PCR using KanC (3' of aphA-3 cassette, Kahler et al., 1996) and YT85 primers confirmed the correct insertion of the cassette. ScaI-digested pYT259 was used to transform strain NMB, and kanamycin resistant colonies were selected at 30° C.

tal: PCR amplification using Primers YT68 (5'-CAGGGCGTGTGCGGCGTAACTTC-3') (SEQ ID NO:6) and YT69 (5'-CGTAGAGCGTGTCGGGATAGGC-3') (SEQ ID NO:7) and NMB chromosomal DNA as template yielded a 715 bp internal fragment of tal, and the PCR product was subsequently cloned into pCR2.1 by TA-cloning. A unique ClaI site was used to insert the aphA-3 cassette released by EcoRI-BamHI double digestion and blunted with Klenow. The resulting plasmid, pCAS5, with correct orientation and in-frame fusion of the aphA-3 in tal was linearized with ScaI digestion and used for transforming meningococcal strain NMB to generate the CAS5 mutant.

kdtA: The construction of this mutant has been achieved as follows: A 1476 bp PCR product was amplified from chromosomal DNA of meningococcal strain NMB using 5' primer YT82 and 3' primer YT81. This PCR product was cloned into pCR2.1 using TA-cloning kit (Invitrogen). The insert was released with EcoRI digestion and then subcloned into EcoRI site of pUC18 to yield pYT243. A fragment (754 bp) within the kdtA sequence of pYT243 was removed by BssHII digestion and the remaining vector was gel-purified and blunted with Klenow. The aphA-3 (Km$^r$) cassette released by SmaI digestion from pUC18K was subsequently inserted into pYT243. The orientation of aphA-3 cassette was determined by colony PCR analysis with primers KanC (3' end of aphA-3 cassette) and YT81, and a transformant with correct insertion was saved (pTY249). The in-frame fusion of aphA-3 cassette with kdtA was confirmed by automatic fluorescent sequencing. Meningococcal strain NMB was transformed with ScaI-linearized pYT249 and allelic exchange yielded kanamycin resistant colonies, which were further confirmed by colony PCR analyses to contain the kdtA::aphA-3 mutation.

Example 6

Overexpression and Purification of the Meningococcal Psf Protein

The coding sequence of Psf was amplified with 5' primer YT70 (5'-GGCGGATGCATATGGCAGAAAACGG-3' (SEQ ID NO:8), NdeI site underlined) and 3' primer YT71 (5-TTTGTTAATCTCGAGTACAATCCGTGCCG-3' (SEQ ID NO:9), XhoI site underlined) using meningococcal chromosomal DNA as template. The PCR product was digested with NdeI and XhoI and then ligated into pET20b(+) which had been digested with the same enzymes, yielding pYT225. The plasmid was purified and transformed into the *E. coli* expression strain, BLR2I(DE3)pLysS. One liter of LB culture of the Psf overexpression strain was induced at $OD_{600}$ of 0.4 with 1 mM IPTG for 16 hours. The harvested cells were resuspended in 15 ml of lysis buffer (50 mM Na phosphate, pH 8.0; 300 mM NaCl, 10 mM imidazole; 1 mM PMSF) and sonicated 30 seconds for each of 10 times, with 30 seconds cooling intervals. The cell debris was removed by centrifugation at 14,000 g for 15 minutes. The crude extract was then incubated with 2 ml of a 50% suspension of Ni-NTA resin (Qiagen) for 2 hours before packing into a column. The column was washed with 10 ml each of 20 mM and 50 mM imidazole in lysis buffer, then eluted with 10 ml of 250 mM imidazole. The fractions were pooled after SDS-PAGE analysis, concentrated by centrifugation through a Centricon 3 filter (Amicon, Bedford, Mass.) and dialyzed against storage buffer (50 mM HEPES, pH 7.5, 100 mM NaCl, 5 mM $MgCl_2$, 1 mM EDTA). Protein concentrations was determined by Bradford assay (BioRad, Hercules, Calif.) with bovine serum albumin as standard.

Example 7

Complementation of the psf and kdtA Mutants

A plasmid containing an intact copy of the meningococcal psf coding sequence transcribed under the control of the lac promoter, and the ermC gene inserted downstream of psf was constructed. Full-length pdg was amplified with primer CAS 1 (5'-TTACAGCAAAGCTTGATGGCAATGGC-3' (SEQ ID NO: 10), HindIII site underlined) and CAS2 (5'-TTTGT GGATCCACTATACAATCCGTG-3' (SEQ ID NO: 11), BamHI site underlined). The PCR product was digested with HindIII and BamHI and cloned into pEGFP cut with the same enzymes. An erythromycin resistance cassette (ermC)

obtained from pAErmC'G (Zhou and Apicella, 1996) by EcoRI digestion was subsequently cloned downstream of the psf gene using SmaI-EcoRI sites. This psf/ermC construct was amplified by PCR with primers CAS4 (5'-CGCCTCTC-CCCGCGCGTTGGCCG-3') (SEQ ID NO: 12) and YT59 (5'-CGGCCGACTAGTAGGCCTATTATTTTTG-3') (SEQ ID NO: 13), then cloned into the unique HincII site within a 1 kb chromosomal sequence of the meningococcal 120A1 locus, which is located about 85 kb from the psf locus, in pYT109. Transformation and homologous recombination of the flanking sequences of the 120A1 locus introduce the psf/ermC fragment into this site and result in erythromycin resistant transformants. Subsequently, a PCR product (primers YT69 and CAS3, Table 3 and FIG. 1) encompassing the sequence flanking the entire psf coding sequence with the aphA-3 insertion within psf was amplified from the chromosomal DNA of the NMB206 mutant and used to transform this strain. $Erm^B/Kan^B$ transformants were then selected. A panel of PCR analyses and Southern blots with the aphA-3 cassette and the psf internal fragment (YT60-YT61) as probes confirm that allelic exchange of the aphA-3 cassette occurred at the wild type psf locus and the second copy of psf at the 120A1 locus was intact.

In order to complement the kdtA defect in NMB249, primers YT91 and YT92 were used to amplify the coding sequence of kdtA from chromosomal DNA of the meningococcal strain NMB; while primer YT93 and YT94 was used to obtain kdtA from E. coli K12 strain DH5α. The amplicons were digested with HindIII and BglII, and then ligated with pCTC-Flag (Sigma Chemical Co.) which has been cut with the same enzymes. The resulting plasmids, pYT268 and pYT269, rendered kdtA of N. meningitidis and E. coli respectively under the control of a tac promoter and fused with an octapeptide Flag tag. A ~4.6 kb fragment containing lacI, tac promoter and the kdtA coding sequence was released from pYT268 by BglI digestion, blunted with Klenow, and subcloned into the EcoRV site of a shuttle vector, pYT250, to generate pYT271. Because of the presence of a BglI site within the E. coli kdtA coding sequence, the same fragment was amplified from pYT269 by PCR using Vent polymerase (New England Biolabs) and primers YT80 and YT83. The PCR product was phosphorylated with T4 kinase and cloned into the EcoRV site of pYTD250 to yield pYT274.

Plasmids for complementation were first methylated by HaeIII methylase (New England Biolab) according to the manufacturer's protocol, and the reaction mixture was used directly for transformation. Transformation of a meningococcal strain NMB was done by following the procedure of Janik et al., 1976. Erythromycin resistant transformants were selected and colony PCR using vector-specific primers YT79 and YT80 confirmed the presence of the plasmid-encoded kdtA. The strains carrying pYT271 and pYT274, termed NMB271 and NMB274, were subsequently transformed with linearized pYT249, and transformants with both erythromycin and kanamycin resistance were selected.

Meningococcal chromosomal DNA was prepared according to the method of Nath. The Genius 2 DNA labeling and detection system (Boehringer Mannheim, Indianapolis, Ind.) was used to perform DNA hybridization. The digoxigenin labeled probe for detecting kdtA was generated by a random primed labeling reaction with the YT81-YT82 PCR product as template, and the probe for aphA-3 cassette was made from purified cassette fragment released from the pUC18k by SmaI restriction. Chromosomal DNA was digested by PvuII overnight and resolved on a 0.7% agarose gel. DNA was transferred to a nylon membrane using a Turboblotter apparatus (Schleicher & Schuell, Keene, N.H.). Hybridization and development of the Southern blots were performed following the manufacturer's protocol.

Example 8

Cloning of the K1 E. coli psf Homologue

Primers YT77 (5'-GTGCAAAGGGAATTCTATGTCT-GAAAGAC-3' (SEQ ID NO: 14), EcoRI site underlined and start codon in boldface type) and YT78 (5'-CGTTGCT AGATCTGTCGAAAATGCGCAC-3' (SEQ ID NO: 15), BglII site underlined) were used to amplify psf from K1 E. coli strain EV36 (Vimr and Troy, 1985) to give a 1010 bp PCR product. The PCR fragment was digested with EcoRI and BglII and ligated with pFlag-CTC (Sigma), which has been cut with the same enzymes. Psf was produced under the control of the tac promoter and was fused to the Flag octapeptide epitope coding sequence in the resulting plasmid, pYT239. A 4.3 kb fragment, which contains the lacI repressor gene and the cloned psf, was released by Bg/I digestion and then subcloned into the EcoRV site of a meningococcal shuttle vector, pYT250 to yield pYT240. The psf coding sequence with an in-frame Flag fusion was confirmed with DNA sequencing analysis. The Psf-encoding plasmid was methylated with HaeIII methylase according to a published procedure (Christodoulides et al., 2000) prior to transformation into meningococci. Erythromycin resistant transformants were analyzed for the presence of the E. coli psf gene by colony PCR.

Example 9

LOS Extraction and Characterization

Twelve liters of overnight (stationary phase) cultures of meningococci were harvested by centrifugation at 10,000×g for 15 minutes. The combined cell pellet was dried in a SpeedVac (Thermo Savant, Holbrook, N.Y.) overnight and the dry weight was measured. The dried pellet was then extracted (1 g/10 ml) with phenol:chloroform:petroleum ether (2:5:8) as described by Kahler et al. (Kahler et al., 1996). The LOS samples were analyzed with 16.5% Tricine SDS-PAGE followed by silver staining (Hitchcock and Brown, 1983) and further characterized by GLC and GLC-MS analyses (Kahler et al., 1996). A micro phenol/water extraction was done as described below. 2 ml aliquots of cultures at ~0.9 of $OD_{600}$ reading were collected, and the bacterial pellets were resuspended in 0.5 ml of buffer A (50 mM $Na_2HPO_4$, pH 7.0, 5 mM EDTA, 0.05% $NaN_3$). A 0.5 ml aliquot of 90% liquefied phenol was added to the cell suspension and mixed by vortexing. The mixture was incubated at 65° C. for 15 min with vortexing every 5 minutes, and then cooled on ice for another 5 minutes. The aqueous phase and the phenol phase were separated by centrifugation. Both phases were dialyzed (6000-8000 molecular weight cut-off membrane) against 5 changes of water and then lyophilized. An extraction method using a solution of 0.25 M EDTA and 0.25 M of TEA was adapted from Valverde et at (Valverde et al, 1997). Cells from 1.5 ml of overnight cultures were resuspended in 50 µl of EDTA-TEA buffer or EDTA-TEA-5% phenol and incubated at 60° C. for 30 minutes. The crude LOS in the supernatant was collected after centrifugation.

A mini-scale LOS preparation was obtained by Proteinase K treatment of whole cell lysates. Briefly, cells were suspended in water, and the protein concentrations were estimated by Bradford assay (BioRad, Hercules, Calif.). A mixture of 8 µl of whole cell lysate at a concentration of 1 µg/ml, 28 µl of 2% SDS in TE buffer, and 8 µl of proteinase K (25 mg/ml) was incubated at 60° C. overnight. The digestion was quenched by adding 38 µl of loading buffer (IM Tris, 10% glycerol, 2% SDS, 5% β-mercaptoethanol, 0.05% bromphenol blue) (Kahler et al, 1996, supra), and heated at 95° C. for 5 minutes. Aliquots of LOS samples were resolved on a 0.75 mM Tricine SDS minigel (BioRad) (16% separating gel, 10% spacer gel, 4% stacking gel), and the LOS migration patterns were visualized by silver staining (Hitchcock and Brown, 1983).

Alternatively, LOS from a genetically-defined mutants of the serogroup B *N. meningitidis* strain NMB (encapsulated, L2 immunotype) (listed in Table I) were initially extracted by the phenol-water method (21). Residual membrane phospholipids (unsaturated fatty acyl residues C18:0) were removed by repeated extraction of the dry LOS samples with 9:1 ethanol:water. The expected LOS fatty acyl components of 3-OHC12:0, 3-OHC14:0 and C12:0 and the absence of membrane phospholipids was assessed by Mass spectroscopy (GC-MS). LOS preparations were examined by SDS-PAGE (22), quantitated and standardized based on the number of lipid A molecules per sample (23). Briefly, the amount of b-hydroxymyristic acid in each LOS preparation was released by methanolysis in methanolic 1M HCl at 80° C. for 4 hr and trimethylsilylated. The resulting methyl b-trimethylsilylmyristate was identified and quantified by GC-MS analysis. All LOS stock solutions were made up in pyrogen free water at 10 nmole/ml concentration, further diluted with PBS to 100 pmole/ml and used at final concentration of 0.56 pmole/ml, which is equivalent approximately to 1 ng/ml of lipid A. *N. meningitidis* lipid A molecular weight (1740 daltons).

Example 10

Structural Analysis of LOS of the Mutant Strains

Mutant meningococci were grown on BHI plates with kanamycin selection overnight and used to inoculate 600 ml of BHI broth. The culture was grown for 6-7 hours at 37° with shaking, and 100 ml of this culture was subsequently added into 1 liter of fresh BHI broth and the culture continued to grow overnight. Six liters of culture were harvested by centrifugation and the cell pellet dried in a SpeedVac (Savant). The dried cells were processed as described (Kahler et al., 1996). The extraction solvent consisted of 90% phenol-chloroform-petroleum ether (2:5:8).

In order to structurally characterize the LOS, further purification was necessary since the PCP-extracted LOS is co-purified with significant levels of phospholipids. The phospholipids were removed by suspending the LOS in ethanol:water (9:1, v/v), stirring constantly for 30 min at room temperature, and centrifuged at 10000×g in a JA-20 rotor (Beckman) at 4° C. for 15 min. the supernatant was removed and the pellet was extracted repeatedly until no more phospholipid was found in the supernatant. The level of phospholipid was determined by the amount of C16:0, C16:1, C18:1 fatty acids present since these fatty acids are characteristic of the phospholipids. The resulting pellet was suspended in water and freeze-dried.

Compositional analysis was performed by the preparation and combined gas chromatographic/mass spectrometric analysis of trimethyl silyl methyl glycosides with N-acetylation, and of fatty acid methyl esters (York et al., 1985). For the determination of Kdo, lipid A was methanolyzed with methanolic 1 M HCl at 80° C. for 4 h (Edebrink et al., 1994) prior to trimethylsiliylation and GC-MS analysis. Ester linked fatty acids were selectively liberated from a vacuum-dried sample by alkaline transesterification with sodium methoxide (0.25 M, 37° C., 15 h) (Bhat et al., 1994). Combined GC analysis was performed using a 50 meter methyl silicone column (Quadrex Corporation, Woodbridge, Conn.).

Example 11

Mass Spectrometry of LOS

To dephosphorylate lipid A, the sample was treated with cold aqueous 48% hydrogen fluoride (HF) and kept for 487 h at 4° C. The HF was removed by flushing under a stream of air, followed by addition of diethyl ether (600 ml) and drying with a stream of air. This latter diethyl ether/drying step was repeated three times. The resulting residue was suspended in deionized water, dialyzed at 4° C. for 48 h and finally freeze-dried.

Oligosaccharides were analyzed by MALDI-TOF mass spectrometry using a Hewlett Packard LD-TOF system. The oligosaccharides were dissolved in distilled water at a final concentration of 2 µg/µl, and 1 µl was mixed with the DHB (dihydroxy benzoic acid in methanol) matrix for analysis.

Tandem MS/MS analysis was performed using a Q-TOF hybrid mass spectrometer (Q-TOFII; Micromass, U.K.) equipped with an electrospray source (Z-spray) operated in either the positive or negative mode. The samples were dissolved in 1:1 methanol and chloroform and infused into mass spectrometer with a syringe pump (Harvard Apparatus, Cambridge, Mass., USA) at a flow rate of 5 uL/min. A potential of 3 kV (+ or −) was applied to the capillary, and nitrogen was employed as both the drying and nebulization gas. NaI and [Glu]-Fibrinopeptide B were used as calibration standards in the negative and positive modes respectively. In the MS analysis the Q1 is operated in RF-only mode with all ions transmitted into the pusher region of the TOF analyzer and the MS spectrum was recorded from m/z 400-2000 with 1-s integration time. For MS/MS spectra, the transmission window of quadrupole (Q1) was set up to about 3 mass units and the selected precursor ions were allowed to fragment in the hexapole collision cell. The collision energies (40-55 eV) were optimized for maximized product ion yield and argon was used as collision gas. The MS/MS data were integrated over a period of 4-5 minutes for each precursor ion.

Example 12

Immunoblots

The detailed colony immunoblot protocol has been published (Kahler et al., 1996, supra). Briefly, cells grown overnight on agar plates with proper selection were resuspended in GC broth, and diluted to $2 \times 10^8$ cells/ml (OD550=0.4). Aliquots of 50 µl of the cell suspensions at various dilutions were applied to a pre-wetted nitrocellulose membrane (BA-S NC; Schleicher & Schuell, Keene, N.H.) using a BioDot apparatus (BioRad). The membrane was allowed to air dry for one hour and then blocked with 3% BSA in TTBS buffer (10 mM Tris, pH 8.0, 150 mM NaCl, 0.05% polyoxy ethylene-sorbitan monolaurate) (TWEEN 20, trademark of ICI Americas, Inc.) for one hour. Monoclonal antibodies specific for serogroups B (2-2-B), C (4-2-C), W-135 (7-1-W), and Y (5-2-Y) were incubated with the membrane for one hour at 1:500, 1:500, 1:500 and 1:50 dilutions in TTBS buffer, respectively. The blot was then incubated with secondary alkaline phosphatase-conjugated anti-mouse IgM-IgG (1:5000 dilution) for one hour and developed by BCIP/NBT staining.

Protein samples for Western blots were resolved by 12% SDS-PAGE, and transferred to PVDF membranes at 30 V, 4° C. overnight using a mini Trans-Blotapparatus (BioRad). 10% BSA in TTBS was used to block the membrane for 1.5 hour. Anti-flag monoclonal antibody was used at 10 µg/ml in TTBS. Anti-KpsF polyclonal serum (Covance Research Products, Inc.) was used at a 1:500 dilution.

In certain Western blot experiments, meningococcal strains grown overnight on appropriate selection plates were suspended in PBS buffer, and the $OD_{550nm}$ reading was determined. An aliquot of cell suspension adjusted to 0.25 of $OD_{550nm}$ (~1.25×108 cells) was mixed with equal volume of 2×SDS loading buffer and boiled for 5 minutes before loading onto a 1.5 mm thick minigel of 12% SDS-PAGE. After electrophoresis, the proteins were transferred to a PVDF membrane with a tank transfer system (BioRad) at constant voltage (30 V) overnight at 4° C. The membrane was blocked with 10% BSA in TTBS buffer (100 mM Tris, pH 7.5, 0.9% NaCl, 0.1% TWEEN 20, trademark of ICI Americas Inc.) and probed with anti-flag monoclonal antibody (Sigma, at 10 μg/ml). Alkaline phosphatase conjugated anti-mouse immunoglobulins (ICN) was used as the secondary antibody and the blot was developed with BCIP/NBT (5-bromo-4-chloro-3-indolyl phosphate/nitro blue tetrazolium) as substrates.

Example 13

Whole-Cell ELISA

The previously published protocol for whole-cell ELISA (Swartley et al., 1998) with minor modification was employed. A 50 μl aliquot of a 1:3 dilution of cell suspension at $OD_{650}$=0.1 was applied to each well of a polystyrene multiwell plate (NUNC polysorp plate, Nalge Nunc International, Rochester, N.Y.) and dried at 37° C. overnight. Fifty microliter aliquots of antibodies specific for serogroup B (2-2-s) and serogroup A (14-1-A) were used at 1:500 and 1:30,000 dilutions, respectively. All incubations were performed at 37° C.

Example 14

Electron Microscopy

Plate grown bacteria were fixed in a solution of 1.25% glutaraldehyde, 3.84% paraformaldehyde, 2% DMSO. 2 μl of sample was applied to the grid surface and allowed to settle onto the surface for 5 minutes. Negative stain was performed with 1% ammonium phosphotungstic acid for 15 seconds. Fixed bacterial samples were treated with 0.01% tannic acid and then washed with cacodylate buffer before a sixty-minute post stain with 1% osmium tetraoxide. After dehydrating samples through a graded ethanol wash series, the samples were embedded in epoxy resin (Epon, Resolution Performance Products, Houston, Tex.) for thin section EM study. The samples were analyzed with a Philips CM-10 Transmission Electron Microscope.

Example 15

Determination of Ketopentoses

The procedure of Dische and Borenfreund (Dische and Borenfreund, 1951, as modified by Bigham (Bigham, 1984) was used to determine the presence of ketopentoses. Briefly, enzyme was incubated at 37° C. for 10 min in the presence of various aldopentoses (ribose 5-phosphate, erythrose 4-phosphate, glucose 6-phosphate, and arabinose) and 100 mM Tris-HCl (pH 7.5) buffer and assayed as follows. A 250 μl aliquot of the reaction solution was quenched with the addition of 50 μl of a 1.5% cysteine solution followed immediately by 1.5 ml of concentrated $H_2SO_4$. A 50 μl aliquot of 0.12% carbazole in 95% ethanol was then added, and the solution was heated at 37° C. for 30 min. The absorbance was read at 540 nm. As reported by Bigham et al. (1984), the conversion of 1 μmol of A5P to 1 μmol of Ru5P gave an ΔA of 8.2.

Example 16

$^{31}$P NMR Analysis

To a solution of phosphorylated pentose (2.7 mM ASP or 5.4 mM Ru5P), 100 mM 1,3-bis[tris(hydroxymethyl)methylamino]propane-HCl (pH 7.5), and 10% $D_2O$ (for NMR lock) in a 3 mm NMR tube was added ~25 pmol of ASP isomerase. This solution, held at 25° C., was then monitored by $^{31}$P NMR until equilibrium (no further change in peak ratio) was achieved. Samples are referenced to an external standard of neat phosphoric acid (0 ppm). Spectra were obtained on a Brucker Avance DRX-500 operating at 202.46 MHz for $^{31}$P with WALTZ16 proton decoupling. Each spectrum represents 64 scans.

Example 17

Statistical Analysis

Student's t test with a two-tailed hypothesis was used to determine the significant difference (P £0.05) between two variables in this study.

TABLE 1

Composition analysis of material extracted from the NMB206 mutant

| Constituents | LOS | HF-treated LOS |
|---|---|---|
| Glc | ± | |
| GlcNAc | − | + |
| C12:0 | + | + |
| C14:0 | + | + |
| 3-OH C12:0 | + | + |
| 3-OH C14:0 | + | + |
| C16:0[a] | + | + |
| C16:1[a] | ± | ± |
| C18:0[a] | + | + |
| C18:1[a] | + | + |

+: Significant amount.
−: None detected.
±: Slight amount.
[a]phospholipid contamination.

TABLE 2

Bacterial strains and plasmids used in this study

| Strains/plasmids | Description or sequence | Reference/Source |
|---|---|---|
| *N. meningitidis* | | |
| NMB | B:2B:P1.2,5:L2 (CDC8201085) | (Stephens et al., 1991) |
| F8229 | Serogroup A strain (CDC1750) | (Swartley et al., 1998) |
| Fam18 | C::2a | (McAllister and Stephens, 1993) |

TABLE 2-continued

Bacterial strains and plasmids used in this study

| Strains/plasmids | Description or sequence | Reference/Source |
|---|---|---|
| GA0929 | Serogroup Y strain | (Swartley et al., 1997) |
| GA1002 | Serogroup W-135 strain | (Swartley et al., 1997) |
| NMB206 | NMB with chromosomal kpsF::aphA-3 mutation | This study |
| NMB240 | NMB carrying pYT240 | This study |
| NMB250 | NMB carrying pYT250 | This study |
| NMB240/206 | 206 carrying pYT240 | This study |
| NMB250/206 | 206 carrying pYT250 | This study |
| NMB249 | NMB with chromosomal kdtA::aphA-3 mutation | This study |
| NMB259 | NMB with chromosomal kdsB::aphA-3 mutation | This study |
| NMB 271 | NMB carrying pYT271 | This study |
| NMB 274 | NMB carrying pYT274 | This study |
| NMB 249/271 | 249 carrying pYT271 | This study |
| NMB 249/274 | 249 carrying pYT274 | This study |
| CAS5 | NMB with chromosomal tal::aphA-3 mutation | This study |
| Plasmids | | |
| pCR2.1 | TA cloning | Stratagene |
| pUC18 | Cloning vector, Amp$^r$ | (Yanisch-Perron et al., 1985) |
| pUC18k | Source of aphA-3(Km$^r$) cassette | (Menard et al., 1993) |
| pFlag-CTC | cloning vector for Flag fusion | Sigma Chemical Co. |
| pCAS5 | EcoRI-BamHI-blunted aphA-3 cassette inserted into the ClaI site of tal insert cloned into pCR2.1 | This study |
| pCAS11 | P$_{tac}$::kpsF/ErmC fragment cloned into HincII site of pYT109 | This study |
| pYT109 | A 1 kb fragment of 120A1 locus with a unique HincII site cloned into pCR2.1 | This study |
| pYT203 | YT60-YT61 PCR product cloned into pCR2.1 | This study |
| pYT205 | Ω (SmaI) inserted into blunted AscI site of pYT203 | This study |
| pYT206 | aphA-3 (SmaI) cloned into blunted AscI site of pYT203 | This study |
| pYT225 | Full length of kpsF coding sequence obtained from YT70 (NdeI) and YT71(XhoI) PCR amplification cloned into NdeI-XhoI digested pET20b | This study |
| pYT239 | YT77(EcoRI) and YT78(BglII) PCR product of K1 kpsF cloned into pFlag-CTC | This study |
| pYT240 | pYT250 with K1 KpsF-Flag fusion under the control of tac promoter | This study |
| pYT243 | 1.47 kb of YT81-YT82 PCR product containing kdtA coding sequence cloned into pCR2.1 | This study |
| pYT250 | Meningococcal shuttle vector (Em$^r$) | This study |
| pYT249 | 754 bp BssHII internal fragment of a 1476 bp amplicon of kdtA, pYT243, replaced by in-frame fusion of aphA-3 (SmaI) cassette | This study |
| pYT256 | PCR product of YT84-YT85 (kdsB) cloned into the HincII-SmaI digested pUC18 | This study |
| pYT259 | SacI-HincII digested and Klenow blunted aphA-3 cassette inserted into EcoRV site within kdsB of pYT256 | This study |
| pYT268 | HindIII-BglII digested YT91-YT92 PCR product amplified from N. meningitidis cloned into HindIII-BglII site of pCTC-Flag | This study |
| pYT269 | HindIII-BglII digested YT91-YT92 PCR product amplified from E. coli cloned into HindIII-BglII site of pCTC-Flag | This study |
| pYT271 | BdglII fragment of pYT268 cloned into EcoRV of pYT250 | This study |
| pYT274 | YT80-YT83 amplified product from pYT269 cloned into EcoRV site of pYT250 | This study |

TABLE 3

| Primers | | SEQ ID NO: |
|---|---|---|
| KANC | 5'-GTGGTATGACATTGCCTTCTGCG3' | 16 |
| YT79 | 5'CATCATAACGGTTCTGGCAAATATTC3' | 17 |
| YT80 | 5'CTGTATCAGGCTGAAAATCTTCTCTC3' | 18 |
| YT81 | 5'CACGATGCCGCTGGCGAAC3' | 19 |

TABLE 3-continued

| Primers | | SEQ ID NO: |
|---|---|---|
| YT82 | 5'GGATACGGCGTTATTTGGACAAAC3' | 20 |
| YT83 | 5'<u>GCCGTCTGAA</u>GTGCTGCAAGGCGATTAAGTTGGG3', meningococcal uptake sequence underlined | 21 |
| YT91 | 5'GGAAATAGAAAG<u>AAGCTT</u>CAATGGCTTTATG3' HindIII site underlined | 22 |
| YT92 | 5'GATTGTA<u>AGATCT</u>TCGCCCCCGATATC3' BglII site underlined | 23 |
| YT93 | 5'CAGCTATTTACT<u>AAGCTT</u>GAATTGCTTTACACC3' HindIII site underlined | 24 |
| YT94 | 5'CATAACA<u>AGATCT</u>ATGCGTTTTCGGTG3', BglII site underlined | 25 |
| YT60 | CGA CTG GGC ACG CGA AGT GTT GC | 2 |
| YT61 | GCA TGA CTT CGT CTA TCG AAA GAC CGG | 3 |
| YT84 | 5'-GACAGGTTGGGAAAAGGCATCAGA-3' | 4 |
| YT85 | 5'-GTTTTCCGGCACGTATCGCATCAC-3' | 5 |
| YT68 | 5'-CAGGGCGTGTGCGGCGTAACTTC-3' | 6 |
| YT69 | 5'-CGTAGAGCGTGTCGGGATAGGCC-3' | 7 |
| YT70 | 5'-GGCGGATG<u>CATATG</u>GCAGAAAACGG-3' | 8 |
| YT71 | 5'-TTTGTTAAT<u>CTCGAG</u>TACAATCCGTGCCG-3' | 9 |
| CAS1 | 5'-TTACAGCA<u>AAGCTT</u>GATGGCAATGGC-3' HindIII site underlined | 10 |
| CAS2 | 5'-TTTGT<u>GGATCC</u>ACTATACAATCCGTG-3' BamHI site underlined | 11 |
| CAS3 | GCG CGC CTG TAA TTC GGG | 37 |
| CAS4 | 5'-CGCCTCTCCCCGCGCGTTGGCCG-3' | 12 |
| YT59 | 5'-CGGCCGACTAGTAGGCCTATTATTTTTG-3' | 26 |
| YT77 | 5'-GTGCAAAGG<u>GAATTC</u>TATGTCTGAAAGAC-3' | 14 |
| YT78 | 5'-CGTTGCT<u>AGATCT</u>GTCGAAAATGCGCAC-3' BglII site underlined | 15 |

TABLE 4

Compositions of the LOS preparation from NMB249 based on MALDI-TOF MS analysis

| Observed Ion | Calculated Ion | Proposed Composition |
|---|---|---|
| 1836 | 1836.3 | $P_2PEA_1G1cN_2C12:0_2\beta OHC12:0_2\beta OHC14:0_2$ |
| 1756 | 1756.3 | $P_1PEA_1G1cN_2C12:0_2\beta OHC12:0_2\beta OHC14:0_2$ |
| 1713 | 1713.2 | $P_2GlcN_2Cl2:0_2\beta OHC12:0_2\beta OHC14:0_2$ |
| 1633 | 1633.3 | $P_1GlcN_2C12:0_2\beta OHC12:0_2\beta OHC14:0_2$ |
| 1558 | 1558.0 | $P_1PEA_1GlcN_2C12:0_1\beta OHC12:0_2\beta OHC14:0_2$ |
| 1451 | 1451.0 | $P_1GlcN_2C12:0_1\beta OHC12:0_1\beta OHC14:0_2$ |
| 1435 | 1435.0 | $P_1GlcN_2C12:0_2\beta OHC12:0_1\beta OHC14:0_2$ |

P = phosphate;
PEA = phosphoethanolamine;
GlcN = glucosamine;
C12:0 = lauric acid;
βOHC12:0 = β-hydroxylauric acid;
βOHC14:0 = β-hydroxymyristic acid

TABLE 5

Coding sequence for kdtA of *Neisseria meningitidis* NMB0014 (SEQ ID NO: 27)

ATGTTCCAATGGCTTTATGATGTATTGTGGCTGCTTGCGCCGATATGGATACGGCGTTAT

TTGGACAAACGCTCCGGAAGTGCCCCGGCATATCGGGCGCATCGGGACGAGCGTTTCGGC

AAGCCGTATCCGAATCCCGTTACCGGCGCGGTTTGGATACACGCCGTTTCGGTCGGAGAA

ACGCGTGCCGCCCAGTCCTTGATACGCGAGTTGCGGCGGCGTTTTCCCGATGCGCCGCTG

CTGATGACGCAGATGACCCCGACGGGGCGGGAAACCGCGCAAGTTCTGTTTCCCGATGCG

CAATGCCGCTATCTTCCGTATGACAAAAAAACGTGGGTACGGCAGTTTTTGCGCGAACAC

CGCCCGATGTTCGGCATTTTGATGGAAACCGAAATCTGGCCCAACCTGATGAGGGAATGC

CGGCGCGCGGGTGTGCCGCTGTTTTTGGCGAATGCGCGGCTGTCGGAAAAATCGTTGAAC

GGTTATCTGAAAGTCCGCCGCCTGATCCGTCCTGCCGCCGCTTCGCTGACGGGGTGTCTG

GCGCAGACAGAGGCGGATGCGGCGCGGTTGGCGAAATTGGGCGCGGCATCCGTGCAGGTG

TGCGGCAATACCAAATACGACATCATACCGTCGGAACAGATGAAAACGCTGGCGGGGCAG

TTTGAAAAACGCATCGGAGGCCGGCCGGTTGCCGTGTGCGGCAGCACGCGCGTTTATCGG

GGTGAAGACGAGGCGGAAAAACTGCTGGCGGCGTGGCAACAATATCGCGGCGATGCGCTG

TABLE 5-continued

| Coding sequence for kdtA of *Neisseria meningitidis* NMB0014 (SEQ ID NO: 27) |
|---|
| CTGGTCGTCGTGCCGCGCCATCCCGAGCATTTTCAGACGGTATTTGAAACGGCAAAACGC |
| TTCGGGTTTAAGGTTCAGCGGCGCAGCGACGGTTTGCCGGTCGAACCTGATACGCAGGTG |
| TGGATAGGCGACAGTATGGGCGAGCTGTATGCGTATTACCTGTGCGCCGATGTCGCTTTT |
| GTCGGCGGCAGTCTGGTCGATTCGGGTTGTCAGAACATCATCGAACCGCTTTCCTGCGGC |
| GTTCCGACGATATTCGGCTTTTCAACCTACAATTTTTCCGAAGCCTGCCGACACGCCTTG |
| GCATCGGGTGCGGCGGTTCAAGTCGAATCGGCGGATGCGTGGCGGGAAGCCGTTGAAAAA |
| ACCTTATCGTCCGAGGGGGGGGGGATGCAGATGCAGGCGCGCGTGGACGGCTTTATCGCA |
| CAACATCGCGGAGCGGGCGCGAGAATCGCCGAGGCGGTGCGGGAAGCGGTATGCGGATAT |
| CGGGGGCGA |

TABLE 6

| Amino Acid Sequence of kdtA gene product of *Neisseria meningitidis* NMB0014 (SEQ ID NO: 28) |
|---|
| MFQWLYDVLWLLAPIWIRRYLDKRSGSAPAYRAHRDERFGKPYPNPVTGAVWIHAVSVGE |
| TRAAQSLIRELRRRFPDAPLLMTQMTPTGRETAQVLFPDAQCRYLPYDKKTWVRQFLREH |
| RPMFGILMETEIWPNLMRECRRAGVPLFLANARLSEKSLNGYLKVRRLIRPAAASLTGCL |
| AQTEADAARLAKLGAASVQVCGNTKYDIIPSEQMKTLAGQFEKRIGGRPVAVCGSTRVYR |
| GEDEAEKLLAAWQQYRGDALLVVVPRHPEHFQTVFETAKRFGFKVQRRSDGLPVEPDTQV |
| WIGDSMGELYAYYLCADVAFVGGSLVDSGCQNIIEPLSCGVPTIFGFSTYNFSEACRHAL |
| ASGAAVQVESADAWREAVEKTLSSEGGGMQMQARVDGFIAQHRGAGARIAEAVREAVCGY |
| RGR |

TABLE 7

| Coding Sequence for kdsB of *Neisseria meningitidis* NMB0014 (SEQ ID NO: 29) |
|---|
| ATGACCGAATTCGTCGTATTGATTCCGGCGCGGCTGGATTCGTCGCGCCTGCCCGGAAAA |
| GCCTTGGCGGACATCCACGGCAAACCGATGGTCGTGCGCGTTGCCGAACAGGCGGCAAAA |
| AGTAAAGCCGCGCGCGTCGTCGTTGCCACCGACCATCCCGATATTCAGACGGCCTGTCAG |
| GCGCACGGTATCGAAGTCGTCATGACTTCAAACCGGCACGAAAGCGGCACGACGCGCCTT |
| GCCGAAGCCTCTGTCGCGCTGAAGCTGCCGCCGCATTTGATTGTTGTGAACGTACAGGGT |
| GACGAGCCGCTGATTGCCCCCGAACTCATCGACCGCACCGCCGAAGTACTCGTCGAAAAC |
| AACGTCCAAATGGCGACCGCCGCCCACGAATTGCACGATTTCGACGAATTGATGAATCCC |
| AACGCCGTCAAAGTCGTCCTCGACAAAAACCGCAACGCCATCTACTTCAGCCGCGCCCCG |
| ATTCCCTATCCGCGTGATGCGATACGTGCCGGAAAAACGCGAAATGCCGTCTGAAACCGCC |
| GTCCTGCGACATATCGGCATCTACGCTTACCGCGCCGGCTTCCTGCAACGCTATGCCGAA |
| ATGAGCGTTTCGCCGCTGGAAACCATCGAATCGCTGGAACAGCTGCGCGTCCTGTGGCAC |
| GGTTATCCCATTGCCGTCGAAACCGCCAAAGAAGCCCCCGCCGCCGGTGTGGATACGCAA |
| GAGGACTTGGACAGGGTTCGCGCCGTATTTCAGACCGTA |

TABLE 8

Amino Acid Sequence of kdsB gene product of
*Neisseria meningitidis* NMB0675 (SEQ ID NO: 30)

MTEFVVLIPARLDSSRLPGKALADIHGKPMVVRVAEQAAKSKAARVVVATDHPDIQTACQ

AHGIEVVMTSNRHESGTTRLAEASVALKLPPHLIVVNVQGDEPLIAPELIDRTAEVLVEN

NVQMATAAHELHDFDELMNPNAVKVVLDKNRNAIYFSRAPIPYPRDAIRAGKREMPSETA

VLRHIGIYAYRAGFLQRYAEMSVSPLETIESLEQLRVLWHGYPIAVETAKEAPAAGVDTQ

EDLDRVRAVFQTV

TABLE 9

Coding Sequence for kpsF of *Neisseria meningitidis* NMB0352
(SEQ ID No: 31)

ATGGCAGAAAACGGAAAATATCTCGACTGGGCACGCGAAGTGTTGCACGCCGAAGCGGAA

GGCTTGCGCGAAATTGCAGCGGAATTGGACAAAAACTTCGTCCTTGCGGCAGACGCGTTG

TTGCACTGCAAGGGCAGGGTCGTTATCACGGGCATGGGCAAGTCGGGACATATCGGGCGC

AAAATGGCGGCAACTATGGCCTCGACCGGCACGCCTGCGTTTTTCGTCCACCCTGCGGAA

GCGGCACACGGCGATTTGGGTATGATTGTGGACAACGACGTGGTCGTCGCGATTTCCAAT

TCCGGCGAAAGCGACGAAATCGCCGCCATCATCCCCGCACTCAAACGCAAAGACATCACG

CTTGTCTGCATCACCGCCCGCCCCGATTCAACCATGGCGCGCCATGCCGACATCCACATC

ACGGCGTCGGTTTCCAAAGAAGCCTGCCCGCTGGGGCTTGCCCCGACCACCAGCACCACC

GCCGTCATGGCTTTGGGCGATGCGTTGGCGGTCGTCCTGCTGCGCGCACGCGCGTTCACG

CCCGACGATTTCGCCTTGAGCCATCCTGCCGGCAGCCTCGGCAAACGCCTACTTTTGCGC

GTTGCCGACATTATGCACAAAGGCGGCGGCCTGCCTGCCGTCCGACTCGGCACGCCCTTG

AAAGAAGCCATCGTCAGCATGAGTGAAAAAGGGCTGGGCATGTTGGCGGTAACGGACGGG

CAAGGCCGTCTGAAAGGCGTATTCACCGACGGCGATTTGCGCCGCCTGTTTCAAGAATGC

GACAATTTTACCGGTCTTTCGATAGACGAAGTCATGCATACGCATCCTAAAACCATCTCC

GCCGAACGTCTCGCCACCGAAGCCCTGAAAGTCATGCAGGCAAACCATGTGAACGGGCTT

CTGGTTACCGATGCAGATGGCGTGCTGATCGGCGCGCTGAATATGCACGACCTGCTGGCG

GCACGGATTGTA

TABLE 10

Coding Sequence of kpsF of *Neisseria meningitidis* NMB0352
(SEQ ID NO: 32)

MAENGKYLDWAREVLHAEAEGLREIAAELDKNFVLAADALLHCKGRVVITGMGKSGHIGR

KMAATMASTGTPAFFVHPAEAAHGDLGMIVDNDVVVAISNSGESDEIAAIIPALKRKDIT

LVCITARPDSTMARHADIHITASVSKEACPLGLAPTTSTTAVMALGDALAVVLLRARAFT

PDDFALSHPAGSLGKRLLLRVADIMHKGGGLPAVRLGTPLKEAIVSMSEKGLGMLAVTDG

QGRLKGVFTDGDLRRLFQECDNFTGLSIDEVMHTHPKTISAERLATEALKVMQANHVNGL

LVTDADGVLIGALNMHDLLAARIV

BIBLIOGRAPHY

Achtman, M. (1994) Clonal spread of serogroup A meningococci: a paradigm for the analysis of microevolution in bacteria. *Mol. Microbiol.* 11: 15-22.

Bateman, A. (1999) The SIS domain: a phosphosugar-binding domain. *Trends Biochem. Sci.* 3:94-95.

Belunis, C. J. and Raetz, C. R. (1992) Biosynthesis of endotoxins. Purification and catalytic properties of 3-deoxy-D-manno-octulosonic acid transferase from *Escherichia coli*. *J. Biol. Chem.* 267: 9988-9997.

Bigham, E. C., Gragg, C. E., Hall, W. R., Kelsey, J. E., Mallory, W. R., Richardson, D. C., Benedict, C. and Ray, P. H. (1984) Inhibition of arabinose 5-phosphate isomerase. An approach to the inhibition of bacterial lipopolysaccharide biosynthesis. *J. Med. Chem.* 27:717-26.

Brabetz, W., Schirmer, C. E., and Brade, H. (2000) 3-Deoxy-D-manno-oct-2-ulosonic acid (kdo) transferase of *Legionella pneumophila* transfers two kdo residues to a structurally different lipid A precursor of *Escherichia coli*. *J. Bacteriol.* 182: 4654-4657.

Brandtzaeg, P. P. Kierulf, P. Gaustad, A. Skulberg, J. N. Bruun, S. Halvorsen, Brandtzaeg and E. Sorensen (1989) Plasma endotoxin as a predictor of multiple organ failure and death in systemic meningococcal disease. *J. Infect. Dis.* 159:195

Brandtzaeg, P., R. Ovsteboo, and P. Kierulf (1992) Compartmentalization of lipopolysaccharide production correlates with clinical presentation in meningococcal disease. *J. Infect. Dis.* 166:650.

Brandtzaeg, P., R. Ovstebo, and P. Kierulf. (1995) Bacteremia and compartmentalization of LPS in meningococcal disease. *Progress in Clinical and Biological Research* 392: 219

Brozek, K. A., and Raetz, C. R. (1990) Biosynthesis of lipid A in *Escherichia coli*. Acyl carrier protein-dependent incorporation of laurate and myristate. *J. Biol. Chem.* 265: 15410-15417.

Christodoulides, M., Everson, J. S., Liu, B. L., Lambden, P. R., Watt, P. J., Thomas, E. J. and Heckels, J. E. (2000) Interaction of primary human endometrial cells with *Neisseria gonorrhoeae* expressing green fluorescent protein. *Mol. Microbiol.* 5:32-43.

Cieslewicz, M. and Vimr, E. (1996) Thermoregulation of kpsF, the first region 1 gene in the kps locus for polysialic acid biosynthesis in *Escherichia coli* K1. *J. Bacteriol.* 178: 3212-20.

Cieslewicz, M. and Vimr, E. (1997) Reduced polysialic acid capsule expression in *Escherichia coli* K1 mutants with chromosomal defects in kpsF. *Mol. Microbiol.* 26:237-49.

da Silva Correia, J., K. Soldau, U. Christen, P. S. Tobias, and R. J. Ulevitch. (2001) Lipopolysaccharide is in Close Proximity to Each of the Proteins in Its Membrane Receptor Complex: Transfer from CD14 to TLR4 and MD-2. *J. Biol. Chem.* 26:26.

Dische, X. and Borenfreund, E. (1951) a new spectrophotometric method for the detection and determination of keto sugars and trioses. *J. Biol. Chem.* 192:583-587.

Edebrink, P., Jansson, P. E., Rahman, M. M., Widmalm, G., Holme, T., Rahman, M. and Weintraub, A. (1994) Structural studies of the 0-polysaccharide from the lipopolysaccharide of *Moraxella* (*Branhamella*) *catarrhalis* serotype A (strain ATCC 25238). *Carbohydr. Res.* 257:269-284.

Estabrook, M. M., Griffiss, J. M. and Jarvis, G. A. (J 997) Sialylation of *Neisseria meningitidis* lipooligosaccharide inhibits serum bactericidal activity by masking lacto-N-neotetraose. *Infect. Immun.* 65:4436-44.

Finke, A, Bronner, D., Nikolaev, A. V., Jann, B. and Jann, K. (1991) Biosynthesis of the *Escherichia coli* K5 polysaccharide, a representative of group II capsular polysaccharides: polymerization in vitro and characterization of the product. *J. Bacteriol.* 173:4088-94.

Frecer, V., B. Ho, and J. L. Ding. (2000b) Interpretation of biological activity data of bacterial endotoxins by simple molecular models of mechanism of action. *Eur. J. Biochem.* 267:837.

Frecer, V., B. Ho, and J. L. Ding. (2000b) Molecular dynamics study on lipid A from *Escherichia coli*: insights into its mechanism of biological action. *Biochim. Biophys. Acta* 1466:87.

Fussenegger, M., Kahrs, A. F., Facius, D. and Meyer, T. F. (1996) Tetrapac (tpc), a novel genotype of *Neisseria gonorrhoeae* affecting epithelial cell invasion, natural transformation competence and cell separation. *Mol. Microbiol.* 19:1357-72.

Galanos, C., V. Lehmann, O. Luderitz, E. T. Rietschel, O. Westphal, H. Brade, L. Brade, M. A. Freudenberg, T. Hansen-Hagge, T. Luderitz, and et al. 1984. Endotoxic properties of chemically synthesized lipid A part structures. Comparison of synthetic lipid A precursor and synthetic analogues with biosynthetic lipid A precursor and free lipid A. *Eur. J. Biochem.* 140:221.

Gangloff, S. C., N. Hijiya, A. Haziot, and S. M. Goyert. 1999. Lipopolysaccharide structure influences the macrophage response via CD 14-independent and CD 14-dependent pathways. *Clinical Infectious Diseases* 28:491.

Goldman, R. C., Doran, C. C., Kadam, S. K., and Capobianco, J. O.). (1988) Lipid A precursor from *Pseudomonas aeruginosa* is completely acylated prior to addition of 3-deoxy-D-manno-octulosonate. *J. Biol. Chem.* 263:5217-5223.

Gotschlich, E. C., Fraser. B. A., Nishimura, O., Robbins, J. B. and Liu, T. Y. (1981) Lipid on capsular polysaccharides of gram-negative bacteria. *J. Biol. Chem.* 256: 8915-21.

Hawkins, L. D., S. T. Ishizaka, P. McGuinness, H. Zhang, W. Gavin, B. DeCosta, Z. Meng, H. Yang, M. Mullarkey, D. W. Young, D. P. Rossignol, A. Nault, J. Rose, M. Przetak, J. C. Chow, and F. Gusovsky. 2002. A novel class of endotoxin receptor agonists with simplified structure, toll-like receptor 4-dependent immunostimulatory action, and adjuvant activity. *J Pharmacol. Exp. Ther.* 300:655.

Hirschfeld, M., J. J. Weis, V. Toshchakov, C. A. Salkowski, M. J. Cody, D. C. Ward, N. Qureshi, S. M. Michalek, and S. N. Vogel. 2001. Signaling by Toll-Like Receptor 2 and 4 Agonists Results in Differential Gene Expression in Murine Macrophages. *Infect. Immun.* 69:1477.

Hitchcock, P. J. and Brown, T. M. (1983) Morphological heterogeneity among *Salmonella* lipopolysaccharide chemotypes in silver-stained polyacrylamide gels. *J. Bacteriol.* 154:269.

Janik, A., Juni, E. and Heym, G. A. (1976) Genetic transformation as a tool for detection of *Neisseria gonorrhoeae*. *J. Clin. Microbiol.* 4:71-81.

Jarvis, G. A. (1995) Recognition and control of neisserial infection by antibody and complement. *Trends Microbiol.* 3:198-201.

Kahler, C. M., Carlson, R. W., Rahman, M. M., Martin, L. E. and Stephens, D. S. (1996) Inner core biosynthesis of lipooligosaccharide (LOS) in *Neisseria meningitidis* serogroup B: identification and role in LOS assembly of the alpha1,2 N-acetylglucosamine transferase (RfaK). *J. Bacteriol.* 178:1265-1273.

Kahler, C. M., Martin, L. E., Shih, G. C., Rahman, M. M., Carlson, R. W. and Stephens, D. S. (1998) The α2→8)- linked polysialic acid capsule and lipooligosaccharide structure both contribute to the ability of serogroup B *Neisseria meningitidis* to resist the bactericidal activity of normal human serum. *Infect. Immun.* 66:5939-5947.

Kahler, C. M. and Stephens, D. S. (1998) Genetic basis for biosynthesis, structure, and function of meningococcal lipooligosaccharide (endotoxin). *Crit. Rev. Microbiol.* 24, 281-334.

Lien, E., T. K. Means, H. Heine, A. Yoshimura, S. Kusumoto, K. Fukase, M. J. Fenton, M. Oikawa, N. Qureshi, B. Monks, R. W. Finberg, R. R. Ingalls, and D. T. Golenbock. 2000. Toll-like receptor 4 imparts ligand-specific recognition of bacterial lipopolysaccharide. *J. Clin. Invest.* 105:497.

Loppnow, H., H. Brade, I. Durrbaum, C. A. Dinarello, S. Kusumoto, E. T. Rietschel, and H. D. Flad. 1989. IL-1 induction-capacity of defined lipopolysaccharide partial structures. *J Immunol* 142:3229.

Luderitz, O., K. Tanamoto, C. Galanos, G. R. McKenzie, H. Brade, U. Zahringer, E. T. Rietschel, S. Kusumoto, and T. Shiba. 1984. Lipopolysaccharides: structural principles and biologic activities. *Rev Infect Dis* 6:428.

Matsuyama, N., T. Kirikae, F. Kirikae, M. Hashimoto, K. Amanot, S. Hayashi, Y. Hirai, T. Kubota, and M. Nakano. 2001. Non-standard biological activities of lipopolysaccharide from Helicobacter pylori. *J Med Microbiol* 50:865.

McAllister, C. F. and Stephens, D. S. (1993) Analysis in *Neisseria meningitidis* and other *Neisseria* species of genes homologous to the FKBP immunophilin family. *Mol. Microbiol.* 10:13-23.

Menard, R., Sansonetti, P. J. and Parsot, C. (1993) Nonpolar mutagenesis of the ipa genes defines IpaB, IpaC, and IpaD as effectors of *Shigella flexneri* entry into epithelial cells. *J. Bacteriol.* 175:5899-906.

Moe, G. R., Tan, S. and Granoff, D. M. (1999) Differences in surface expression of NspA among *Neisseria meningitidis* group B strains. *Infect. Immun.* 67:5664-75.

Mohan, S., and Raetz, C. R. (1994) Endotoxin biosynthesis in *Pseudomonas aeruginosa*: enzymatic incorporation of laurate before 3-deoxy-D-manno-octulosonate. *J. Bacteriol.* 176:6944-6951.

Moran, A. P., Prendergast, M. M. and Appelmelk, B. J. (1996) Molecular mimicry of host structures by bacterial lipopolysaccharides and its contribution to disease. *FEMS Immunol. Med. Microbiol.* 16:105-115.

Nath, K. (1990) A rapid DNA isolation procedure from petri dish grown clinical bacterial isolates. *Nucleic Acids Res.* 18:6462.

Nurminen, M., E. T. Rietschel, and H. Brade. 1985. Chemical characterization of Chlamydia trachomatis lipopolysaccharide. *Infect. Immun.* 48:573.

Odegaard, T. J., Kaltashov, I. A., Cotter, R. J., Steeghs, L., van der Ley, P., Khan, S., Maskell, D. J., and Raetz, C. R. (1997) Shortened hydroxyacyl chains on lipid A of *Escherichia coli* cells expressing a foreign UDP-N-acetylglucosamine O-acyltransferase. *J. Biol. Chem.* 272:19688-19696.

Ogawa, T., Y. Asai, M. Hashimoto, O. Takeuchi, T. Kurita, Y. Yoshikai, K. Miyake, and S. Akira. 2002. Cell activation by Porphyromonas gingivalis lipid A molecule through Toll-like receptor 4- and myeloid differentiation factor 88-dependent signaling pathway. *Int. Immunol.* 14:1325.

Pazzani, C., Rosenow, C., Boulnois, G. J., Bronner, D., Jann, K. and Roberts, I. S. (1993) Molecular analysis of region 1 of the *Escherichia coli* K5 antigen gene cluster: a region encoding proteins involved in cell surface expression of capsular polysaccharide. *J. Bacteriol.* 175:5978-5983.

Plotz, B. M., B. Lindner, K. O. Stetter, and O. Holst. 2000. Characterization of a novel lipid A containing D-galacturonic acid that replaces phosphate residues. The structure of the lipid a of the lipopolysaccharide from the hyperthermophilic bacterium Aquifex pyrophilus. *J. Biol. Chem.* 275:11222.

Prentki, P. and Krisch, H. M. (1984) In vitro insertional mutagenesis with a selectable DNA fragment. *Gene* 29:303-13.

Raetz, C. R. H. (1996) Bacterial lipopolysaccharides: a remarkable family of bioactive macroamphiphiles. In Neidhardt, F. C. (ed.) *Escherichia coli and Salmonella: Cellular and Molecular Biology*. American Society for Microbiology, Washington, D.C., Vol. 1, pp. 1035-1063.

Rahman, M. M., Stephens, D. S., Kahler, C. M., Glushka, J. and Carlson, R. W. (1998) The lipooligosaccharide (LOS) of *Neisseria meningitidis* serogroup B strain NMB contains L2, L3, and novel oligosaccharides, and lacks the lipid-A 4'-phosphate substituent. *Carbohydr. Res.* 307:311-324.

Rietschel, E. T., T. Kirikae, F. U. Schade, U. Mamat, G. Schmidt, H. Loppnow, A. J. Ulmer, U. Zahringer, U. Seydel, F. Di Padova, and et al. (1994) Bacterial endotoxin: molecular relationships of structure to activity and function. *Faseb J.* 8:217

Rosenow, C., Roberts, I. S. and Jann, K. (1995) Isolation from recombinant *Escherichia coli* and characterization of CMP-Kdo synthetase, involved in the expression of the capsular K5 polysaccharide (K-CKS). *FEMS Microbiol. Leas.* 125:159-64.

Roth, R. I., R. Yamasaki, R. E. Mandrell, and J. M. Griffiss. (1992) Ability of gonococcal and meningococcal lipooligosaccharides to clot Limulus amebocyte lysate. *Infect. Immun.* 60:762.

Rund, S., B. Lindner, H. Brade, and O. Holst. 1999. Structural analysis of the lipopolysaccharide from *Chlamydia trachomatis* serotype L2. *J. Biol. Chem.* 274:16819.

Ryll, R. R., Rudel, T., Scheuerpflug, I., Barten, R. and Meyer, T. F. (1997) PilC of *Neisseria meningitidis* is involved in class II pilus formation and restores pilus assembly, natural transformation competence and adherence to epithelial cells in PilC-deficient gonococci. *Mol. Microbiol.* 23:879-892.

Salimath, P. V., J. Weckesser, W. Strittmatter, and H. Mayer. 1983. Structural studies on the non-toxic lipid A from Rhodopseudomonas sphaeroides ATCC 17023. *Eur. J. Biochem.* 136:195.

Schromm, A. B., K. Brandenburg, H. Loppnow, U. Zahringer, E. T. Rietschel, S. F. Carroll, M. H. Koch, S. Kusumoto, and U. Seydel. (1998) The charge of endotoxin molecules influences their conformation and IL-6-inducing capacity. *J. Immunol.* 161:5464.

Seydel, U., M. Oikawa, K. Fukase, S. Kusumoto, and K. Brandenburg. 2000. Intrinsic conformation of lipid A is responsible for agonistic and antagonistic activity. *Eur. J. Biochem.* 267:3032.

Simpson, D. A., Hammarton, T. C. and Roberts, I. S. (1996) Transcriptional organization and regulation of expression of region 1 of the *Escherichia coli* K5 capsule gene cluster. *J. Bacteriol.* 178:6466-6474.

Steeghs, L., den Harton, R., den Boer, A., Zodmer, B., Roholl, P., and van der Ley, P. (1998) Meningitis bacterium is viable without endotoxin. *Nature* 392:449-450.

Stephens, D. S. and McGee, Z. A. (1981) Attachment of *Neisseria meningitidis* to human mucosal surfaces: influence of pili and type of receptor cell. *J. Infect. Dis.* 143:525-532.

Stephens, D. S., Spellman, P. A. and Swartley, J. S. (1993) Effect of the (α2→8)-linked polysialic acid capsule on adherence of *Neisseria meningitidis* to human mucosal cells. *J. Infect. Dis.* 167:475-479.

Stephens, D. S., Swartley, J. S., Kathariou, S. and Morse, S. A. (1991) Insertion of Tn916 in *Neisseria meningitidis* resulting in loss of group B capsular polysaccharide. *Infect. Immun.* 59:4097-4102.

Suda, Y., Y. M. Kim, T. Ogawa, N. Yasui, Y. Hasegawa, W. Kashihara, T. Shimoyama, K. Aoyama, K. Nagata, T. Tamura, and S. Kusumoto. 2001. Chemical structure and biological activity of a lipid A component from Helicobacter pylori strain 206. *J. Endotoxin Res.* 7:95.

Swartley, J. S., Ahn, J. H., Liu, L. J., Kahler, C. M. and Stephens, D. S. (1996) Expression of sialic acid and polysialic acid in serogroup B *Neisseria meningitidis*: divergent transcription of biosynthesis and transport operons through a common promoter region. *J. Bacteriol.* 178: 4052-4059.

Swartley, J. S., Liu, L. J., Miller, Y. K., Martin, L. E., Edupuganti, S. and Stephens, D. S. (1998) Characterization of the gene cassette required for biosynthesis of the (α1→6)-linked N-acetyl-D-mannosamine-1-phosphate capsule of serogroup A *Neisseria meningitidis*. *J Bacteriol.* 180: 1533-1539.

Swartley, J. S., Marfin, A. A., Edupuganti, S., Liu, L. J., Cieslak, P., Perkins, B., Wenger, J. D. and Stephens, D. S. (1997) Capsule switching of *Neisseria meningitidis*. *Proc. Natl. Acad. Sci. USA* 94:271-276.

Tanamoto, K., and S. Azumi. 2000. *Salmonella*-type heptaacylated lipid A is inactive and acts as an antagonist of lipopolysaccharide action on human line cells. *J. Immunol.* 164:3149.

Tettelin, H., Saunders, N. J., Heidelberg, J., Jeffries, A. C., Nelson, K. E., Eisen, J. A., Ketchum, K. A., Hood, D. W., Peden, J. F., Dodson, R. J., Nelson, W. C., Gwinn, M. L., DeBoy, R., Peterson, J. D., Hickey, E. K., Haft, D. H., Salzberg, S. L., White, O., Fleischmann, R. D., Dougherty, B. A., Mason, T., Ciecko, A., Parksey, D. S., Blair, E., Cittone, H., Clark, E. B., Cotton, M. D., Utterback, T. R., Khouri, H., Qin, H., Vamathevan, J., Gill, J., Scarlato, V., Masignani, V., Pizza, M., Grandi, G., Sun, L., Smith, H. O., Fraser, C. M., Moxon, E. R., Rappuoli, R. and Venter, J. C. (2000) Complete genome sequence of *Neisseria meningitidis* serogroup B strain MC58. *Science* 287:1809-1815.

Troy, F. A., Vijay, I. K. and Tesche, N. (1975) Role of undecaprenyl phosphate in synthesis of polymers containing sialic acid in *Escherichia coli*. *J. Biol. Chem.* 250:156-163.

Troy, F. A. (1992) Polysialylation: from bacteria to brains. *Glycobiology* 2:5-23.

Tzeng, Y.-L. and Stephens, D. S. (2000) Epidemiology and pathogenesis of *Neisseria meningitidis*, *Microbes Infect.* 6:687-700.

Tzeng, Y. L., Swartley, J. S., Miller, Y. K., Nisbet, R. E., Liu, L. J., Ahn, J. H. and Stephens, D. S. (2001) Transcriptional regulation of divergent capsule biosynthesis and transport operon promoters in serogroup B *Neisseria meningitidis*. *Infect. Immun.* 69:2502-11.

Valverde, C., Hozbor, D. F. and Lagares, A. (1997) Rapid preparation of affinity-purified lipopolysaccharide samples for electrophoretic analysis. *BioTechniques* 22: 230-2, 234, 236.

van der Ley, P., L. Steeghs, H. J. Hamstra, J. ten Hove, B. Zomer, and L. van Alphen. (2001) Modification of lipid A biosynthesis in *Neisseria meningitidis* lpxL mutants: influence van on lipopolysaccharide structure, toxicity, and adjuvant activity. *Infect. Immun.* 69:5981 van Deuren, M., P. Brandtzaeg, and J. W. van der Meer (2000) Update on meningococcal disease with emphasis on pathogenesis and clinical management. *Clin. Microbiol. Rev.* 13:344.

Vimr, E. R. and Troy, F. A. (1985) Regulation of sialic acid metabolism in *Escherichia coli*: role of N-acylneuraminate pyruvate-lyase. *J. Bacteriol.* 164, 854-860.

Virji, M., Makepeace, K., Ferguson, D. J., Achtman, M. and Moxon, E. R. (1993) Meningococcal Opa and Opc proteins: their role in colonization and invasion of human epithelial and endothelial cells. *Mol. Microbiol.* 10:499-510.

Wood, T. (ed.) (1985) The pentose phosphate pathway. Academic Press, Orlando, Fla.

Yamada, M., Yamada, Y. and Saier, M. H. (1990) Nucleotide sequence and expression of the gutQ gene within the glucitol operon of *Escherichia coli*. *DNA Seq.* 1: 141-5.

Yanisch-Perron, C., Vieira, J. and Messing, J. (1985) Improved MI 3 phage cloning vectors and host strains: nucleotide sequences of the M13mp18 and pUCI9 vectors. *Gene* 33:103-19.

York, W. S., Darvill, A. G., McNeil, M., Stevenson, T. T. and Albersheim, P. (1985) Isolation and characterization of plant cell walls and cell wall components. *Methods Enzymol.* 118:340.

Yoshizaki, H., N. Fukuda, K. Sato, M. Oikawa, K. Fukase, Y. Suda, and S. Kusumoto. (2001) First Total Synthesis of the Re-Type Lipopolysaccharide. *Angew. Chem. Int. Ed.* 88:1475.

Zahringer, U., Y. A. Knirel, B. Lindner, J. H. Helbig, A. Sonesson, R. Marre, and E. T. Rietschel. 1995. The lipopolysaccharide of *Legionella pneumophila* serogroup 1 (strain Philadelphia 1): chemical structure and biological significance. *Prog. Clin. Biol. Res.* 392:113.

Zhou, D. and Apicella, M. A. (1996) Plasmids with erythromycin resistance and catechol 2,3-dioxygenase- or beta-galactosidase-encoding gene cassettes for use in *Neisseria* spp. *Gene* 171:1334.

Zhou, Z., K. A. White, A. Polissi, C. Georgopoulos, and C. R. Raetz. (1998) Function of *Escherichia coli* MsbA, an essential ABC family transporter, in lipid A and phospholipid biosynthesis. *J. Biol. Chem.* 273:12466.

We claim:

1. A 3-keto-3-deoxyoctanoic acid-free (KDO-free) lipid A preparation from *Neisseria meningitidis* NMB249, deposited with the American Type Culture Collection as PTA-4081.

2. An immunogenic composition comprising the KDO-free lipid A preparation of claim 1 and cells of *Neisseria meningitidis* NMB249, deposited with the American Type Culture Collection as PTA-4081, and a suitable carrier.

3. A pharmaceutically acceptable composition comprising the KDO-free lipid A preparation of claim 1.

4. The pharmaceutically acceptable composition of claim 3 further comprising at least one immunogenic molecule which is heterologous to the KDO-free lipid A composition.

* * * * *

SEQUENCE LISTING

<160> NUMBER OF SEQ ID NOS: 37

<210> SEQ ID NO 1
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

Asp Tyr Lys Asp Asp Asp Asp Lys
  1               5

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 2
cgactgggca cgcgaagtgt tgc                                            23

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 3
gcatgacttc gtctatcgaa agaccgg                                        27

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 4
gacaggttgg gaaaaggcat caga                                           24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 5
gttttccggc acgtatcgca tcac                                           24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 6
cagggcgtgt gcggcgtaac ttc                                            23

<210> SEQ ID NO 7
<211> LENGTH: 23
<212> TYPE: DNA
<213> ORGANISM: Artificial Sequence
```

```
<220> FEATURE:
<223> OTHER INFORMATION: Description of Artificial Sequence:
      Oligonucleotide primer

<400> SEQUENCE: 7
cgtagagcgt gtcgggatag gcc                                              23

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 8
ggcggatgca tatggcagaa aacgg                                            25

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 9
tttgttaatc tcgagtacaa tccgtgccg                                        29

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 10
ttacagcaaa gcttgatggc aatggc                                           26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 11
tttgtggatc cactatacaa tccgtg                                           26

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 12
cgcctctccc cgcgcgttgg ccg                                              23

<210> SEQ ID NO 13
<211> LENGTH: 28
<212> TYPE: DNA
<213> ORGANISM: Artificial Sequence
<220> FEATURE:
```

-continued

<223> OTHER INFORMATION: Description of Artificial Sequence:
      Oligonucleotide primer

<400> SEQUENCE: 13
cggccgacta gtaggcctat tattttg                                28

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 14
gtgcaaaggg aattctatgt ctgaaagac                              29

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 15
cgttgctaga tctgtcgaaa atgcgcac                               28

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 16
gtggtatgac attgccttct gcg                                    23

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 17
catcataacg gttctggcaa atattc                                 26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 18
ctgtatcagg ctgaaaatct tctctc                                 26

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence:

Oligonucleotide primer

<400> SEQUENCE: 19
cacgatgccg ctggcgaac                                                19

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 20
ggatacggcg ttatttggac aaac                                          24

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 21
gccgtctgaa gtgctgcaag gcgattaagt tggg                               34

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 22
ggaaatagaa agaagcttca atggctttat g                                  31

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 23
gattgtaaga tcttcgcccc cgatatc                                       27

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 24
cagctattta ctaagcttga attgctttac acc                                33

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 25
cataacaaga tctatgcgtt ttcggtg 27

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 26
cggccgacta gtaggcctat tatttttg 28

<210> SEQ ID NO 27
<211> LENGTH: 1269
<212> TYPE: DNA
<213> ORGANISM: Neisseria meningitidis

<400> SEQUENCE: 27

| | | |
|---|---|---|
| atgttccaat ggctttatga tgtattgtgg ctgcttgcgc cgatatggat acggcgttat | 60 |
| ttggacaaac gctccggaag tgccccggca tatcgggcgc atcgggacga gcgtttcggc | 120 |
| aagccgtatc cgaatcccgt taccggcgcg gtttggatac acgccgtttc ggtcggagaa | 180 |
| acgcgtgccg cccagtcctt gatacgcgag ttgcggcggc gttttcccga tgcgccgctg | 240 |
| ctgatgacgc agatgacccc gacggggcgg gaaaccgcgc aagttctgtt tcccgatgcg | 300 |
| caatgccgct atcttccgta tgacaaaaaa acgtgggtac ggcagttttt gcgcgaacac | 360 |
| cgcccgatgt tcggcatttt gatggaaacc gaaatctggc ccaacctgat gagggaatgc | 420 |
| cggcgcgcgg gtgtgccgct gttttggcg aatgcgcggc tgtcggaaaa atcgttgaac | 480 |
| ggttatctga agtccgccg cctgatccgt cctgccgccg cttcgctgac ggggtgtctg | 540 |
| gcgcagacag aggcggatgc ggcgcggttg gcgaaattgg gcgcggcatc cgtgcaggtg | 600 |
| tgcggcaata ccaaatacga catcataccg tcggaacaga tgaaaacgct ggcggggcag | 660 |
| tttgaaaaac gcatcggagg ccggccggtt gccgtgtgcg gcagcacgcg cgtttatcgg | 720 |
| ggtgaagacg aggcggaaaa actgctggcg gcgtggcaac aatatcgcgg cgatgcgctg | 780 |
| ctggtcgtcg tgccgcgcca tcccgagcat tttcagacgg tatttgaaac ggcaaaacgc | 840 |
| ttcgggttta aggttcagcg gcgcagcgac ggtttgccgg tcgaacctga tacgcaggtg | 900 |
| tggataggcg acagtatggg cgagctgtat gcgtattacc tgtgcgccga tgtcgctttt | 960 |
| gtcggcggca gtctggtcga ttcgggttgt cagaacatca tcgaaccgct ttcctgcggc | 1020 |
| gttccgacga tattcggctt ttcaacctac aattttccg aagcctgccg acacgccttg | 1080 |
| gcatcgggtg cggcggttca agtcgaatcg gcggatgcgt ggcgggaagc cgttgaaaaa | 1140 |
| accttatcgt ccgaggggg ggggatgcag atgcaggcgc gctggacgg ctttatcgca | 1200 |
| caacatcgcg gagcgggcgc gagaatcgcc gaggcggtgc gggaagcggt atgcggatat | 1260 |
| cgggggcga | 1269 |

<210> SEQ ID NO 28
<211> LENGTH: 423
<212> TYPE: PRT
<213> ORGANISM: Neisseria meningitidis

<400> SEQUENCE: 28

Met Phe Gln Trp Leu Tyr Asp Val Leu Trp Leu Leu Ala Pro Ile Trp

```
  1               5               10              15

Ile Arg Arg Tyr Leu Asp Lys Arg Ser Gly Ser Ala Pro Ala Tyr Arg
              20                      25                  30

Ala His Arg Asp Glu Arg Phe Gly Lys Pro Tyr Pro Asn Pro Val Thr
              35                      40                  45

Gly Ala Val Trp Ile His Ala Val Ser Val Gly Glu Thr Arg Ala Ala
              50                      55                  60

Gln Ser Leu Ile Arg Glu Leu Arg Arg Phe Pro Asp Ala Pro Leu
 65                       70                  75                  80

Leu Met Thr Gln Met Thr Pro Thr Gly Arg Glu Thr Ala Gln Val Leu
                  85                      90                  95

Phe Pro Asp Ala Gln Cys Arg Tyr Leu Pro Tyr Asp Lys Lys Thr Trp
                 100                     105                 110

Val Arg Gln Phe Leu Arg Glu His Arg Pro Met Phe Gly Ile Leu Met
             115                     120                 125

Glu Thr Glu Ile Trp Pro Asn Leu Met Arg Glu Cys Arg Arg Ala Gly
         130                     135                 140

Val Pro Leu Phe Leu Ala Asn Ala Arg Leu Ser Glu Lys Ser Leu Asn
145                 150                     155                 160

Gly Tyr Leu Lys Val Arg Arg Leu Ile Arg Pro Ala Ala Ser Leu
                 165                     170                     175

Thr Gly Cys Leu Ala Gln Thr Glu Ala Asp Ala Ala Arg Leu Ala Lys
                 180                     185                 190

Leu Gly Ala Ala Ser Val Gln Val Cys Gly Asn Thr Lys Tyr Asp Ile
                 195                     200                 205

Ile Pro Ser Glu Gln Met Lys Thr Leu Ala Gly Gln Phe Glu Lys Arg
210                     215                     220

Ile Gly Gly Arg Pro Val Ala Val Cys Gly Ser Thr Arg Val Tyr Arg
225                 230                     235                 240

Gly Glu Asp Glu Ala Glu Lys Leu Leu Ala Ala Trp Gln Gln Tyr Arg
                 245                     250                 255

Gly Asp Ala Leu Leu Val Val Val Pro Arg His Pro Glu His Phe Gln
                 260                     265                 270

Thr Val Phe Glu Thr Ala Lys Arg Phe Gly Phe Lys Val Gln Arg Arg
             275                     280                 285

Ser Asp Gly Leu Pro Val Glu Pro Asp Thr Gln Val Trp Ile Gly Asp
         290                     295                 300

Ser Met Gly Glu Leu Tyr Ala Tyr Tyr Leu Cys Ala Asp Val Ala Phe
305                 310                     315                 320

Val Gly Gly Ser Leu Val Asp Ser Gly Cys Gln Asn Ile Ile Glu Pro
                 325                     330                 335

Leu Ser Cys Gly Val Pro Thr Ile Phe Gly Phe Ser Thr Tyr Asn Phe
                 340                     345                 350

Ser Glu Ala Cys Arg His Ala Leu Ala Ser Gly Ala Ala Val Gln Val
             355                     360                 365

Glu Ser Ala Asp Ala Trp Arg Glu Ala Val Glu Lys Thr Leu Ser Ser
         370                     375                 380

Glu Gly Gly Gly Met Gln Met Gln Ala Arg Val Asp Gly Phe Ile Ala
385                 390                     395                 400

Gln His Arg Gly Ala Gly Ala Arg Ile Ala Glu Ala Val Arg Glu Ala
                 405                     410                 415

Val Cys Gly Tyr Arg Gly Arg
                 420
```

<210> SEQ ID NO 29
<211> LENGTH: 759
<212> TYPE: DNA
<213> ORGANISM: Neisseria meningitidis

<400> SEQUENCE: 29

```
atgaccgaat cgtcgtatt gattccggcg cggctggatt cgtcgcgcct gcccggaaaa      60
gccttggcgg acatccacgg caaaccgatg gtcgtgcgcg ttgccgaaca ggcggcaaaa     120
agtaaagccg cgcgcgtcgt cgttgccacc gaccatcccg atattcagac ggcctgtcag    180
gcgcacggta tcgaagtcgt catgacttca aaccggcacg aaagcggcac gacgcgcctt    240
gccgaagcct ctgtcgcgct gaagctgccg ccgcatttga ttgttgtgaa cgtacagggt    300
gacgagccgc tgattgcccc cgaactcatc gaccgcaccg ccgaagtact cgtcgaaaac    360
aacgtccaaa tggcgaccgc cgcccacgaa ttgcacgatt tcgacgaatt gatgaatccc    420
aacgccgtca agtcgtcct cgacaaaaac cgcaacgcca tctacttcag ccgcgccccg    480
attccctatc cgcgtgatgc cgatacgtgcc ggaaaacgcg aaatgccgtc tgaaaccgcc    540
gtcctgcgac atatcggcat ctacgcttac cgcgccggct tcctgcaacg ctatgccgaa    600
atgagcgttt cgccgctgga aaccatcgaa tcgctggaac agctgcgcgt cctgtggcac    660
ggttatccca ttgccgtcga aaccgccaaa gaagcccccg ccgccggtgt ggatacgcaa    720
gaggacttgg acagggttcg cgccgtattt cagaccgta                           759
```

<210> SEQ ID NO 30
<211> LENGTH: 253
<212> TYPE: PRT
<213> ORGANISM: Neisseria meningitidis

<400> SEQUENCE: 30

```
Met Thr Glu Phe Val Val Leu Ile Pro Ala Arg Leu Asp Ser Ser Arg
  1               5                  10                  15

Leu Pro Gly Lys Ala Leu Ala Asp Ile His Gly Lys Pro Met Val Val
             20                  25                  30

Arg Val Ala Glu Gln Ala Ala Lys Ser Lys Ala Ala Arg Val Val Val
         35                  40                  45

Ala Thr Asp His Pro Asp Ile Gln Thr Ala Cys Gln Ala His Gly Ile
     50                  55                  60

Glu Val Val Met Thr Ser Asn Arg His Glu Ser Gly Thr Thr Arg Leu
 65                  70                  75                  80

Ala Glu Ala Ser Val Ala Leu Lys Leu Pro Pro His Leu Ile Val Val
                 85                  90                  95

Asn Val Gln Gly Asp Glu Pro Leu Ile Ala Pro Glu Leu Ile Asp Arg
            100                 105                 110

Thr Ala Glu Val Leu Val Glu Asn Asn Val Gln Met Ala Thr Ala Ala
        115                 120                 125

His Glu Leu His Asp Phe Asp Glu Leu Met Asn Pro Asn Ala Val Lys
    130                 135                 140

Val Val Leu Asp Lys Asn Arg Asn Ala Ile Tyr Phe Ser Arg Ala Pro
145                 150                 155                 160

Ile Pro Tyr Pro Arg Asp Ala Ile Arg Ala Gly Lys Arg Glu Met Pro
                165                 170                 175

Ser Glu Thr Ala Val Leu Arg His Ile Gly Ile Tyr Ala Tyr Arg Ala
            180                 185                 190
```

```
Gly Phe Leu Gln Arg Tyr Ala Glu Met Ser Val Ser Pro Leu Glu Thr
        195                 200                 205

Ile Glu Ser Leu Glu Gln Leu Arg Val Leu Trp His Gly Tyr Pro Ile
    210                 215                 220

Ala Val Glu Thr Ala Lys Glu Ala Pro Ala Ala Gly Val Asp Thr Gln
225                 230                 235                 240

Glu Asp Leu Asp Arg Val Arg Ala Val Phe Gln Thr Val
                245                 250
```

<210> SEQ ID NO 31
<211> LENGTH: 972
<212> TYPE: DNA
<213> ORGANISM: Neisseria meningitidis

<400> SEQUENCE: 31

```
atggcagaaa acggaaaata tctcgactgg gcacgcgaag tgttgcacgc cgaagcggaa      60
ggcttgcgcg aaattgcagc ggaattggac aaaaacttcg tccttgcggc agacgcgttg     120
ttgcactgca agggcagggt cgttatcacg gcatgggca agtcgggaca tatcgggcgc      180
aaaatggcgg caactatggc ctcgaccggc acgcctgcgt ttttcgtcca ccctgcggaa     240
gcggcacacg gcgatttggg tatgattgtg acaacgacg tggtcgtcgc gatttccaat      300
tccggcgaaa gcgacgaaat cgccgccatc atccccgcac tcaaacgcaa agacatcacg     360
cttgtctgca tcaccgcccg cccgattca accatggcgc gccatgccga catccacatc      420
acggcgtcgg tttccaaaga agcctgcccg ctggggcttg ccccgaccac cagcaccacc     480
gccgtcatgg ctttgggcga tgcgttggcg gtcgtcctgc tgcgcgcacg cgcgttcacg     540
cccgacgatt tcgccttgag ccatcctgcc ggcagcctcg gcaaacgcct acttttgcgc     600
gttgccgaca ttatgcacaa aggcggcggc ctgcctgccg tccgactcgg cacgcccttg     660
aaagaagcca tcgtcagcat gagtgaaaaa gggctgggca tgttggcggt aacggacggg     720
caaggccgtc tgaaaggcgt attcaccgac ggcgatttgc ccgcctgtt tcaagaatgc      780
gacaattta ccggtctttc gatagacgaa gtcatgcata cgcatcctaa accatctcc      840
gccgaacgtc tcgccaccga agccctgaaa gtcatgcagg caaaccatgt gaacgggctt     900
ctggttaccg atgcagatgg cgtgctgatc ggcgcgctga atatgcacga cctgctggcg     960
gcacggattg ta                                                        972
```

<210> SEQ ID NO 32
<211> LENGTH: 324
<212> TYPE: PRT
<213> ORGANISM: Neisseria meningitidis

<400> SEQUENCE: 32

```
Met Ala Glu Asn Gly Lys Tyr Leu Asp Trp Ala Arg Glu Val Leu His
 1               5                  10                  15

Ala Glu Ala Glu Gly Leu Arg Glu Ile Ala Ala Glu Leu Asp Lys Asn
                20                  25                  30

Phe Val Leu Ala Ala Asp Ala Leu Leu His Cys Lys Gly Arg Val Val
            35                  40                  45

Ile Thr Gly Met Gly Lys Ser Gly His Ile Gly Arg Lys Met Ala Ala
        50                  55                  60

Thr Met Ala Ser Thr Gly Thr Pro Ala Phe Phe Val His Pro Ala Glu
65                  70                  75                  80

Ala Ala His Gly Asp Leu Gly Met Ile Val Asp Asn Asp Val Val Val
                85                  90                  95
```

Ala Ile Ser Asn Ser Gly Glu Ser Asp Glu Ile Ala Ala Ile Ile Pro
            100                 105                 110

Ala Leu Lys Arg Lys Asp Ile Thr Leu Val Cys Ile Thr Ala Arg Pro
        115                 120                 125

Asp Ser Thr Met Ala Arg His Ala Asp Ile His Ile Thr Ala Ser Val
    130                 135                 140

Ser Lys Glu Ala Cys Pro Leu Gly Leu Ala Pro Thr Thr Ser Thr Thr
145                 150                 155                 160

Ala Val Met Ala Leu Gly Asp Ala Leu Ala Val Val Leu Leu Arg Ala
                165                 170                 175

Arg Ala Phe Thr Pro Asp Asp Phe Ala Leu Ser His Pro Ala Gly Ser
            180                 185                 190

Leu Gly Lys Arg Leu Leu Leu Arg Val Ala Asp Ile Met His Lys Gly
        195                 200                 205

Gly Gly Leu Pro Ala Val Arg Leu Gly Thr Pro Leu Lys Glu Ala Ile
    210                 215                 220

Val Ser Met Ser Glu Lys Gly Leu Gly Met Leu Ala Val Thr Asp Gly
225                 230                 235                 240

Gln Gly Arg Leu Lys Gly Val Phe Thr Asp Gly Asp Leu Arg Arg Leu
                245                 250                 255

Phe Gln Glu Cys Asp Asn Phe Thr Gly Leu Ser Ile Asp Glu Val Met
            260                 265                 270

His Thr His Pro Lys Thr Ile Ser Ala Glu Arg Leu Ala Thr Glu Ala
        275                 280                 285

Leu Lys Val Met Gln Ala Asn His Val Asn Gly Leu Leu Val Thr Asp
    290                 295                 300

Ala Asp Gly Val Leu Ile Gly Ala Leu Asn Met His Asp Leu Leu Ala
305                 310                 315                 320

Ala Arg Ile Val

<210> SEQ ID NO 33
<211> LENGTH: 325
<212> TYPE: PRT
<213> ORGANISM: Neisseria meningitidis

<400> SEQUENCE: 33

Met Ala Gly Asn Glu Lys Tyr Leu Asp Trp Ala Arg Glu Val Leu Leu
1               5                   10                  15

His Thr Glu Ala Glu Gly Leu Arg Glu Ile Ala Ala Asp Leu Asp Glu
            20                  25                  30

Asn Phe Ala Leu Ala Ala Asp Ala Leu Leu His Cys Lys Gly Arg Val
        35                  40                  45

Val Ile Thr Gly Met Gly Lys Ser Gly His Ile Gly Arg Lys Met Ala
    50                  55                  60

Ala Thr Met Ala Ser Thr Gly Thr Pro Ala Phe Phe Val His Pro Ala
65                  70                  75                  80

Glu Ala Ala His Gly Asp Leu Gly Met Ile Val Asp Asn Asp Val Val
                85                  90                  95

Val Ala Ile Ser Asn Ser Gly Glu Ser Asp Glu Ile Ala Ala Ile Ile
            100                 105                 110

Pro Ala Leu Lys Arg Lys Asp Ile Thr Leu Val Cys Ile Thr Ala Arg
        115                 120                 125

Pro Asp Ser Thr Met Ala Arg His Ala Asp Ile His Ile Thr Ala Ser
    130                 135                 140

```
Val Ser Lys Glu Ala Cys Pro Leu Gly Leu Ala Pro Thr Thr Ser Thr
145                 150                 155                 160

Thr Ala Val Met Ala Leu Gly Asp Ala Leu Ala Val Val Leu Leu Arg
                165                 170                 175

Ala Arg Ala Phe Thr Pro Asp Asp Phe Ala Leu Ser His Pro Ala Gly
            180                 185                 190

Ser Leu Gly Lys Arg Leu Leu Arg Val Ala Asp Ile Met His Lys
            195                 200                 205

Gly Gly Gly Leu Pro Ala Val Arg Leu Gly Thr Pro Leu Lys Glu Ala
        210                 215                 220

Ile Val Ser Met Ser Glu Lys Gly Leu Gly Met Leu Ala Val Thr Asp
225                 230                 235                 240

Gly Gln Gly Arg Leu Lys Gly Val Phe Thr Asp Gly Asp Leu Arg Arg
                245                 250                 255

Leu Phe Gln Glu Cys Asp Asn Phe Thr Gly Leu Ser Ile Asp Glu Val
            260                 265                 270

Met His Thr His Pro Lys Thr Ile Ser Ala Glu Arg Leu Ala Thr Glu
        275                 280                 285

Ala Leu Lys Val Met Gln Ala Asn His Val Asn Gly Leu Leu Val Thr
290                 295                 300

Asp Ala Asp Gly Val Leu Ile Gly Ala Leu Asn Met His Asp Leu Leu
305                 310                 315                 320

Ala Ala Arg Ile Val
                325

<210> SEQ ID NO 34
<211> LENGTH: 329
<212> TYPE: PRT
<213> ORGANISM: Escherichia coli

<400> SEQUENCE: 34

Met Ser Glu Arg His Leu Pro Asp Asp Gln Ser Ser Thr Ile Asp Pro
1               5                   10                  15

Tyr Leu Ile Thr Ser Val Arg Gln Thr Leu Ala Glu Gly Ala Arg
            20                  25                  30

Ala Arg Leu Gln Asn Leu Ser Lys Gln Leu Asp Ser Gly Gln Tyr Gln
            35                  40                  45

Arg Val Leu Asn Leu Ile Met Asn Cys Lys Gly His Val Ile Leu Ser
        50                  55                  60

Gly Met Gly Lys Ser Gly His Val Gly Arg Lys Met Ser Ala Thr Leu
65                  70                  75                  80

Ala Ser Thr Gly Thr Pro Ser Phe Phe Ile His Pro Ala Glu Ala Phe
                85                  90                  95

His Gly Asp Leu Gly Met Ile Thr Pro Tyr Asp Leu Leu Ile Leu Ile
            100                 105                 110

Ser Ala Ser Gly Glu Thr Asp Glu Ile Leu Lys Leu Val Pro Ser Leu
        115                 120                 125

Lys Asn Phe Gly Asn Arg Ile Ile Ala Ile Thr Asn Asn Gly Asn Ser
    130                 135                 140

Thr Leu Ala Lys Asn Ala Asp Ala Val Leu Glu Leu His Met Ala Asn
145                 150                 155                 160

Glu Thr Cys Pro Asn Asn Leu Ala Pro Thr Thr Ser Thr Thr Leu Thr
                165                 170                 175

Met Ala Ile Gly Asp Ala Leu Ala Ile Ala Met Ile Arg Gln Arg Lys
```

-continued

```
                180                 185                 190
Phe Met Pro Asn Asp Phe Ala Arg Tyr His Pro Gly Gly Ser Leu Gly
            195                 200                 205

Arg Arg Leu Leu Thr Arg Val Ala Asp Val Met Gln His Asp Val Pro
        210                 215                 220

Ala Val Gln Leu Asp Ala Ser Phe Lys Thr Val Ile Gln Arg Ile Thr
225                 230                 235                 240

Ser Gly Cys Gln Gly Met Val Met Val Glu Asp Ala Glu Gly Gly Leu
                245                 250                 255

Ala Gly Ile Ile Thr Asp Gly Asp Leu Arg Arg Phe Met Glu Lys Glu
            260                 265                 270

Asp Ser Leu Thr Ser Ala Thr Ala Gln Met Met Thr Arg Glu Pro
        275                 280                 285

Leu Thr Leu Pro Glu Asp Thr Met Ile Ile Glu Ala Glu Lys Met
    290                 295                 300

Gln Lys His Arg Val Ser Thr Leu Leu Val Thr Asn Lys Ala Asn Lys
305                 310                 315                 320

Val Thr Gly Leu Val Arg Ile Phe Asp
                325
```

<210> SEQ ID NO 35
<211> LENGTH: 328
<212> TYPE: PRT
<213> ORGANISM: Escherichia coli

<400> SEQUENCE: 35

```
Met Ser His Val Glu Leu Gln Pro Gly Phe Asp Phe Gln Gln Ala Gly
1               5                   10                  15

Lys Glu Val Leu Ala Ile Glu Arg Glu Cys Leu Ala Glu Leu Asp Gln
            20                  25                  30

Tyr Ile Asn Gln Asn Phe Thr Leu Ala Cys Glu Lys Met Phe Trp Cys
        35                  40                  45

Lys Gly Lys Val Val Met Gly Met Gly Lys Ser Gly His Ile Gly
    50                  55                  60

Arg Lys Met Ala Ala Thr Phe Ala Ser Thr Gly Thr Pro Ser Phe Phe
65                  70                  75                  80

Val His Pro Gly Glu Ala His Gly Asp Leu Gly Met Val Thr Pro
            85                  90                  95

Gln Asp Val Val Ile Ala Ile Ser Asn Ser Gly Glu Ser Ser Glu Ile
        100                 105                 110

Thr Ala Leu Ile Pro Val Leu Lys Arg Leu His Val Pro Leu Ile Cys
        115                 120                 125

Ile Thr Gly Arg Pro Glu Ser Ser Met Ala Arg Ala Ala Asp Val His
    130                 135                 140

Leu Cys Val Lys Val Ala Lys Glu Ala Cys Pro Leu Gly Leu Ala Pro
145                 150                 155                 160

Thr Ser Ser Thr Thr Ala Thr Leu Val Met Gly Asp Ala Leu Ala Val
                165                 170                 175

Ala Leu Leu Lys Ala Arg Gly Phe Thr Ala Glu Asp Phe Ala Leu Ser
            180                 185                 190

His Pro Gly Gly Ala Leu Gly Arg Lys Leu Leu Leu Arg Val Asn Asp
        195                 200                 205

Ile Met His Thr Gly Asp Glu Ile Pro His Val Lys Lys Thr Ala Ser
    210                 215                 220
```

```
Leu Arg Asp Ala Leu Leu Glu Val Thr Arg Lys Asn Leu Gly Met Thr
225                 230                 235                 240

Val Ile Cys Asp Asp Asn Met Met Ile Glu Gly Ile Phe Thr Asp Gly
                245                 250                 255

Asp Leu Arg Arg Val Phe Asp Met Gly Asp Val Asp Arg Gln Leu Ser
            260                 265                 270

Ile Ala Asp Val Met Thr Pro Gly Gly Ile Arg Val Arg Pro Gly Ile
        275                 280                 285

Leu Ala Val Glu Ala Leu Asn Leu Met Gln Ser Arg His Ile Thr Ser
    290                 295                 300

Val Met Val Ala Asp Gly Asp His Leu Leu Gly Val Leu His Met His
305                 310                 315                 320

Asp Leu Leu Arg Ala Gly Val Val
                325

<210> SEQ ID NO 36
<211> LENGTH: 308
<212> TYPE: PRT
<213> ORGANISM: Escherichia coli

<400> SEQUENCE: 36

Met Leu Glu Leu Gln Glu Ala Ser Arg Leu Pro Glu Arg Leu Gly Asp
1               5                   10                  15

Asp Phe Val Arg Ala Ala Asn Ile Ile Leu His Cys Glu Gly Lys Val
            20                  25                  30

Val Val Ser Gly Ile Gly Lys Ser Gly His Ile Gly Lys Lys Ile Ala
        35                  40                  45

Ala Thr Leu Ala Ser Thr Gly Thr Pro Ala Phe Phe Val His Pro Ala
    50                  55                  60

Glu Ala Leu His Gly Asp Leu Gly Met Ile Glu Ser Arg Asp Val Met
65                  70                  75                  80

Leu Phe Ile Ser Tyr Ser Gly Gly Ala Lys Glu Leu Asp Leu Ile Ile
                85                  90                  95

Pro Arg Leu Glu Asp Lys Ser Ile Ala Leu Leu Ala Met Thr Gly Lys
            100                 105                 110

Pro Thr Ser Pro Leu Gly Leu Ala Ala Lys Ala Val Leu Asp Ile Ser
        115                 120                 125

Val Glu Arg Glu Ala Cys Pro Met His Leu Ala Pro Thr Ser Ser Thr
    130                 135                 140

Val Asn Thr Leu Met Met Gly Asp Ala Leu Ala Met Ala Val Met Gln
145                 150                 155                 160

Ala Arg Gly Phe Asn Glu Glu Asp Phe Ala Arg Ser His Pro Ala Gly
                165                 170                 175

Ala Leu Gly Ala Arg Leu Leu Asn Lys Val His His Leu Met Arg Arg
            180                 185                 190

Asp Asp Ala Ile Pro Gln Val Ala Leu Thr Ala Ser Val Met Asp Ala
        195                 200                 205

Met Leu Glu Leu Ser Arg Thr Gly Leu Gly Leu Val Ala Val Cys Asp
    210                 215                 220

Ala Gln Gln Gln Val Gln Gly Val Phe Thr Asp Gly Asp Leu Arg Arg
225                 230                 235                 240

Trp Leu Val Gly Gly Gly Ala Leu Thr Thr Pro Val Asn Glu Ala Met
                245                 250                 255

Thr Val Gly Gly Thr Thr Leu Gln Ser Gln Ser Arg Ala Ile Asp Ala
            260                 265                 270
```

-continued

```
Lys Glu Ile Leu Met Lys Arg Lys Ile Thr Ala Ala Pro Val Val Asp
        275                 280                 285

Glu Asn Gly Lys Leu Thr Gly Ala Ile Asn Leu Gln Asp Phe Tyr Gln
    290                 295                 300

Ala Gly Ile Ile
305

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 37
gcgcgcctgt aattcggg                                                  18
```